(12) United States Patent
Horan et al.

(10) Patent No.: US 11,413,131 B2
(45) Date of Patent: *Aug. 16, 2022

(54) VASCULAR FILTER DEVICE

(71) Applicant: Novate Medical Limited, Dublin (IE)

(72) Inventors: Steven Horan, Galway (IE); Paul Gilson, County Galway (IE); Karl Keating, Galway (IE); Aidan Goggin, County Donegal (IE); Jerome Henry, Castlebar (IE); Jacqueline O'Gorman, County Clare (IE); Shane Molloy, County Galway (IE)

(73) Assignee: Novate Medical Limited, Galway (IE)

( * ) Notice: Subject to any disclaimer, the term of this patent is extended or adjusted under 35 U.S.C. 154(b) by 108 days.

This patent is subject to a terminal disclaimer.

(21) Appl. No.: 16/589,960

(22) Filed: Oct. 1, 2019

(65) Prior Publication Data

US 2020/0030076 A1 Jan. 30, 2020

Related U.S. Application Data

(63) Continuation of application No. 15/428,771, filed on Feb. 9, 2017, now Pat. No. 10,470,865, which is a
(Continued)

(51) Int. Cl.
*A61F 2/01* (2006.01)

(52) U.S. Cl.
CPC .......... *A61F 2/012* (2020.05); *A61F 2/0105* (2020.05); *A61F 2/011* (2020.05);
(Continued)

(58) Field of Classification Search
CPC .......... A61F 2/01; A61F 2/0103; A61F 2/105; A61F 2/108; A61F 2/011; A61F 2/013;
(Continued)

(56) References Cited

U.S. PATENT DOCUMENTS

| 5,344,427 A | 9/1994 | Cottenceau et al. |
| 5,375,612 A | 12/1994 | Cottenceau et al. |

(Continued)

FOREIGN PATENT DOCUMENTS

| DE | 40 30 998 A1 | 4/1991 |
| DE | 102008031299 A1 | 1/2010 |

(Continued)

*Primary Examiner* — Robert A Lynch
(74) *Attorney, Agent, or Firm* — Seager, Tufte & Wickhem LLP

(57) ABSTRACT

A vascular filter device (1) comprises a plurality of filter elements (6) which are movable from a capturing position to an open position upon elapse of a predetermined period of time. In the capturing position the filter elements (6) are configured to capture thrombus passing through the inferior vena cava. In the open position the filter elements (6) are configured to facilitate unrestricted blood flow. The filter elements (6) are biased towards the open position. The filter (1) comprises a holder member (10) to temporarily hold the filter elements (6) in the capturing position until elapse of the predetermined period of time. The holder member (10) comprises a biostable wire element (12) which extends through an opening (13) in each filter element (6), and a biodegradable/bioabsorbable stop element (11). Upon biodegrading/bioabsorbing of the stop element (11), the filter elements (6) are free to move from the capturing position to the open position.

17 Claims, 54 Drawing Sheets

Related U.S. Application Data continuation of application No. 14/162,429, filed on Jan. 23, 2014, now abandoned, which is a continuation of application No. 12/688,481, filed on Jan. 15, 2010, now Pat. No. 8,668,713.

(60) Provisional application No. 61/145,303, filed on Jan. 16, 2009.

(52) U.S. Cl.
CPC . *A61F 2002/016* (2013.01); *A61F 2210/0004* (2013.01); *A61F 2230/005* (2013.01); *A61F 2230/0067* (2013.01); *A61F 2230/0086* (2013.01); *A61F 2250/0059* (2013.01); *Y10T 29/49826* (2015.01)

(58) Field of Classification Search
CPC .......... A61F 2002/016; A61F 2002/018; A61F 2/0105; A61F 2/012; A61F 2/82; A61F 2/90; A61F 2/95; A61F 2210/0004; A61F 2230/005; A61F 2230/0067; A61F 2230/0086; A61F 2250/0059
See application file for complete search history.

(56) References Cited

U.S. PATENT DOCUMENTS

| | | | |
|---|---|---|---|
| 5,383,887 A * | 1/1995 | Nadal | A61F 2/01 606/200 |
| 5,634,942 A | 6/1997 | Chevillon et al. | |
| 5,725,550 A | 3/1998 | Nadal | |
| 5,800,525 A | 9/1998 | Bachinski et al. | |
| 5,853,420 A | 12/1998 | Chevillon et al. | |
| 5,968,071 A | 10/1999 | Chevillon et al. | |
| 6,193,739 B1 | 2/2001 | Chevillon et al. | |
| 6,214,025 B1 | 4/2001 | Thistle et al. | |
| 6,241,746 B1 | 6/2001 | Bosma et al. | |
| 6,248,128 B1 | 6/2001 | Berry et al. | |
| 6,267,776 B1 | 7/2001 | O'Connell | |
| 6,312,461 B1 | 11/2001 | Unsworth et al. | |
| 6,482,227 B1 | 11/2002 | Solovay | |
| 6,517,559 B1 * | 2/2003 | O'Connell | A61F 2/0103 606/158 |
| 6,527,962 B1 | 3/2003 | Nadal | |
| 6,582,447 B1 | 6/2003 | Patel et al. | |
| 6,605,111 B2 | 8/2003 | Bose et al. | |
| 6,652,558 B2 | 11/2003 | Patel et al. | |
| 6,666,882 B1 | 12/2003 | Bose et al. | |
| 6,669,721 B1 | 12/2003 | Bose et al. | |
| 6,852,076 B2 | 2/2005 | Nikolic et al. | |
| 6,881,218 B2 * | 4/2005 | Beyer | A61F 2/0103 606/200 |
| 6,932,832 B2 | 8/2005 | Patel et al. | |
| 6,966,923 B2 | 11/2005 | Gittings | |
| 6,972,025 B2 | 12/2005 | WasDyke | |
| 7,001,424 B2 | 2/2006 | Patel et al. | |
| 7,094,248 B2 | 8/2006 | Bachinski et al. | |
| 7,261,731 B2 | 8/2007 | Patel et al. | |
| 7,279,007 B2 | 10/2007 | Nikolic et al. | |
| 7,534,251 B2 | 5/2009 | WasDyke | |
| 8,025,675 B2 * | 9/2011 | Shirley | A61F 2/01 606/200 |
| 2001/0044652 A1 | 11/2001 | Moore | |
| 2003/0120303 A1 | 6/2003 | Boyle et al. | |
| 2003/0139765 A1 * | 7/2003 | Patel | A61F 2/01 606/200 |
| 2003/0176888 A1 * | 9/2003 | O'Connell | A61F 2/01 606/200 |
| 2003/0208227 A1 | 11/2003 | Thomas | |
| 2004/0019374 A1 | 1/2004 | Hojeibane et al. | |
| 2004/0220611 A1 | 11/2004 | Ogle | |
| 2005/0080480 A1 | 4/2005 | Bolea et al. | |
| 2005/0096735 A1 | 5/2005 | Hojeibane et al. | |
| 2005/0107822 A1 | 5/2005 | WasDyke | |
| 2005/0159804 A1 | 7/2005 | Lad et al. | |
| 2005/0209632 A1 * | 9/2005 | Wallace | A61F 2/0105 606/200 |
| 2006/0025852 A1 | 2/2006 | Armstrong et al. | |
| 2006/0142836 A1 | 6/2006 | Hartley et al. | |
| 2007/0032816 A1 | 2/2007 | O'Connell et al. | |
| 2007/0112372 A1 | 5/2007 | Sosnowkski et al. | |
| 2007/0203571 A1 | 8/2007 | Kaplan et al. | |
| 2007/0233241 A1 | 10/2007 | Graf et al. | |
| 2008/0027481 A1 | 1/2008 | Gilson et al. | |
| 2008/0188887 A1 | 8/2008 | Batiste | |
| 2008/0208245 A1 | 8/2008 | Hoffman | |
| 2010/0185227 A1 | 7/2010 | Horan et al. | |
| 2010/0185230 A1 | 7/2010 | Horan et al. | |
| 2012/0029552 A1 | 2/2012 | Horan et al. | |
| 2012/0245620 A1 | 9/2012 | Gilson et al. | |

FOREIGN PATENT DOCUMENTS

| | | |
|---|---|---|
| EP | 0 565 395 A1 | 10/1993 |
| EP | 0 598 635 A1 | 5/1994 |
| EP | 0 655 228 A1 | 5/1995 |
| EP | 0678284 A1 | 10/1995 |
| EP | 0 582 493 A1 | 7/1997 |
| EP | 0 935 975 A1 | 8/1999 |
| EP | 0 605 276 A1 | 2/2000 |
| EP | 1 103 233 A1 | 5/2001 |
| EP | 1 258 228 A1 | 11/2002 |
| EP | 0 759 287 A1 | 2/2003 |
| EP | 0 737 451 A1 | 9/2003 |
| EP | 1 616 530 A1 | 1/2006 |
| FR | 2 764 503 | 12/1998 |
| FR | 2 814 670 | 4/2002 |
| FR | 2 718 950 | 10/2005 |
| WO | 00/56390 | 9/2000 |
| WO | 00/66031 | 11/2000 |
| WO | 01/62184 A2 | 8/2001 |
| WO | 02/22048 A2 | 3/2002 |
| WO | 2006/020425 A1 | 2/2006 |
| WO | 2006/074163 A2 | 7/2006 |
| WO | 2006/107939 A1 | 10/2006 |
| WO | 2006/116636 A1 | 11/2006 |
| WO | 2007/079407 | 7/2007 |
| WO | 2008/010197 A2 | 1/2008 |

\* cited by examiner

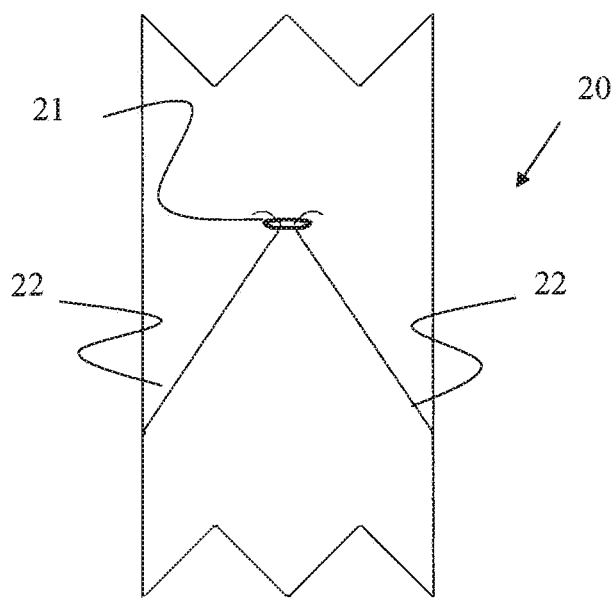
Fig. 9
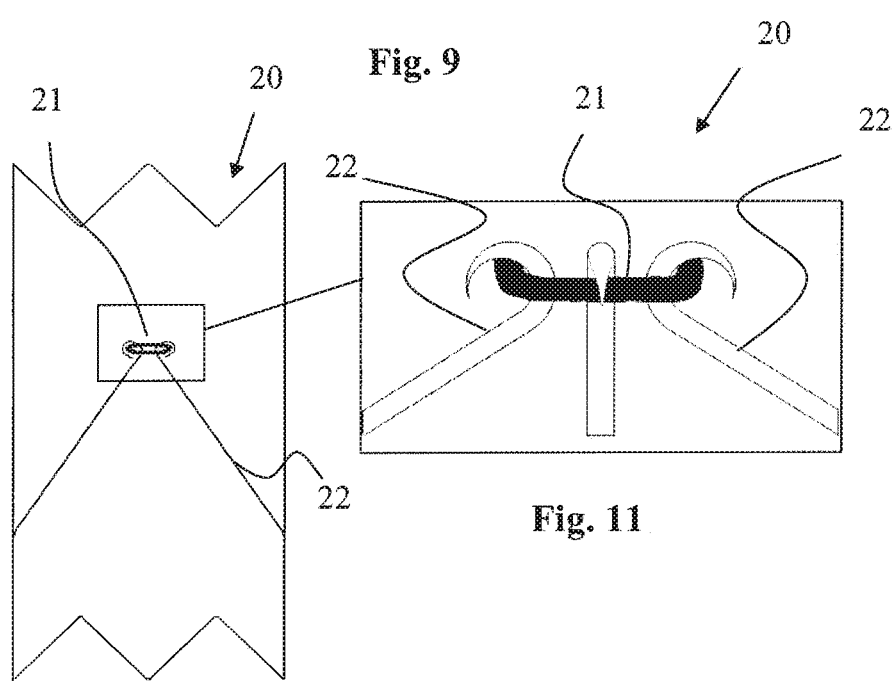
Fig. 10
Fig. 11

SECTION A-A

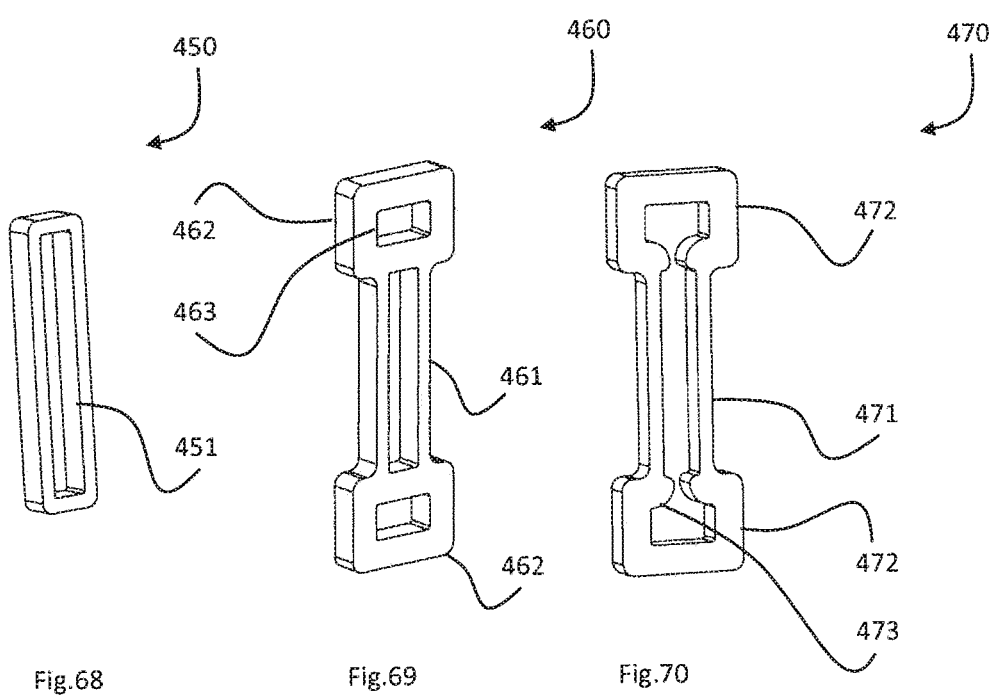

VASCULAR FILTER DEVICE

RELATED APPLICATIONS

This application is a continuation of U.S. patent application Ser. No. 15/428,771, filed on Feb. 9, 2017, which is a continuation of U.S. patent application Ser. No. 14/162,429, filed on Jan. 23, 2014 (now abandoned), which is a continuation of U.S. patent application Ser. No. 12/688,481, filed on Jan. 15, 2010, now U.S. Pat. No. 8,668,713, which claims the benefit of priority from U.S. Provisional Application No. 61/145,303, filed on Jan. 16, 2009, the entire contents of each of which is incorporated herein by reference.

INTRODUCTION

This invention relates to a vascular filter device and to a method of manufacturing such a device.

WO2008/010197 (Novate Medical Limited) describes such a device. It comprises a support extending around the vessel wall and which supports a filter. The filter comprises a number of filter elements, and in some embodiments they are retained by a holder member in a closed state for capturing thrombus. The holder member biodegrades after a period of time and releases the filter elements so that they can move to an open position against the vessel wall. The latter may be referred to as filter conversion.

The invention is directed towards providing a filter device with additional control over the conversion time and reliability.

SUMMARY OF THE INVENTION

According to the invention, there is provided a vascular filter device comprising a filter comprising one or more filter elements, the one or more filter elements being movable from a capturing position to capture thrombus passing through a blood vessel, to an open position to facilitate unrestricted blood flow. A holder holds the filter elements in the capturing position. The filter elements may be biased towards the open position, and the holder may be configured to temporarily hold the filter element in the capturing position until elapse of a predetermined period of time.

In one embodiment, the predetermined period of time is between approximately 4 months and approximately 24 months.

In one embodiment, the predetermined period of time is between approximately 4 days and approximately 4 months.

In one embodiment, at least part of the holder is biodegradable and/or bioabsorbable. In one embodiment, all of the holder is biodegradable and/or bioabsorbable. In one embodiment, at least part of the holder is biostable.

In one embodiment, the holder comprises one or more predetermined failure points.

In one embodiment, at least part of the holder engages with the filter element to hold the filter element in the capturing position.

In one embodiment, at least part of the holder extends through an opening in the filter element to hold the filter element in the capturing position.

In one embodiment, the filter comprises a plurality of filter elements, and in the capturing position the filter elements are arranged with the openings circumferentially spaced apart. In one embodiment, in the capturing position the opening faces circumferentially. In one embodiment, in the capturing position the holder comprises a first element extending through the opening and a second element to maintain the first element extending through the opening. In one embodiment, in the capturing position the second element connects a first end of the first element to a second end of the first element. In one embodiment, the first element is biostable. In one embodiment, the second element is biodegradable and/or bioabsorbable. In one embodiment, the radial dimension of the filter element radially inwardly of the opening is greater than the radial dimension of the filter element radially outwardly of the opening. In one embodiment, at least part of the opening has a chamfered or rounded edge. In one embodiment, the holder comprises a first element connected to a second element at a connection point, the first element extending from the connection point through an opening in a first filter element, and the second element extending from the connection point through an opening in a second filter element.

In one embodiment, the element extends substantially radially from the connection point through the opening in the filter element. In one embodiment, the filter comprises a plurality of filter elements, and in the capturing position the filter elements are arranged with the openings aligned in a straight line. In one embodiment, in the capturing position the openings are aligned longitudinally in a straight line. In one embodiment, in the capturing position the openings are aligned radially in a straight line. In one embodiment, the longitudinal axis of the holder is substantially straight. In one embodiment, in a first end of the holder is disconnected from a second end of the holder. In one embodiment, at least part of the holder is formed integrally with the filter elements.

In one embodiment, the holder engages with the internal wall of the opening. In one embodiment, the holder engages with the filter element externally of the opening. In one embodiment, the holder is substantially rigid. In one embodiment, the holder comprises at least one pin element. In one embodiment, the pin element comprises a central element extendable through the opening in the filter element, and at least one stop element at an end of the central element externally of the opening. In one embodiment, the pin element comprises a first stop element at a first end of the central element and a second stop element at a second end of the central element. In one embodiment, the stop element is formed separately to the central element.

In one embodiment, at least one stop element is formed integrally with the central element. In one embodiment, at least part of the stop element is biodegradable and/or bioabsorbable. In one embodiment, at least part of the stop element is biostable. In one embodiment, at least part of the central element is biostable. In one embodiment, at least part of the central element is biodegradable and/or bioabsorbable.

In one embodiment, the holding means extends around at least part of the filter element to hold the filter element in the capturing position.

In one embodiment, the holder comprises a ring element. In one embodiment, the holder comprises a tube element. In one embodiment, at least part of the holder is substantially conically shaped. In one embodiment, at least part of the holder comprises a mesh. In one embodiment, the holder is located proximally of the distal end of the filter element.

In one embodiment, the holder comprises a first opening through which a first set of one or more filter elements extends in the capturing position, and a second opening through which a second set of one or more filter elements extends in the capturing position. In one embodiment, the first set of one or more filter elements extends through the first opening in the open position.

In one embodiment, the wall thickness of the holder around the first opening is greater than the wall thickness of the holder around the second opening. In one embodiment, the device is configured to couple the holder to the filter element in the capturing position. In one embodiment, the device is configured to couple the holder to the filter element in the open position. In one embodiment, the filter element comprises at least one bend to couple the holder to the filter element. In one embodiment, the angle of the bend is greater than 60°.

In one embodiment, at least part of the filter element is twisted. In one embodiment, the device comprises a vena cava filter.

In one embodiment, the holder comprises a ring around the filter element ends and an insert to retain the filter element ends in set positions.

In one embodiment, the holder comprises a pin extending through filter element openings, and the pin is tied at its ends.

In one embodiment, the holder comprises a pin extending through filter element openings and there is a heat-shrunk sleeve at the ends of the pin.

In one embodiment, the holder comprises a pin extending through filter element openings and the pin has a clawed end with splayed-out claws for retention of the pin in place.

In one embodiment, the holder comprises a pin extending through filter element openings and having barbed ends. In one embodiment, the pin is bent at the ends.

In one embodiment, the holder comprises a coupler through which filter element ends extend. In one embodiment, the holder comprises screw cap and the ends of the filter elements are engaged with threads of the screw cap.

In one embodiment, the holder comprises coupler having an opening into which the ends of the filter elements are snap-fitted.

In one embodiment, the ends of the filter elements are hooked.

In one embodiment, the holder comprises a lumen for flow of biodegraded material.

In one embodiment, the invention provides a method of manufacturing a filter device, the method comprising the step of engaging a holder with one or more filter elements to hold the one or more filter elements in a capturing position.

In one embodiment, the method comprises the step of extending at least part of the holder through an opening in the filter element.

In one embodiment, the method comprises the step of connecting a first end of the holder to a second end of the holder to maintain the holder extending through the opening in the filter element. In one embodiment, the holder comprises a central element extendable through the opening in the filter element, and at least one stop element at an end of the central element externally of the opening. In one embodiment, the central element and the stop element are formed integrally. In one embodiment, the method comprises the step of deforming the holder to form the central element and the stop element. In one embodiment, the central element and the stop element are formed separately. In one embodiment, the method comprises the step of attaching the stop element to the central element. In one embodiment, the method comprises the step of extending the holder around at least part of the filter element. In one embodiment, the holder is chosen with a configuration according to desired degradation time as a function of time for flow of degraded material away from the site.

According to another aspect the invention there is provided a vascular filter comprising:
one or more capture members, the one or more capture members being movable from a capturing position to an open position, in the capturing position the one or more capture members being configured to capture thrombus passing through a blood vessel, in the open position the one or more capture members being configured to facilitate unrestricted blood flow, and
means to hold the one or more capture members in the capturing position.

By capturing the thrombus, the filter prevents the thrombus from passing to the heart or lungs, which may cause pulmonary embolism. By supporting the capture members this ensures that the capture members are maintained in the desired location in the blood vessel.

In one embodiment of the invention the capture member is biased towards the open position. Preferably the holding means is configured to temporarily hold the capture member in the capturing position until elapse of a predetermined period of time. The predetermined period of time may be between approximately 4 months and approximately 24 months. Ideally at least part of the holding means is biodegradable and/or bioabsorbable. All of the holding means may be biodegradable and/or bioabsorbable. At least part of the holding means may be biostable. Most preferably the holding means comprises one or more predetermined failure points.

In another embodiment at least part of the holding means engages with the capture member to hold the capture member in the capturing position.

In one case at least part of the holding means extends through an opening in the capture member to hold the capture member in the capturing position. The filter may comprise a plurality of capture members, and in the capturing position the capture members are arranged with the openings in the capture members circumferentially spaced apart. In the capturing position the opening in the capture member may face circumferentially. This arrangement enables the holding means to pass smoothly from one opening to the next opening. Preferably in the capturing position the holding means comprises a first element extending through the opening in the capture member and a second element to maintain the first element extending through the opening in the capture member. Ideally in the capturing position the second element connects a first end of the first element to a second end of the first element. Most preferably the first element is biostable. The second element may be biodegradable and/or bioabsorbable.

The radial dimension of the capture member radially inwardly of the opening may be greater than the radial dimension of the capture member radially outwardly of the opening. At least part of the opening may have a chamfered edge. In this manner any inadvertent wear or damage to the holding means is avoided.

In another case the holding means comprises a first element connected to a second element at a connection point, the first element extending from the connection point through an opening in a first capture member, and the second element extending from the connection point through an opening in a second capture member. Preferably the element extends substantially radially from the connection point through the opening in the capture member.

The filter may comprise a plurality of capture members, and in the capturing position the capture members are arranged with the openings in the capture members aligned in a straight line. In the capturing position the openings in the capture members may be aligned longitudinally in a straight line. In the capturing position the openings in the capture members may be aligned radially in a straight line. In one embodiment the longitudinal axis of the holding means is substantially straight. Preferably a first end of the holding means is disconnected from a second end of the holding means. Ideally at least pert of the holding means is formed integrally with the capture member. The holding means may engage with the internal wall of the opening of the capture member. The holding means may engage with the capture member externally of the opening. Most preferably the holding means is substantially rigid. The holding means may comprise at least one pin element. The pin element may comprise a central element extendable through the opening in the capture member, and at least one stop element at an end of the central element externally of the opening. The pin element may comprise a first stop element at a first end of the central element and a second stop element at a second end of the central element. The stop element may be formed separately to the central element. The stop element may be formed integrally with the central element. At least part of the stop element may be biodegradable and/or bioabsorbable. At least part of the stop element may be biostable. At least part of the central element may be biostable. At least part of the central element may be biodegradable and/or bioabsorbable.

In another embodiment the holding means extends around at least part of the capture member to hold the capture member in the capturing position. The holding means may comprise a ring element. The holding means may comprise a tube element. At least part of the holding means may be substantially conically shaped. At least part of the holding means may comprise a mesh. Preferably the holding means is located proximally of the distal end of the capture member. Ideally the holding means comprises a first opening through which a first set of one or more capture members extends in the capturing position, and a second opening through which a second set of one or more capture members extends in the capturing position. Most preferably the first set of one or more capture members extends through the first opening in the open position. In this manner the holding means is coupled to the first set of one or more capture members in the open position. The wall thickness of the holding means around the first opening may be greater than the wall thickness of the holding means around the second opening. This arrangement results in failure of the holding means occurring at the second opening.

In one case the filter is configured to couple the holding means to the capture member in the capturing position. This arrangement prevents any inadvertent movement of the holding means relative to the capture member in the capturing position. Preferably the filter is configured to couple the holding means to the capture member in the open position. This arrangement prevents any inadvertent movement of the holding means relative to the capture member in the open position.

Ideally the capture member comprises at least one bend to couple the holding means to the capture member. Most preferably the angle of the bend is greater than 60 degrees.

At least part of the capture member may be twisted.

In another case the filter comprises a vena cave filter.

In another aspect of the invention there is also provided a method of manufacturing a vascular filter, the method comprising the step of engaging a holder member with one or more capture members to hold the one or more capture members in a capturing position.

In one embodiment of the invention the method comprises the step of extending at least part of the holder member through an opening in the capture member. Preferably the method comprises the step of connecting a first end of the holder member to a second end of the holder member to maintain the holder member extending through the opening in the capture member. The holder member may comprise a central element extendable through the opening in the capture member, and at least one stop element at an end of the central element externally of the opening. The central element and the stop element may be formed integrally. Preferably the method comprises the step of deforming the holder member to form the central element and the stop element. The central element and the stop element may be formed separately. Preferably the method comprises the step of attaching the stop element to the central element.

In another embodiment the method comprises the step of extending the holder member around at least part of the capture member.

In this specification the terms "filter element", "capture member", and "capture arm" are used interchangeably all to mean a part of a filter.

BRIEF DESCRIPTION OF THE DRAWINGS

The invention will be more clearly understood from the following description of some embodiments thereof, given by way of example only, with reference to the accompanying drawings, in which:

FIG. 8(d) is an enlarged isometric view of part of this device;

FIG. 9 is an isometric view of another vascular filter device according to the invention during manufacture, FIG. 10 is an isometric view of this device after manufacture, FIG. 11 is an enlarged isometric view of part of this device.

FIGS. 68 to 70 are perspective views of alternative holder members;

DETAILED DESCRIPTION

Figure 1A:
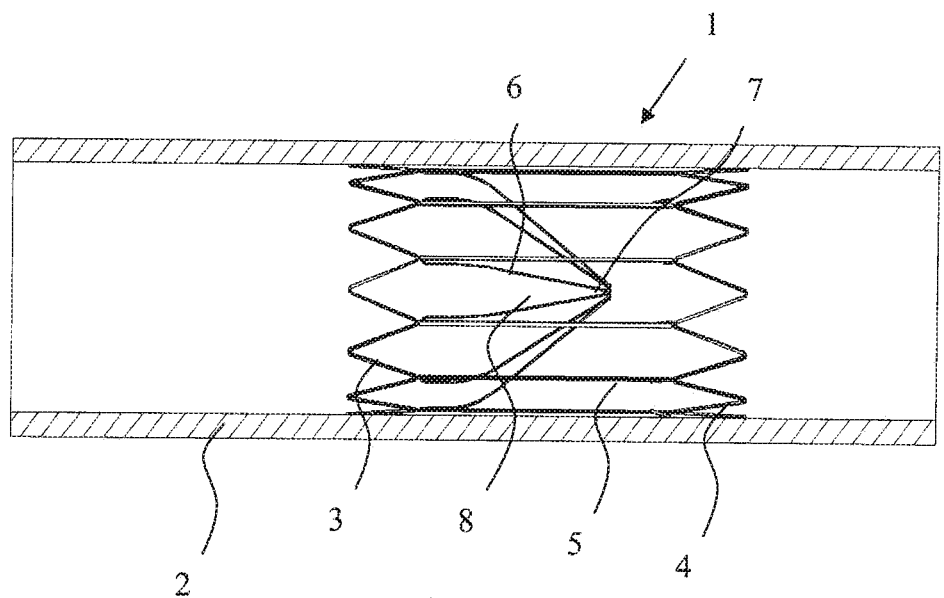
FIG. 1(a) is a side view of a vascular filter device according to the invention in a 30 blood vessel.

Referring to the drawings, and initially to FIGS. 1 to 8 thereof, there is illustrated a vascular filter device 1 according to the invention.

Figure 4:
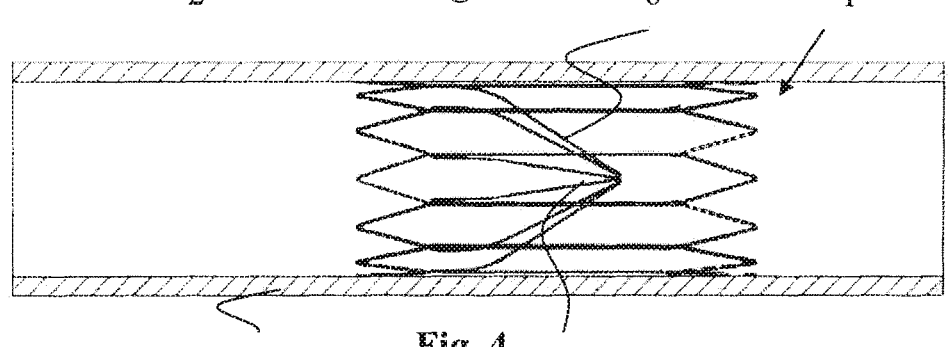
FIGS. 4 to 8 show this device in use.
Figure 5:
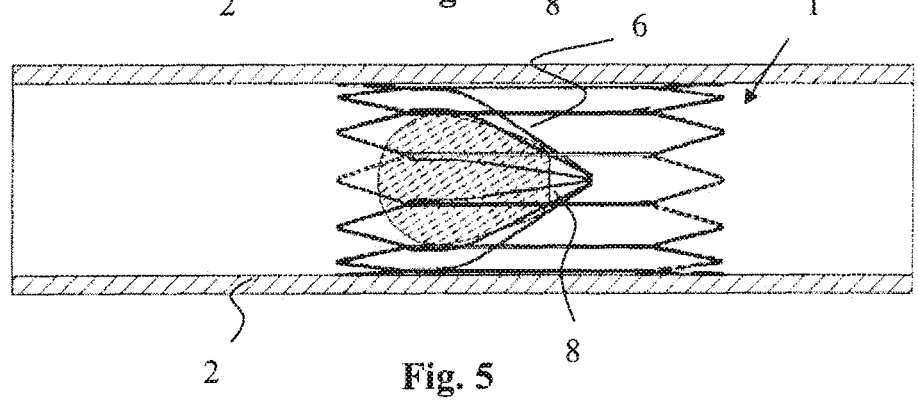

The device 1 is suitable for use as an inferior vena cava filter in the inferior vena cava 2. The device 1 is movable from a capturing position (FIG. 4) to an open position (FIG. 7) upon elapse of a predetermined period of time. In the capturing position the device 1 is configured to capture thrombus passing through the inferior vena cava 2 towards the heart and the lungs (FIG. 5). The device 1 may thus be used to prevent pulmonary embolism. In the open position the filter 1 is configured to facilitate unrestricted blood flow.

As illustrated in FIG. 1, the device 1 comprises a proximal support hoop 3 at the proximal end of the device 1, a distal support hoop 4 at the distal end of the device 1, and a plurality of support struts 5 extending between the proximal support hoop 3 and the distal support hoop 4.

In this patent specification, the terms 'proximal' and "distal" are used in the sense that a proximal part is upstream of a distal part with reference to the direction of blood flow.

The proximal support hoop 3 comprises a wire element which extends circumferentially around the internal wall of the inferior vena cava 2 in a sinusoid wave pattern. Similarly the distal support hoop 4 comprises a wire element which extends circumferentially around the internal wall of the inferior vena cava 2 in a sinusoid wave pattern. The support struts 5 extend longitudinally along the internal wall of the inferior vena cava 2. The support struts 5 connect the proximal support hoop 3 to the distal support hoop 4. In this case the proximal support hoop 3, the distal support hoop 4 and the support struts 5 are formed integrally. The proximal support hoop 3, the distal support hoop 4 and the support struts 5 may be of a shape-memory material, such as Nitinol™.

The device 1 is movable between a collapsed delivery position and an expanded deployed position. The device 1 is biased radially outwardly towards the deployed position. When the device 1 is deployed in the inferior vena cava 2, the support hoops 3 and 4 exert a force radially outwardly on the internal wall of the inferior vena cava 2. In this manner the support hoops 3 and 4 support the filter elements 6 in position relative to the wall of the inferior vena cava 2.

As illustrated in FIG. 1, the device 1 comprises twelve filter elements 6 for capturing thrombus passing through the inferior vena cava 2. Each filter element 6 is formed integrally with the proximal support hoop 3. An opening 13 is provided at the distal end of each of the filter elements 6 (FIG. 1(a)).

The filter elements 6 are movable from the capturing position (FIG. 4) to the open position (FIG. 7) upon elapse of the predetermined period of time. In the capturing position the filter elements 6 are configured to capture thrombus passing though the inferior vena cava 2 towards the heart and the lungs (FIG. 5). In the open position the filter elements 6 are configured to facilitate unrestricted blood flow.

In the capturing position the filter elements 6 extend in a substantially straight line to an apex 7. In this manner the filter elements 6 define a generally conically shaped capture region 8 within which thrombus may be captured. When the device 1 is deployed in the inferior vena cava 2, the apex 7 is substantially in-line with the longitudinal axis extending through the centre of the inferior vena cava 2, and the capture region 8 is located in the region of the centre of the inferior vena cava 2. When the device 1 is deployed in the inferior vena cava 2, the filter elements 6 extend in the direction of blood flow through the inferior vena cava 2.

In the capturing position the filter elements 6 are arranged with the openings 13 circumferentially spaced apart in a loop (FIG. 1(a)).

The distal end of the distal support hoop 4 is located distally of the filter elements 6 and the apex 7, and the proximal end of the proximal support hoop 3 is located proximally of the filter elements 6.

The filter elements 6 are movable from the capturing position to the open position upon elapse of the predetermined period of time. The filter elements 6 are biased towards the open position.

Figure 1B:
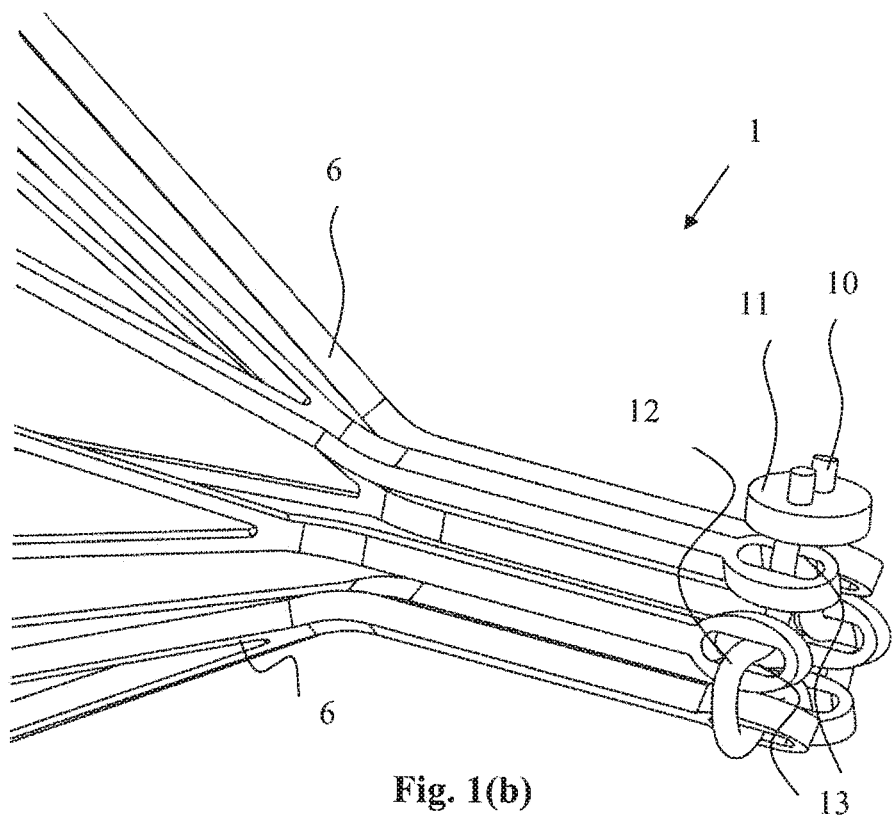
FIG. 1(b) is an enlarged isometric view showing a holder member of this device.

As illustrated in FIG. 1(b), the device 1 comprises a holder member 10 at the distal ends of the filter elements 6 to temporarily hold the filter elements 6 in the capturing position until elapse of the predetermined period of time. The predetermined period of time may be between approximately 4 months and approximately 24 months. The holder member 10 comprises a flexible wire element 12 which extends in a loop through the opening 13 in each filter element 6, and a stop element 11. The wire element 12 engages with each filter element 6 to hold the filter elements 6 in the capturing position. In the capturing position the stop element 11 is fixedly attached to each end of the wire element 12 and thus connects each end of the wire element 12 together. In this manner the stop element 11 maintains the wire element 12 extending through the openings 13 in the filter elements 6.

The wire element 12 is biostable, and the stop element 11 is biodegradable and/or bioabsorbable upon elapse of the predetermined period of time. Upon biodegrading/bioabsorbing of the stop element 11, the filter elements 6 are free to move from the capturing position to the open position. The filter elements 6 are not biodegradable or bioabsorbable.

The flexible biostable wire 12 is used to tie the filter elements 6 together. The ends of the flexible biostable element 12 are secured with the biodegradable component 11. The biodegradable element 11 may be over-moulded, snap fitted, bonded, or crimped onto the biostable ends. The wire 12 may be looped around one of the eyelets 13 to ensure that the wire 12 moves with the eyelets 13 to the vessel wall upon conversion rather than becoming an embolus.

During manufacture of the vascular device 1, the wire element 12 is extended through the openings 13. The stop element 11 is fixedly attached to each end of the wire element 12 to connect each end of the wire element 12 together. In this manner the wire element 12 is maintained extending through the openings 13. The wire element 12 engages with the filter elements 6 to hold the filter elements 6 in the capturing position.

Figure 2:
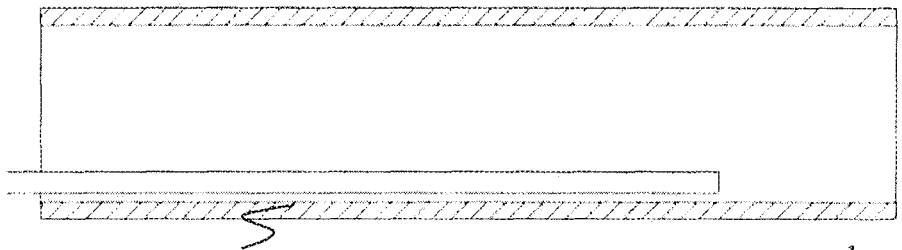
FIGS. 2 and 3 are diagrams showing deployment of the device of FIG. 1.
Figure 3:
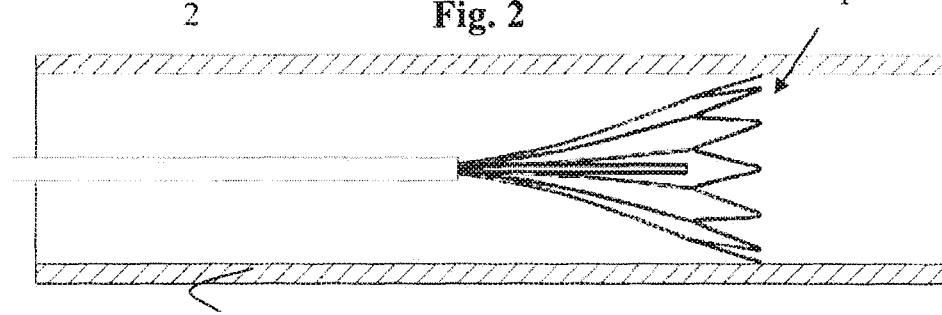

In use the device 1 is collapsed to the delivery configuration, and at least partially loaded into a delivery catheter. The delivery catheter is advanced through the inferior vena cava 2 until the collapsed device 1 reaches the desired location in the inferior vena cava 2 (FIG. 2). A restraining sheath of the delivery catheter is then moved proximally relative to the device 1 to fully uncover the device 1 (FIG. 3). Due to the biasing nature of the device 1, it moves from the collapsed delivery configuration to the expanded deployed configuration (FIG. 4). In the deployed configuration, the support hoops 3, 4 exert a radially outward force on the internal wall of the inferior vena cava 2 to support the filter elements 6 in the desired position in the inferior vena cava 2.

Figure 6:
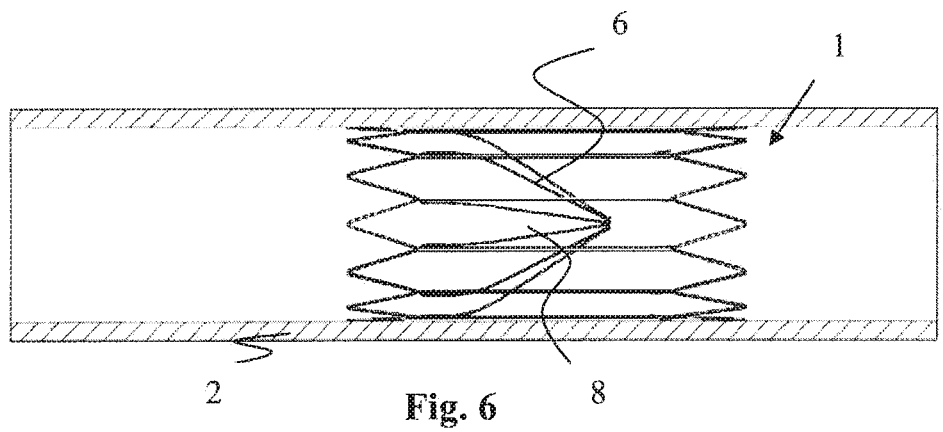

In the event of thrombus passing through the inferior vena cava 2 towards the heart and the lungs, the thrombus will be captured in the capture region 8 of the device 1 (FIG. 5). The thrombus will thus be prevented from passing into the heart and the lungs which could otherwise lead to pulmonary embolism. The captured thrombus will gradually be broken down by the body into smaller size particles which will significantly reduce the hazardous effects of embolism (FIG. 6).

Figure 7:
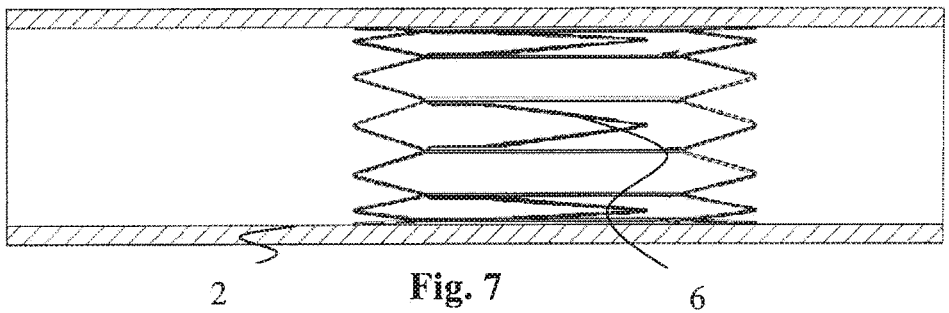
Figure 8:
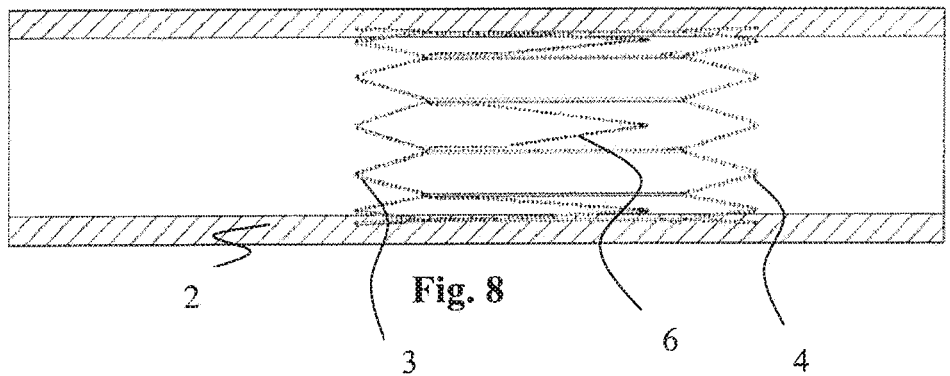
Figure 8A:
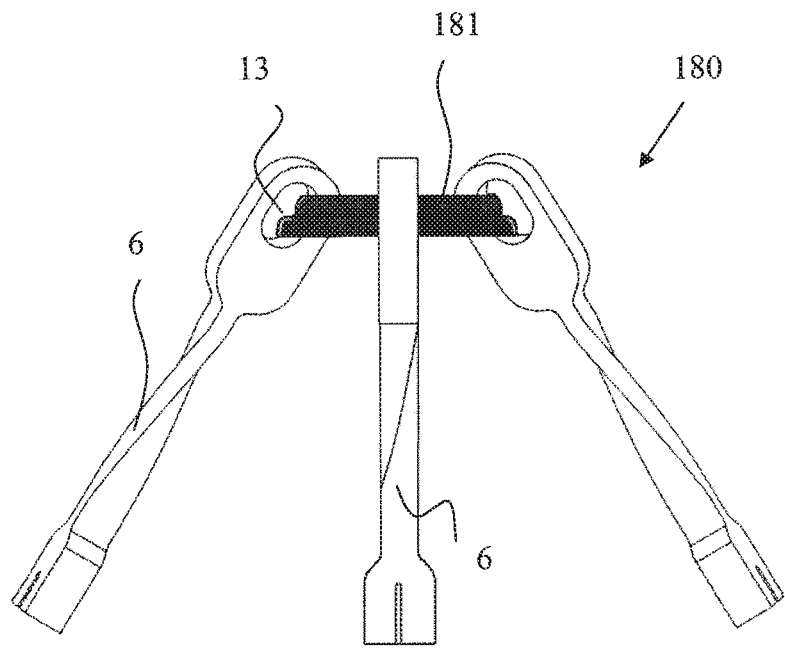
FIG. 8(a) is a side view of part of another vascular filter device according to the invention.
Figure 8B:
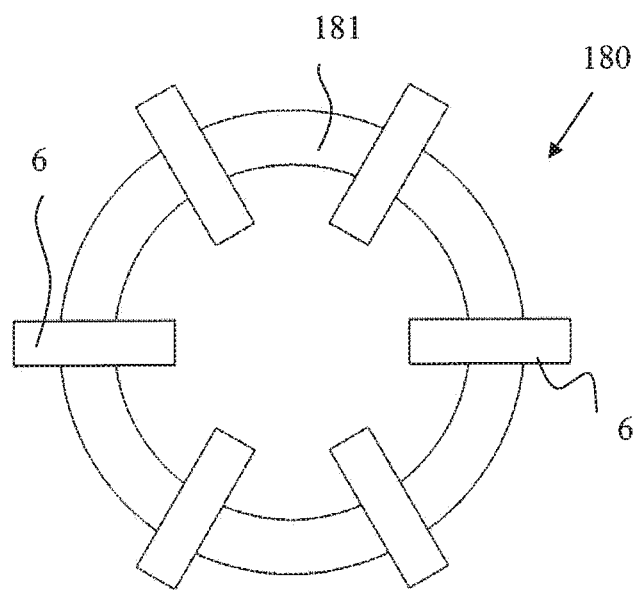
FIG. 8(b) is an end view of this device.
Figure 8C:
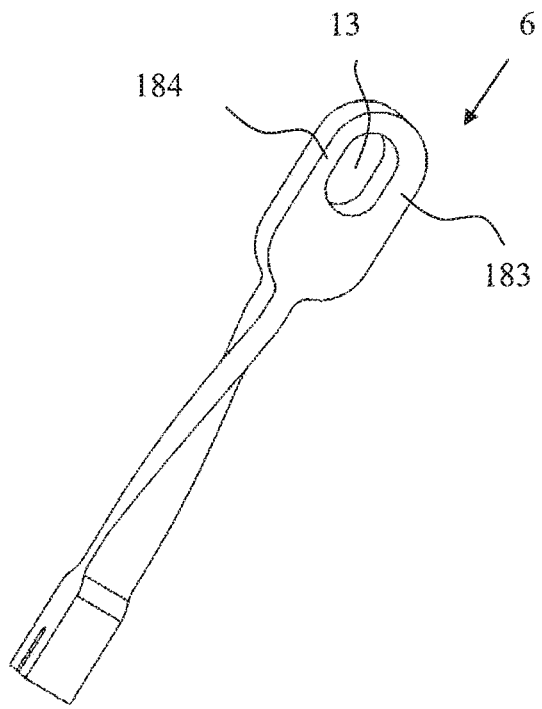
FIGS. 8(c) and 8(d) are isometric views of part of this device.
Figure 8D:
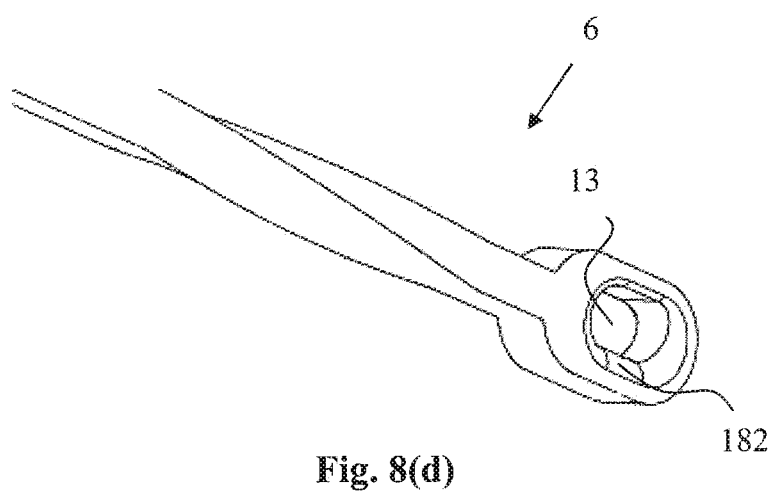
Figures 8E, 8F:
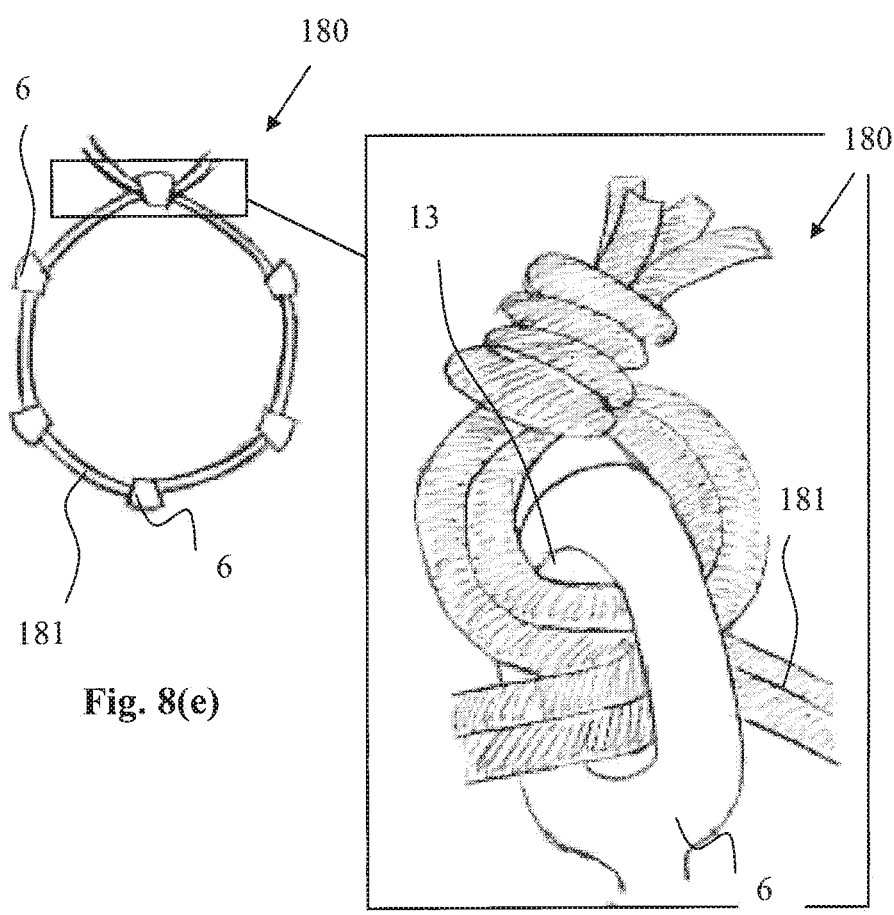
FIG. 8(e) is an end view of this device.

The holder member 10 temporarily holds the filter elements 6 in the capturing position until elapse of the predetermined period of time. Upon elapse of the predetermined period of time the stop element 11 biodegrades/bioabsorbs. This enables the filter elements 6 to move from the capturing position to the open position (FIG. 7). In the open position the device 1 facilitates unrestricted blood flow. The support hoops 3 and 4, and the filter elements 6 remain in the inferior vena cava 2 (FIG. 8). If the holder 10 incorporates a biostable element 12, the biostable element is preferably coupled to one of the filter elements and therefore remains in the vena cava 2.

In FIGS. 8(a) to 8(f) there is illustrated another vascular filter device 180 according to the invention, which is similar to the vascular device 1 of FIGS. 1 to 8, and similar elements in FIGS. 8(a) to 8(f) are assigned the same reference numerals.

In this case in the capturing position each filter element 6 extends in a substantially straight line to the apex 7. Each filter element 6 is twisted through 90 degrees before the apex 7 (FIG. 8(c)).

An opening 13 is provided at the distal and of each of the filter elements 6. The radial dimension of the filter element 6 radially inwardly of the opening 13 is greater than the radial dimension of the filter element 6 radially outwardly of the opening 13 (FIG. 8(c)). In particular the thickness of the wall 183 of the filter element 6 radially inwardly of the opening 13 is greater than the thickness of the wall 184 of the filter element 6 radially outwardly of the opening 13. The radially inward side of the opening 13 has a chamfered edge 182 (FIG. 8(*d*)).

In the capturing position the filter elements 6 are arranged with the openings 13 in the filter elements 6 circumferentially spaced apart in a loop (FIG. 8(*b*)). In the capturing position each opening 13 faces circumferentially.

The holder member comprises two sutures 181 which extend in two loops through the opening 13 in each filter element 6. The sutures 181 engage with each filter element 6 to hold the filter elements 6 in the capturing position. Each suture 181 is biodegradable and/or bioabsorbable upon elapse of the predetermined period of time. All of the suture 181 is biodegradable and/or bioabsorbable. Upon biodegrading/bioabsorbing of the sutures 181, the filter elements 6 are free to move from the capturing position to the open position. The filter elements 6 are not biodegradable or bioabsorbable.

The eyelets 13 are twisted by 90° to achieve a smoother threading path for the monofilament 181 used to tie the filter elements 6.

The eyelets 182 are chamfered/rounded to create a smoother path for any movement of the monofilament 181 and to prevent any damage by mechanical wear. The eyelet hole 13 is offset to ensure that the monofilament 181 moves against the thicker, smoother surface 182. For a given outer eyelet width, an offset opening allows for a larger rounded or chamfered dimension. A larger rounded or chamfered dimension reduces sharpness so that it does not act as a cutting edge.

Two lengths of monofilament 181 are used to secure the filtration elements 6 for extra security. A stopper knot is tied on top of one of the eyelets 13 to further reduce the effect of movement/mechanical wear. This eyelet feature 13 provides an anchor point for the knot on conversion of the device 180.

In FIGS. 9 to 11 there is illustrated another vascular filter device 20 according to the invention. In this case the holder member comprises a ring element 21 extending around the filter elements 22 to hold the filter elements 22 in the capturing position until elapse of the predetermined period of time. The ring element 21 is biodegradable and/or bioabsorbable upon elapse of the predetermined period of time.

The distal end of each filter element 22 comprises a bend (FIG. 11). The angle of each bend is approximately 135 degrees in this case. The bend at the distal end of each filter element 22 acts as a book element to couple the ring element 21 to the filter elements 6 in the capturing position.

During manufacture of the vascular device 20, the ring element 21 is extended around the filter elements 22. The ring element 21 engages with the filter elements 22 to hold the filter elements 22 in the capturing position.

The device 1 consists of the Nitinol™ filter elements 22 and the biodegradable material 21. The circular ring 21 which secures the filter elements 22 is uninterrupted and has a consistent cross-sectional area throughout. Use of the ring 21 decreases production time and eliminates human error and inconsistency when securing the filter elements 6.

To prevent the ring 21 being displaced during physiological movements, the proximal ends of the filter elements 22 are shaped to encircle the ring 21. The ring 21 is applied by initially bringing the filter elements 22 together, as shown in FIG. 9. The ring 21 is placed over the filter elements 22. When the filter elements 22 are no longer detained in place, they will retract towards the filter wall applying tension to the ring 21. To prevent migration of the ring 21 during physiological movements, it is secured by forming the proximal end of the filter elements 22 through heat setting or plastic deformation, as shown in FIGS. 10 and 11.

To assemble, the filter arms 6 are medially brought together, and the ring 21 of degradable material is placed over the elements 6 (FIG. 9). The filter elements 22 are closed in around the ring 21 to prevent ring migration (FIG. 10).

Using the ring 21 may prevent potential long-term failures such as the holder member unraveling and failure due to excessive tightening of the holder member. The ring 21 provides consistency between manufactured units of the device 20 by eliminating operator variation associated with knot tying. More than one ring may be used to increase the force required to break the holder, this will lengthen the time to failure and also act as a safety feature in the event that one ring is damaged.

Figure 12:
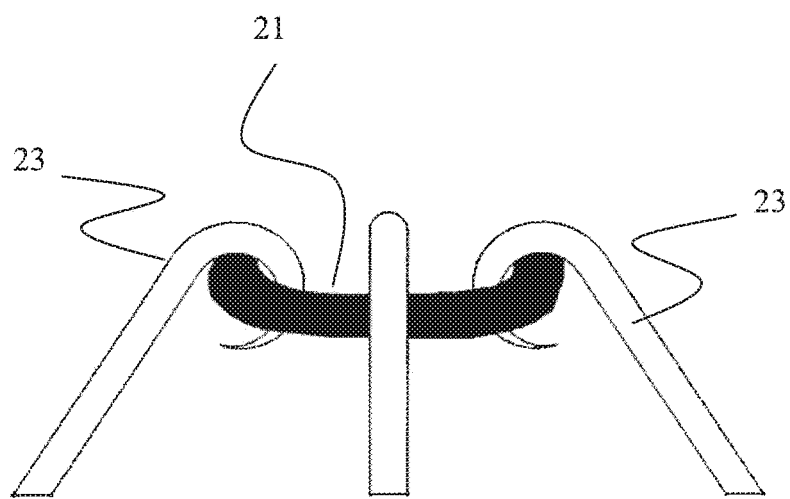
FIG. 12 is a view similar to FIG. 11 of another vascular filter device according to the invention.

An alternative embodiment is shown in FIG. 12 where the ring 21 is applied inside filter elements 23 from underneath.

FIGS. 13 to 16 illustrate a further vascular device 30 according to the invention. The device 30 has filter elements 31 with a radially-directed slot or notch 32 at a bend in the filter elements 31, the angle of each bend being approximately 90°.

Figure 15:
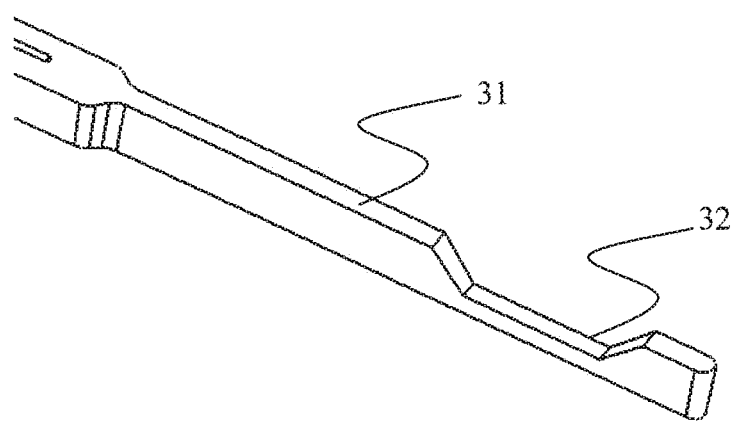

A possible method of manufacturing the device 30 includes machining the notch 32 in at the distal end of the filter element 31 as shown in FIG. 15. The tip of the filter arm 31 is then heat-set in a shape similar to that shown in FIG. 16. The filter element arms 6 can then be constrained together in a filtering position using the polymeric O-ring 33 as shown in FIG. 13.

Figure 14:
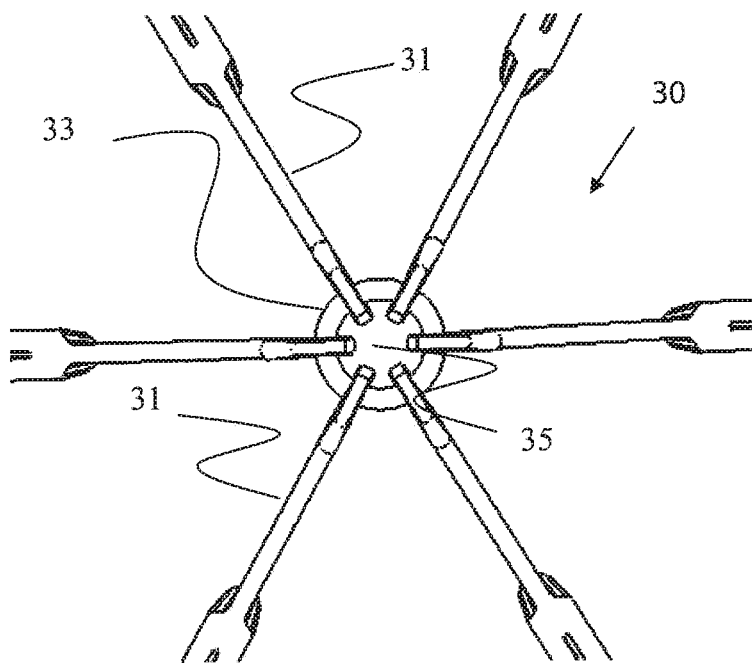
FIG. 14 is an end view of the device of FIG. 13, FIGS. 15 and 16 are isometric views of part of the device of FIG. 13 during manufacture.

Manufacture of the device 30 using the O-ring 33 is easy, rapid and repeatable. Using the O-ring 32 allows for easy control of the diameter of the lumen which is at the tips of the filter elements 31 on the device 30, as shown in FIG. 14. This lumen allows for flow of blood to pass through the apex 35 of the device 30 and avoids generating an area of stagnation within the device 30 in this region.

Figure 13:
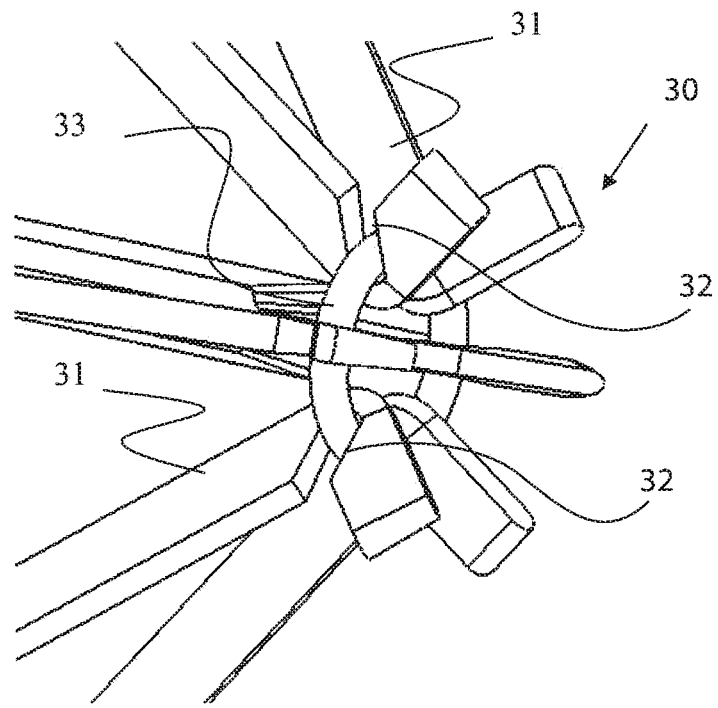
FIG. 13 is a perspective view similar of a holder member of another vascular filter device according to the invention.
Figure 16:
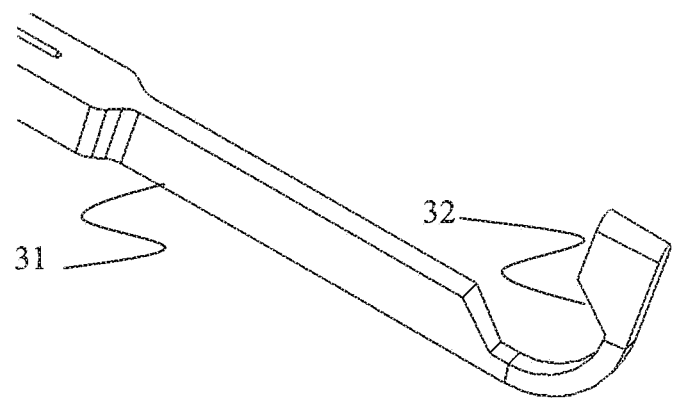
Figure 17:
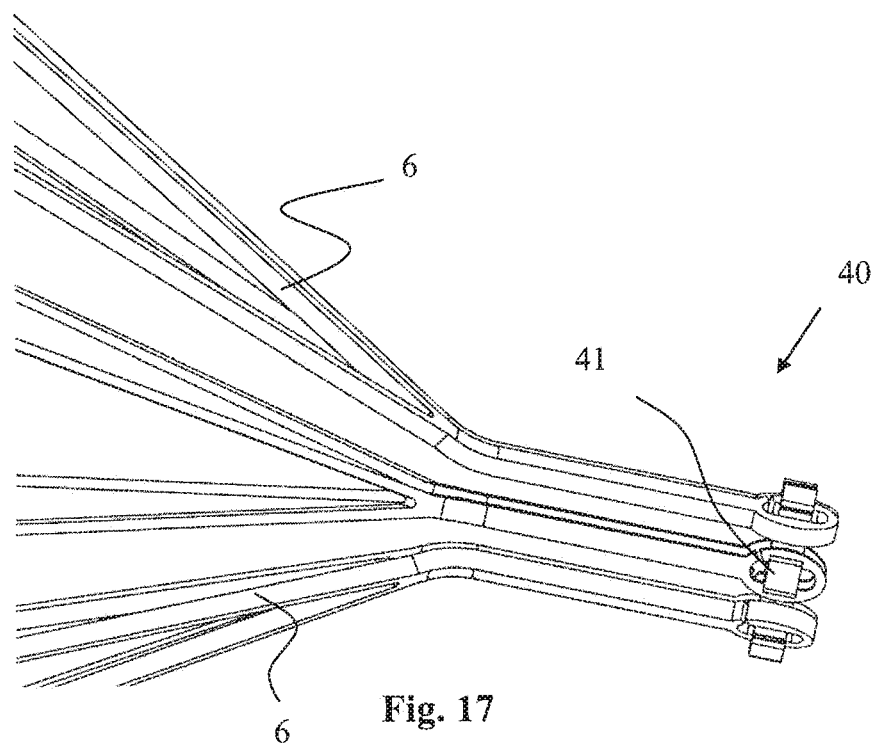
FIG. 17 is a perspective view of another vascular filter device according to the invention.
Figure 18:
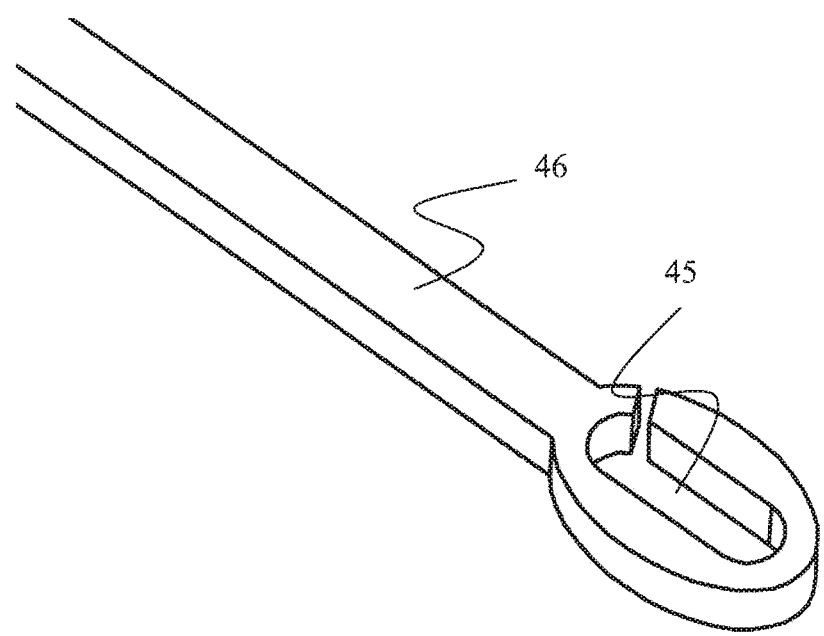
FIG. 18 is an isometric view of part of the device of FIG. 17.
Figure 19:
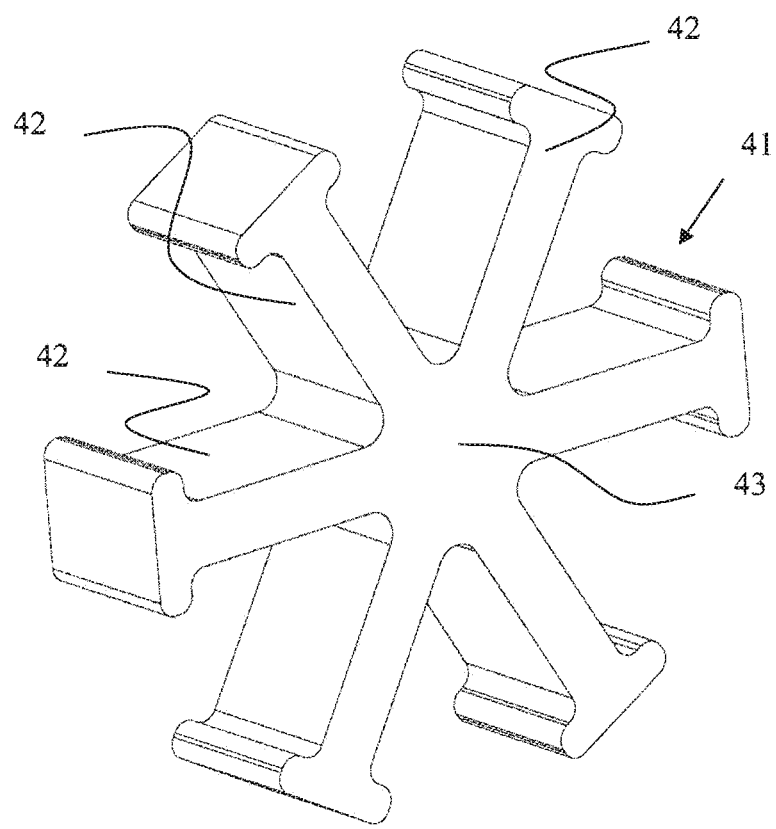
FIG. 19 is an isometric view of another part of this device.

FIG. 13 illustrates the degradable retaining ring 33 in place, FIG. 14 illustrates an end view of the device 30 showing the lumen at the apex 35, FIG. 15 illustrates the strut with the notch created, and FIG. 16 illustrates the strut heat-set into position.

Referring to FIGS. 17 to 20 there is illustrated another vascular filter device 40 according to the invention. In this case a holder member 41 comprises six arms 42. The six arms 42 are connected together at a central connection point 43. Each arm 42 extends radially from the connection point 43 through an opening 45 in a filter element 46. Each arm 42 engages with a filter element 46 to hold the filter elements 46 in the capturing position.

The holder member 41 is biodegradable and/or bioabsorbable upon elapse of the predetermined period of time. Upon biodegrading/bioabsorbing of the holder member 41, the filter elements 46 are free to move from the capturing position to the open position.

The moulded biodegradable component 41 is in the form of a snow-flake and may be incorporated to restrain the filter elements 46.

The eyelets 45 at the distal ends in their heat-set form are provided as a closed 'C'-shape. The eyelet 45 is then chilled below the Mf temperature and mechanically spread to open the eyelet 45 wider. The moulded component 41 is inserted and the opened eyelet 45 is closed through application of heat to secure the moulded component 41 to the eyelets 45.

Figure 20:
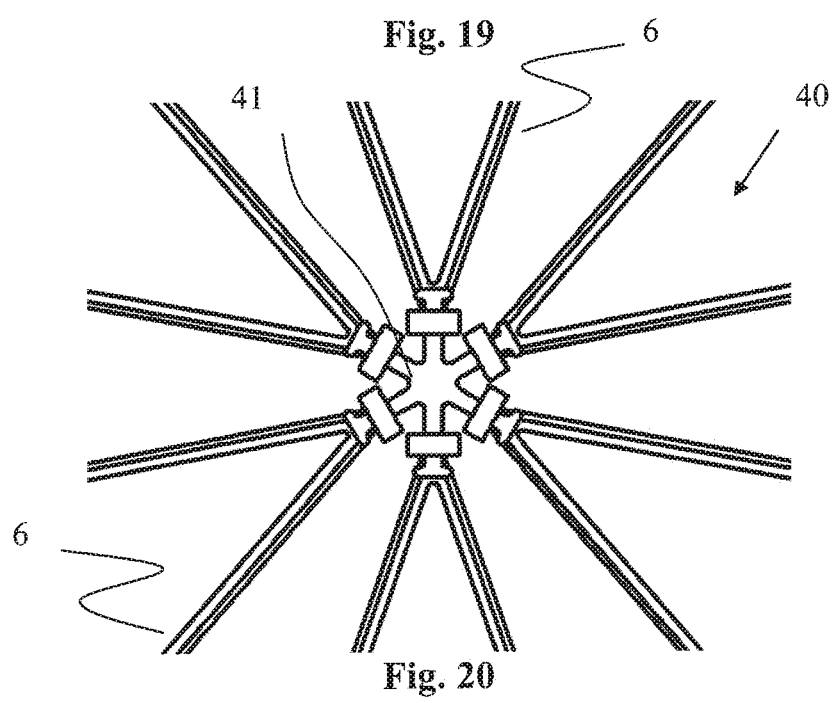
FIG. 20 is an end view of this device.
Figure 20A:
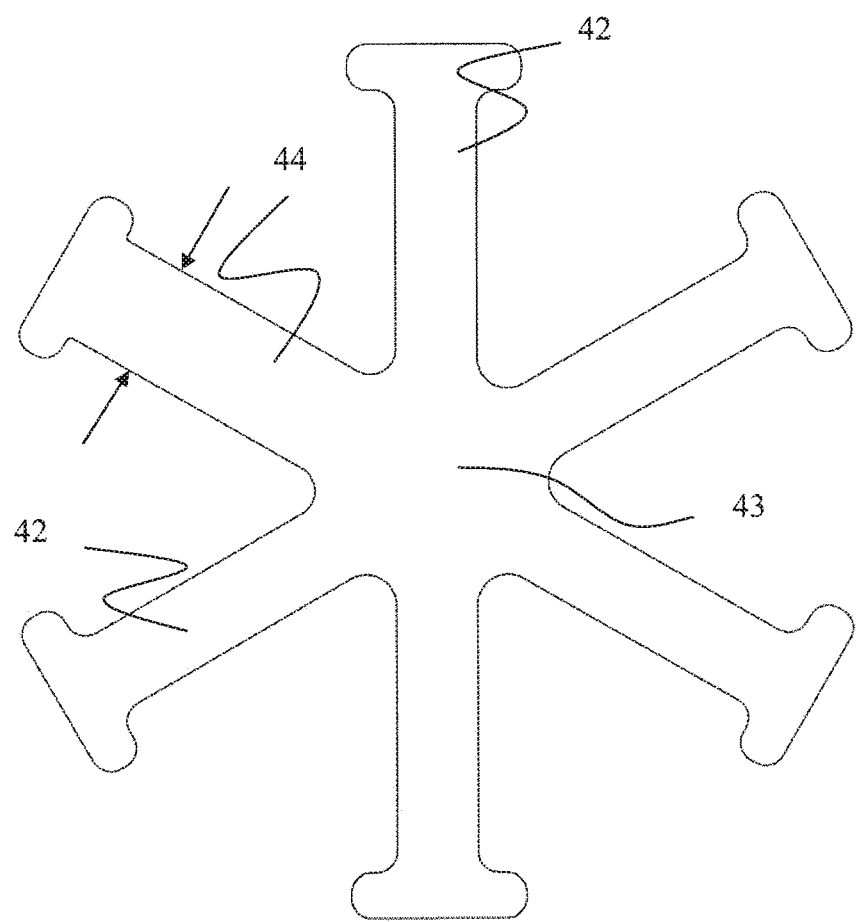
FIG. 20(a) is an end view of part of another vascular filter device according to the invention.

As illustrated in FIG. 20(*a*), the holder member may be provided with one wider strut 44. The wider strut 44 having an increased tensile strength will fail post failure of the other five thinner struts 42. As each of the thinner struts 42 fails, the T-shaped head and failed strut portion are carried to the vessel wall by the eyelet 13 where it becomes endotheliased. The eyelet 45 holding the wider strut 44 carries the remaining material to the vessel wall where it becomes endotheliased thus preventing it from becoming an embolus. Ideally, the holder member has a strut for each eyelet.

Figure 21:
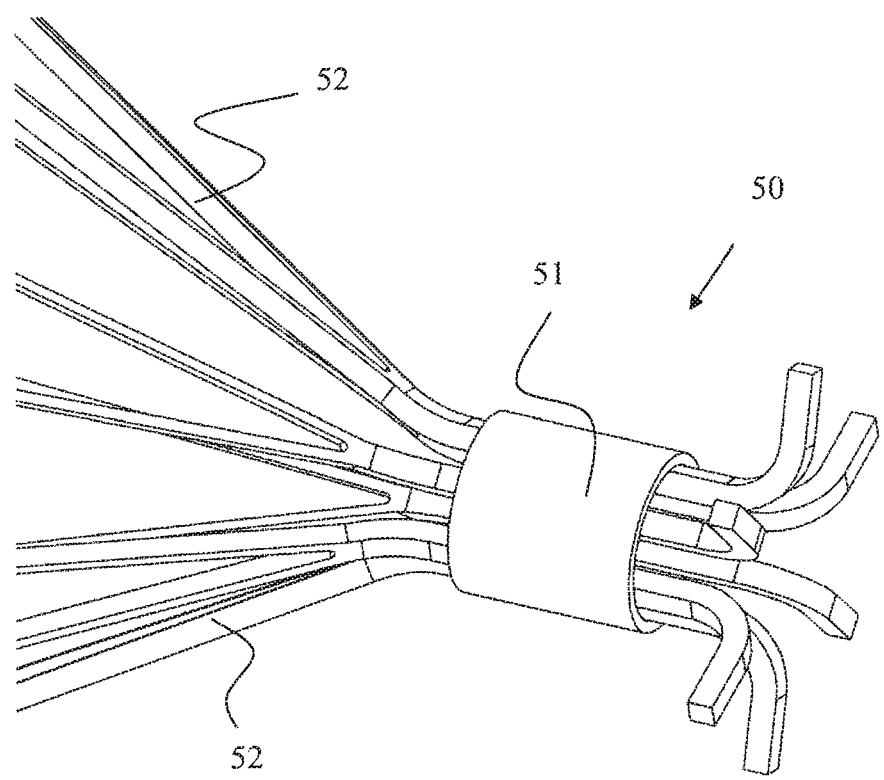
FIG. 21 is a perspective view of a holder arrangement of another vascular filter device according to the invention.
Figure 22:
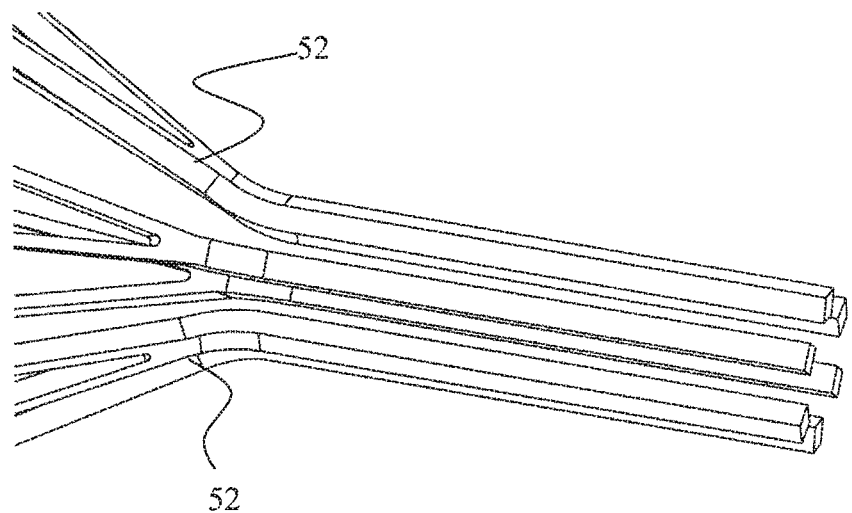
FIGS. 22 and 23 are isometric views of parts of this device during manufacture.
Figure 23:
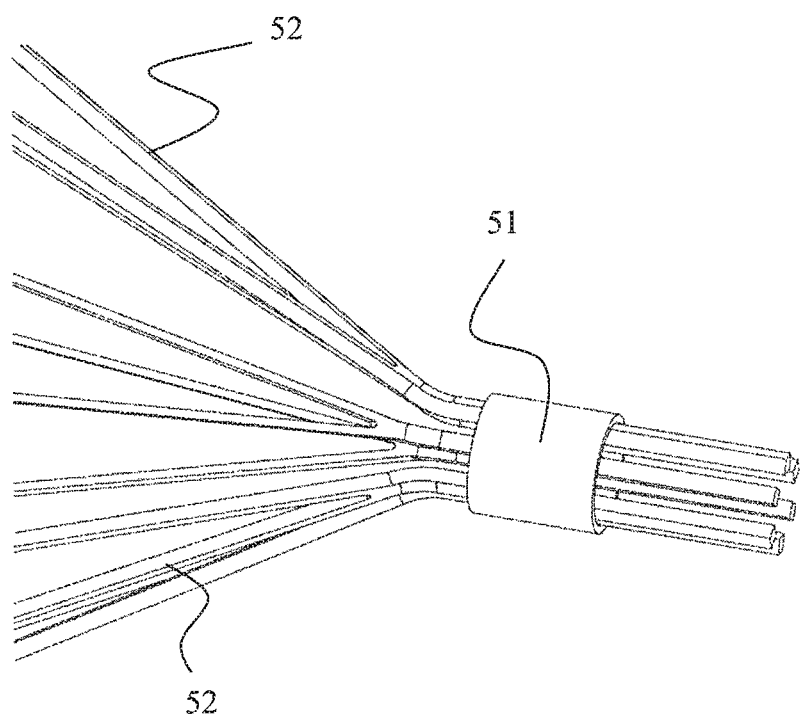

In FIGS. 21 to 23 there is illustrated another vascular device 50 according to the invention. In this case a holder member comprises a tube element 51 extending around the filter elements 52 to hold the filter elements 52 in the capturing position until elapse of the predetermined period of time. The tube element 51 is located proximally of the distal end of the filter elements 52. The tube element 51 is biodegradable and/or bioabsorbable upon elapse of the predetermined period of time.

The distal end of each filter element 52 comprises a bend. The angle of each bend is approximately 90° in this case. The bend at the distal end of each filter element 52 acts as a hook element to couple the tube element 51 to the filter elements 52 in the capturing position.

The biodegradable cap 51 is threaded over the apex region of the filter elements 52 (FIG. 23). Once in position, the ends of the filter elements 52 are formed to hold the cap 51 in place. Alternatively, the ends of the filter elements are preformed to hold the cap in place and are straightened mechanically to fit the cap 51. The cap 51 enables simultaneous opening upon conversion.

Other tubular cross sections or an O-ring may be used in place of the cap 51.

Figure 24:
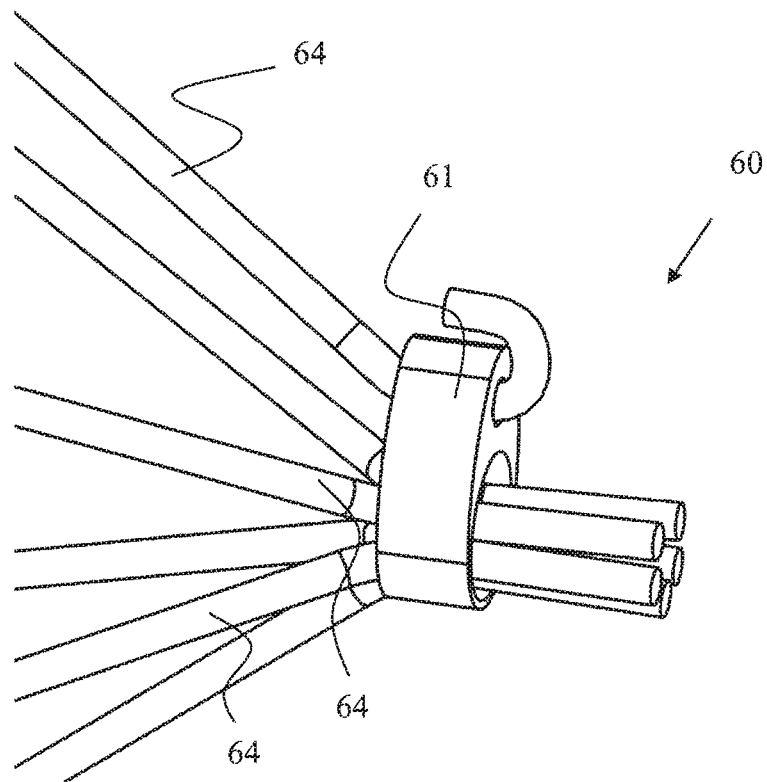
FIG. 24 is a perspective view of the holder arrangement of another vascular filter device of the invention.
Figure 25:
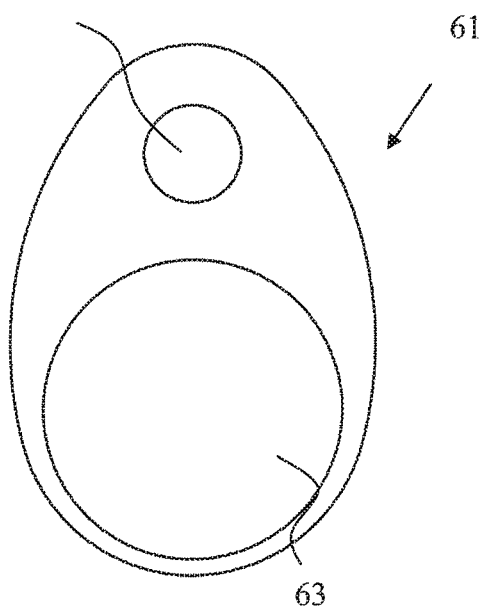
FIG. 25 is an end view of part of this device.

FIGS. 24 and 25 illustrate a further vascular filter device 60 according to the invention. In this case the holder member comprises a tube element 61 extending around the filter elements 6 to hold the filter elements 6 in the capturing position until elapse of the predetermined period of time. The tube element 61 comprises a first opening 62 through which one filter element 64 extends in the capturing position, and a second opening 63 through which all of the other filter elements 6 extend in the capturing position.

The distal end of the filter element 64 comprises a bend. The angle of the bend is approximately 135 degrees in this case. The bend at the distal end of the filter element 64 acts as a hook element to couple the tube element 61 to the filter element 64 in the capturing position.

The tube element 61 is biodegradable and/or bioabsorbable upon elapse of the predetermined period of time. The wall thickness of the tube element 61 around the first opening 62 is greater than the wall thickness of the tube element 61 around the second opening 63. In this manner the thinned wall acts as a predetermined failure point. Upon biodegrading/bioabsorbing of the tube element 61, the tube element 61 will fail around the second opening 63.

Because the tube element 61 does not fail around the first opening 62, the filter element 64 extends through the first opening 62 in the open position. The bend at the distal end of the filter element 64 acts as a hook element to couple the tube element 61 to the filter element 64 in the open position.

The multi-lumen cap 61 has the two lumens: the small lumen 62 to house the filter element 64 or a pair of filter elements surrounded by a large wall thickness, and the large lumen 63 to house the remainder of the filter elements 64 surrounded by a thin wall thickness.

The tube element 61 has a reduced tensile strength at the failure point. The thin wall has the reduced tensile strength, providing the predetermined failure point. The filter elements 6 extending through the large lumen 63 break the thin wall after the predetermined period of time and revert to the vessel wall. The filter element 64 extending through the small lumen 62 carries the cap 61 to the vessel wall where it is bioresorbed thus preventing it from becoming an embolus.

The ending extending through the small lumen 62 is provided with a feature to prevent the cap 61 from dislodging during use. This may be achieved in a number of methods such as forming, bonding, overmoulding, crimping. Features may be provided to secure the remainder of the endings in the large lumen 63.

The multilumen cap 61 enables simultaneous opening upon conversion.

Figure 26:
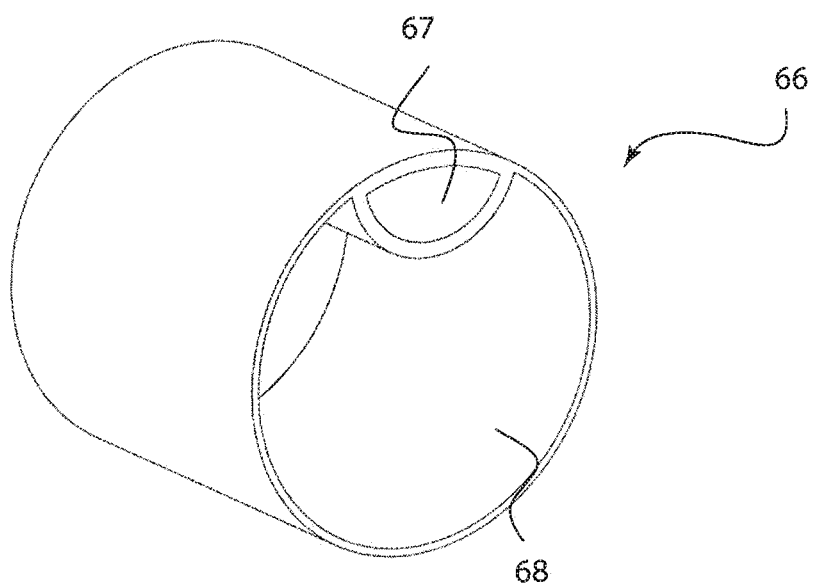
FIG. 26 is an isometric view of part of another vascular filter device of the invention.

It will be appreciated that a variety of types of multilumen form may be used, as illustrated in FIG. 26. This drawing shows a cylindrical holder element 66 having a small lumen 67 formed by a curved wall, the remainder of the inside of the element 66 being the large lumen.

More than two lumens may be used. For example, three lumens are provided radially in-line, the central lumen having a thinner wall than the outer lumens on either side. Radially opposing filter elements extend through the outer lumens and are secured, the remaining filter elements extending through the central lumen where they may be temporarily secured. The thin wall of the central lumen degrades first allowing the radially opposing filter elements to break the holder member into two halves, each halve being secured to the opposing filter elements post conversion at the vessel wall where biodegradation is completed.

Figure 27:
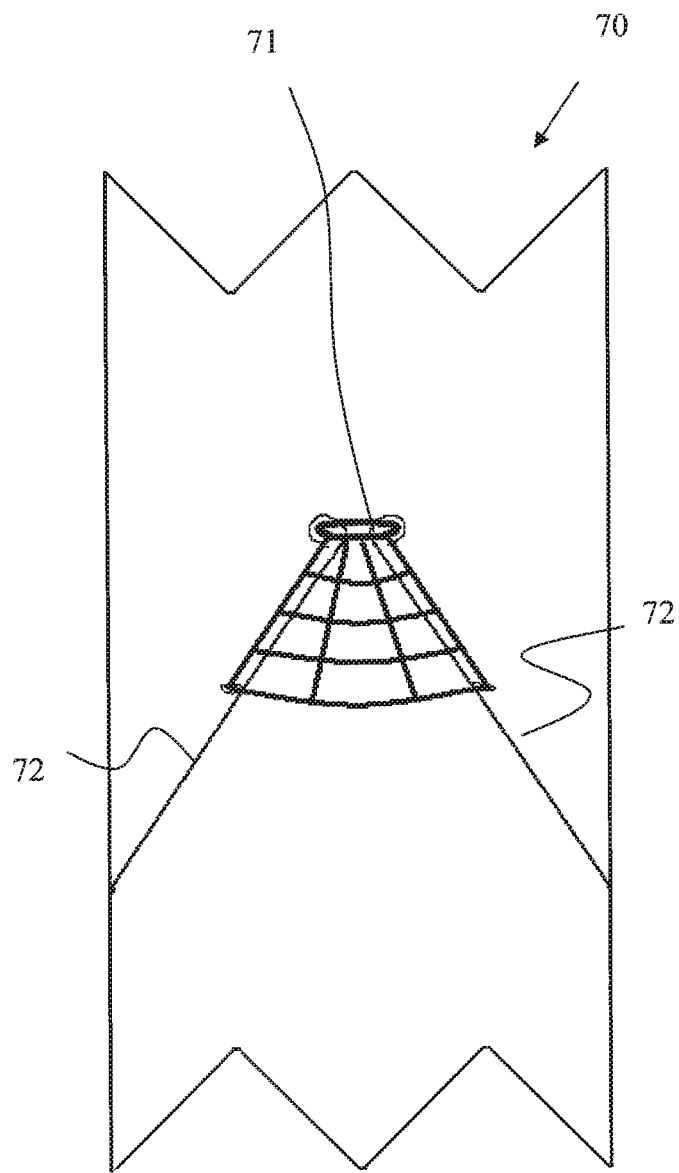
FIG. 27 is an isometric view of another vascular filter device of the invention.
Figure 28:
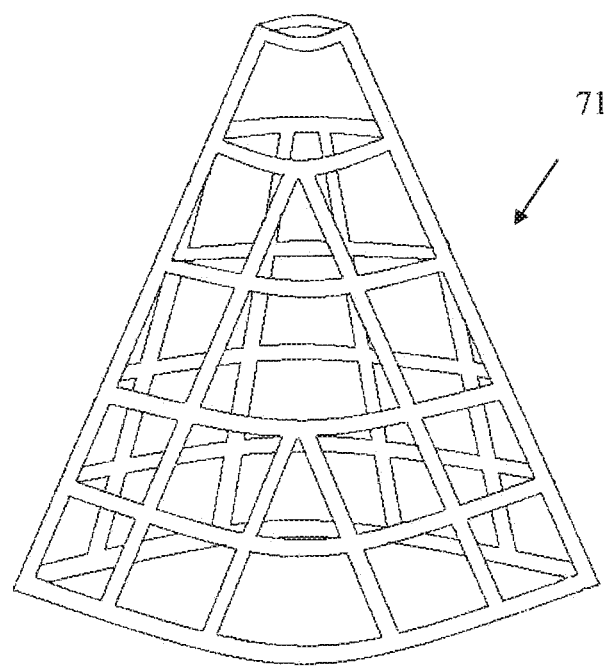
FIG. 28 is an isometric view of part of this device.
Figure 29:
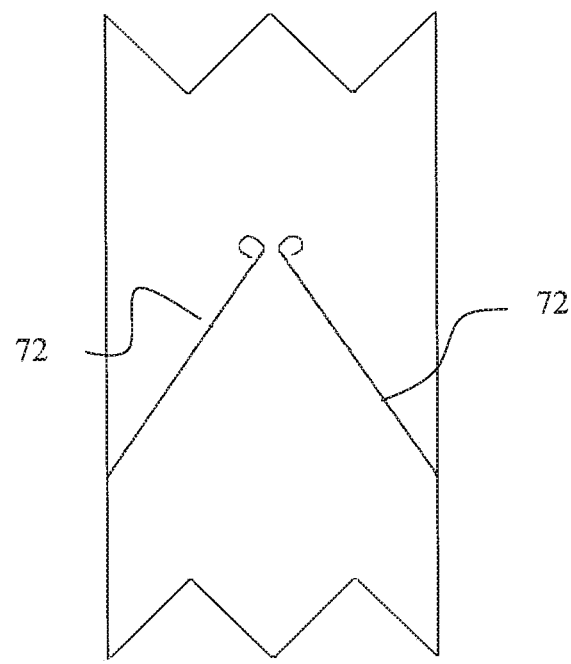
FIG. 29 is a side view of another part of this device.

Referring to FIGS. 27 to 29 there is illustrated another vascular filter device 70 according to the invention. In this case the holder member comprises a conically shaped tube element 71 extending around the filter elements 72 to hold the filter elements 72 in the capturing position until elapse of the predetermined period of time. The tube element 71 comprises a mesh and is biodegradable and/or bioabsorbable upon elapse of the predetermined period of time.

The distal end of each filter element 72 comprises a bend which acts as a hook to couple the tube element 71 to the filter elements 72 in the capturing position.

The filter elements 72 are of Nitinol™ and the holder 71 is of biodegradable material in the configuration of a profiled sheath to secure the filter elements 72. The sheath 71 comprises a mesh with a tapered thickness, decreasing from proximal to distal, so that the holder degrades radially inwardly to minimise the torque at the formed filter element ends. Use of the sheath 71 decreases production time and eliminates human error and inconsistency when securing the filter elements 72. Should any of the mesh struts fail, the structural integrity of the sheath 71 is not compromised as there are numerous other mesh struts to withstand the radial load.

To prevent the sheath 71 becoming displaced during physiological movements, the distal ends of the filter elements 72 are shaped to encircle the sheath 71.

The sheath 71 is applied by initially bringing the filter elements 72 together medially, as shown in FIG. 29. The sheath 71 is then placed over the filter elements 72. When the filter elements 72 are no longer detained in place, they will retract towards the filter wall applying tension to the sheath 72. To prevent migration of the sheath 72 during physiological movements, the distal end of the eyelets are closed in to secure the sheath 71, as shown in FIG. 27. If the filter element ends are pre-formed to encircle distal end of the sheath, they must be straightened temporarily before the sheath is fitted. The proximal end of the sheath 71 may also be secured to one or more of the filter arms 72 in the open configuration.

Using the sheath 71 may prevent potential long-term failures. The sheath 71 provides consistency between manufactured units of the device 70 by eliminating operator variation associated with knot tying. The multi-strut mesh architecture ensures maximum structural integrity.

In FIGS. 30 to 34 there is illustrated another vascular filter device 80 according to the invention. In this case the holder comprises a rigid pin element 81. The upper and of the pin element 81 is disconnected from the lower end of the pin element 81. The pin element 81 comprises an elongate central element 83, an upper stop element 84, and a lower stop element 82. The lower stop element 82 is formed separately to the central element 83. The upper stop element 84 is formed separately to the central element 83.

Figure 30:
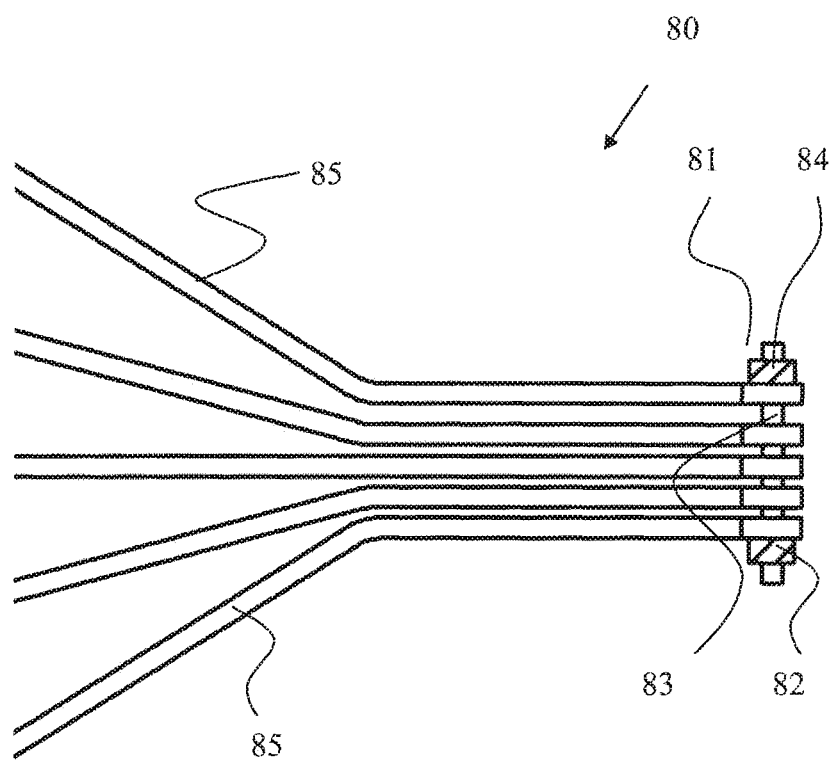
FIG. 30 is a side view of part of another vascular filter device of the invention.

In the capturing position the filter elements 85 are arranged with the openings 86 in the filter elements 85 aligned radially in a straight line (FIG. 30). As illustrated in FIGS. 31 to 34, a portion of the wall of the filter element 85 extends around the full circumference of each opening 86 to define the opening 86.

The longitudinal axis of the pin element 81 is straight. The central element 83 extends in a straight line through the opening 86 in each filter element 85 with the upper stop element 84 at the upper end of the central element 83 externally of the openings 86, and the lower stop element 82 at the lower end of the central element 83 externally of the openings 86.

In the capturing position the upper stop element 84 engages with the upper filter element 85 externally of the opening 86, and the lower stop element 82 engages with the lower filter element 85 externally of the opening 86. In this manner the filter elements 85 are held in the capturing position.

The central element 83 is biostable, and the stop elements 84, 82 are biodegradable and/or bioabsorbable upon elapse of the predetermined period of time. Upon biodegrading/bioabsorbing of the stop elements 84, 82, the filter elements 85 are free to move from the capturing position to the open position.

The two stops 84, 82 may be biostable if a biodegradable pin 83 is used. It is appreciated that only one component needs to be biodegradable. Alternatively, the two stops 84, 82, and the pin 83 can be biodegradable.

During manufacture of the vascular device 80, each stop element 84, 82 is attached to the central element 83. Attachment of the secondary holder member 84, 82 to the pin 83 may be through crimping, or bonding, or overmoulding, or a mechanical snap fit, or a screw thread, or solvent bonding.

Figure 31:
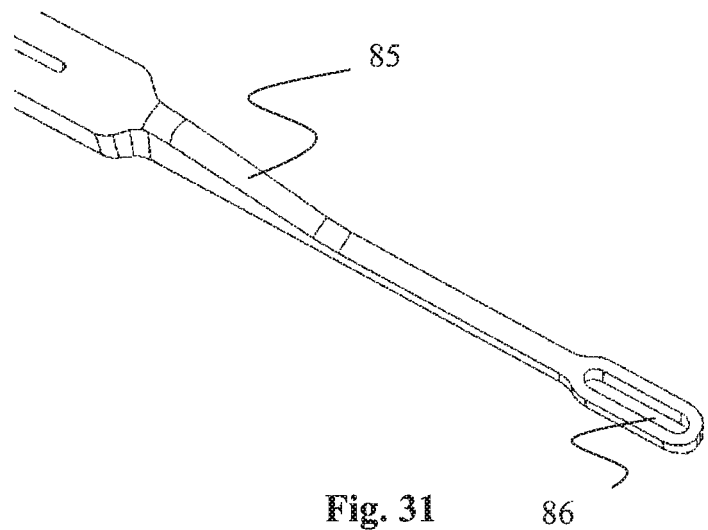
FIGS. 31 to 34 are isometric views of parts of this device during manufacture.
Figure 32:
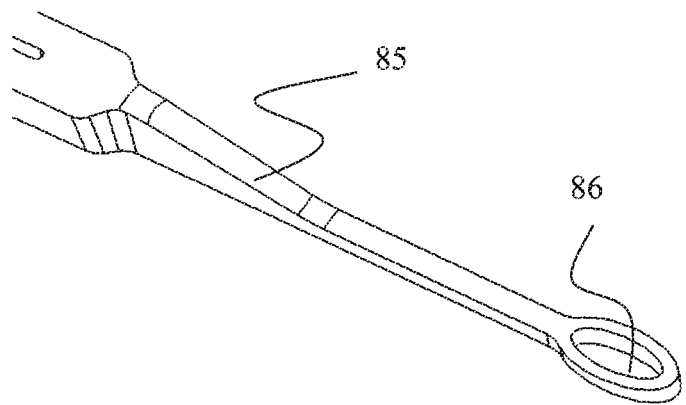
Figure 33:
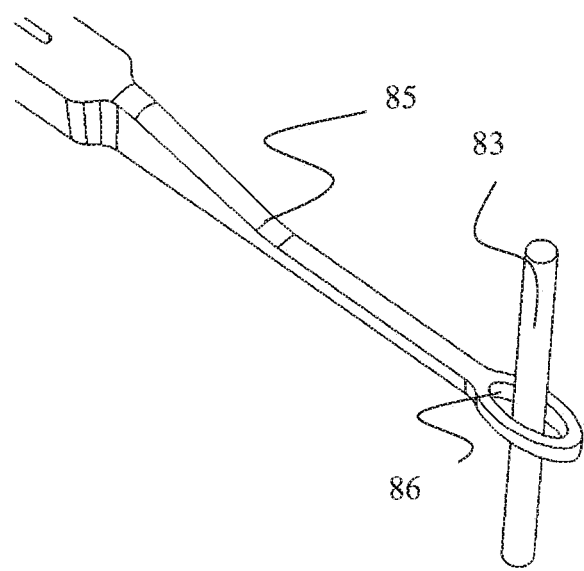

A possible method of attaching the central element 83 within an eyelet 86 of the device 80 is illustrated in FIGS. 31 to 34. The long slender eyelet 86 is formed as shown in FIG. 31. The eyelet 86 in the heat-set shape is narrower than the central element 83 that is being attached to the eyelet 86. The eyelet 86 is chilled below the Mf temperature and mechanically spread to open the eyelet 86 wider, making it closer to a circular opening as shown in FIG. 32. The central element 83 is positioned within the eyelet 86 as shown in FIG. 33. The eyelet 86 is heated above its Af temperature so that the eyelet 86 retakes its memory shape. As the eyelet 86 returns to its memory shape it will form an interference fit between the eyelet 86 and the central element 83 positioned within the eyelet 86. Alternatively, the openings are machined wide and are crimped onto the central element 83 to secure the filter elements in the capturing position.

Figure 34:
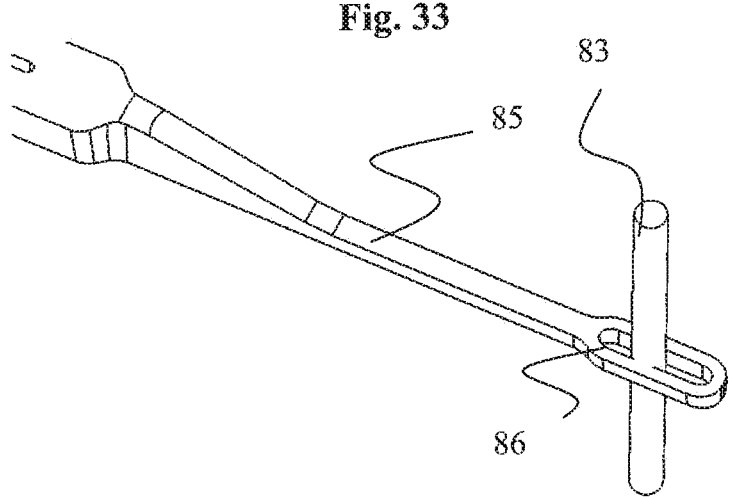
Figure 34A:
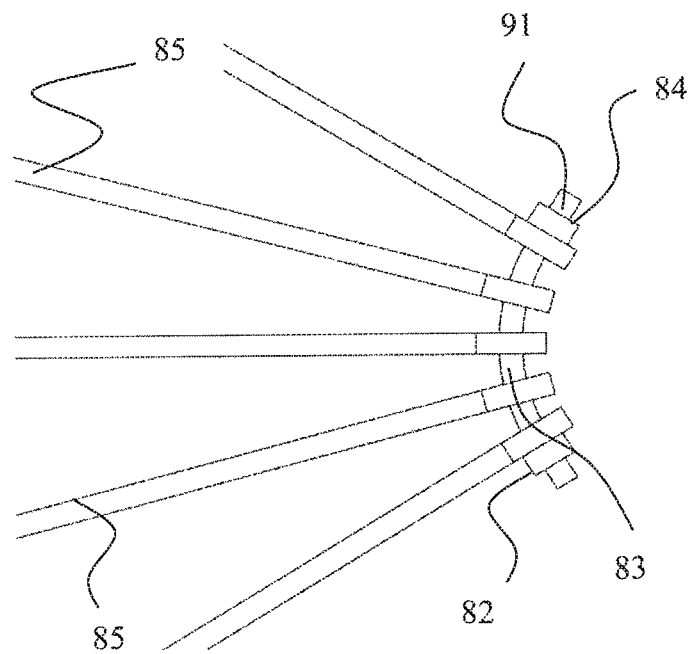
FIG. 34(a) is a view similar to FIG. 30 of another vascular filter device of the invention.
Figure 34B:
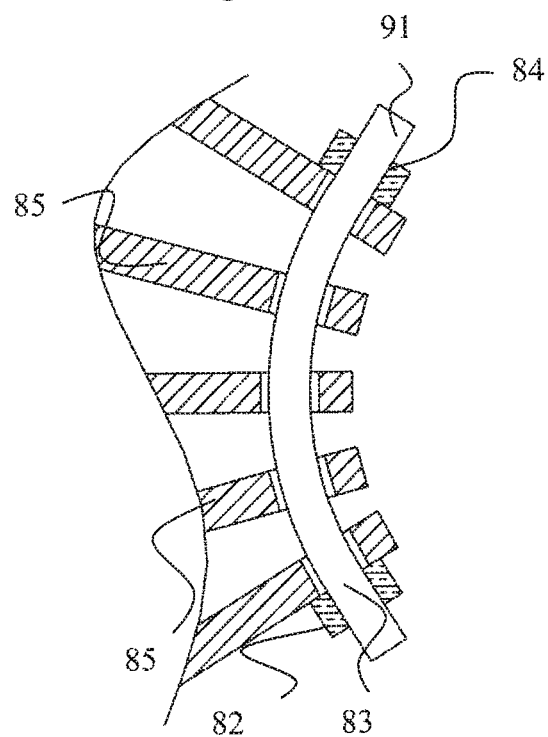
FIG. 34(b) is an enlarged side view of part of this device.

It will be appreciated that the pin element 81 may be flexible as illustrated by a pin element 91 in FIGS. 34(a) and 34(b).

The eyelets 86 of the filter elements 85 may be arranged to apply a bend to the straight pin 81. In this case the pin 81 has enough flexibility to bend. Alternatively, the pin 81 may be moulded with the curvature preset.

Figure 35:
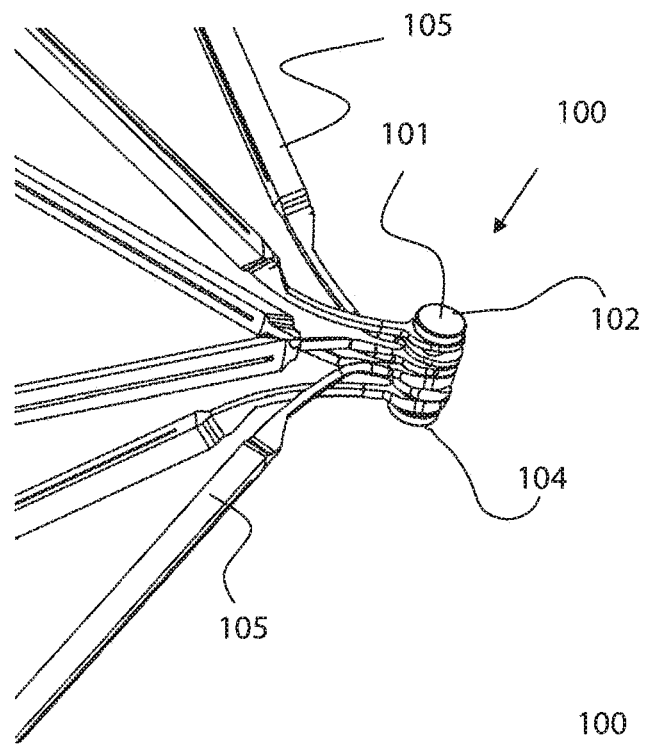
FIG. 35 is a perspective view of another vascular filter device of the invention.
Figure 36:
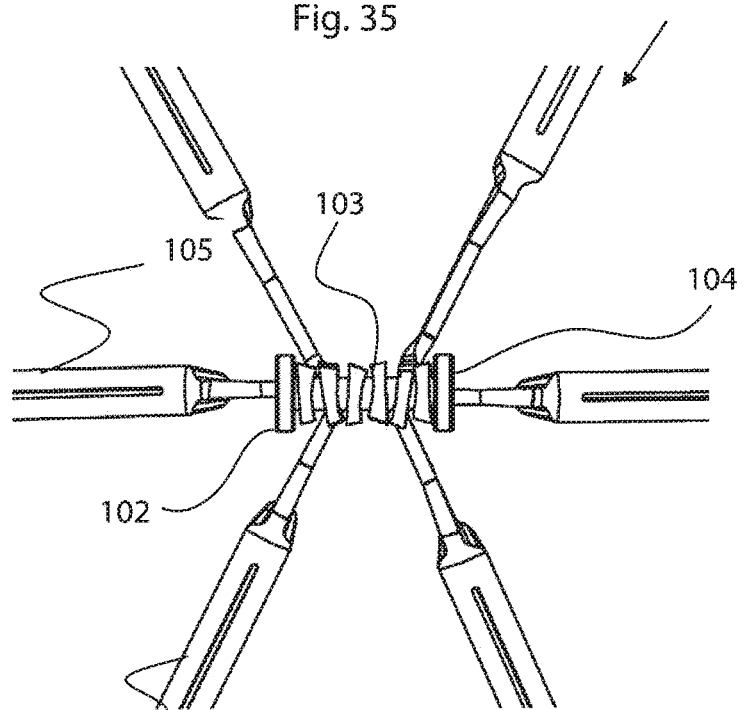
FIG. 36 is an end view of part of this device.

Referring to FIGS. 35 and 36 there is illustrated another vascular device 100 according to the invention. The device 100 comprises filter elements 105 with eyelets 106. In this case a first stop element 102 is formed integrally with a central element 103. A second stop element 104 is formed separately to the central element 103.

The central element 103 and the first stop element 102 are biostable, and the second stop element 104 is biodegradable and/or bioabsorbable upon elapse of the predetermined period of time. Upon biodegrading/bioabsorbing of the second stop element 104, the filter elements 105 are free to move from the capturing position to the open position.

During manufacture of the vascular device 100, the pin element is deformed to form the central element 103 and the first stop element 102.

Either end of the pin may be formed to secure the filter elements 105 in the capturing position, for example through mechanical methods to achieve a dumbbell shape or rivet, through heat, or with a solvent.

The pin element provides a rigid holder member for longer term filtration for example approximately 4 to 24 months until degradation. It may be a moulded piece.

An opening 106 in the end of each capture member 105 is aligned to allow insertion of the pin with the integral cap. Once the pin is in place, the end with no cap is secured with the biodegradable stop. When deployed, the filter elements 105 are retained in the filtering position. After a certain period of time, the biodegradable stop 104 weakens to a failure mode where the radial force of the filter elements 105 overcomes the coupling force between the pin central element 103 and the stop 104.

The pin may be manufactured from a biostable flexible or rigid material. In this case, the biodegradable stop 104 weakens and the filter elements 105 revert to their radially biased position at the vessel wall. The opening 106 in the filter element 105, traps the pin against the vessel wall where it becomes endothelised.

Alternatively the stop may be manufactured from a biostable material, in which case the pin would be biodegradable.

Figure 37:
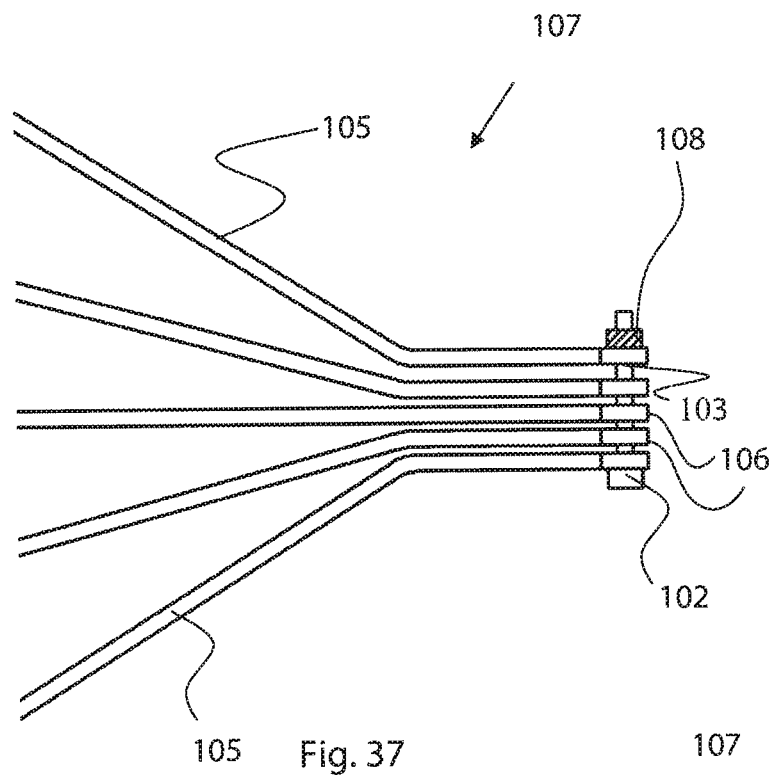
FIG. 37 is a side view of part of this device.
Figure 38:
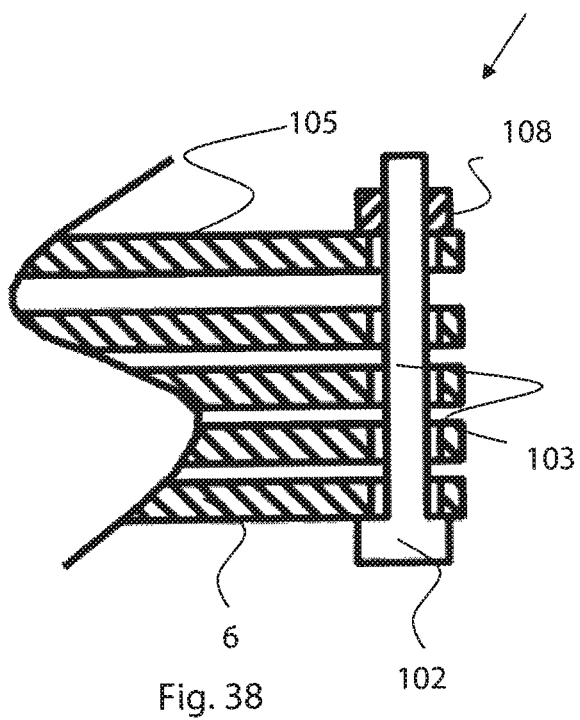
FIG. 38 is an enlarged, cross-sectional side view of part of this device.

Using the pin 101 allows simultaneous opening of the filter elements 105. FIGS. 37 and 38 show a variation, in which like parts are assigned the same reference numerals. In this case a stop element 108 is positioned onto the pin central element 103 which extends past the stop element.

Figure 38A:
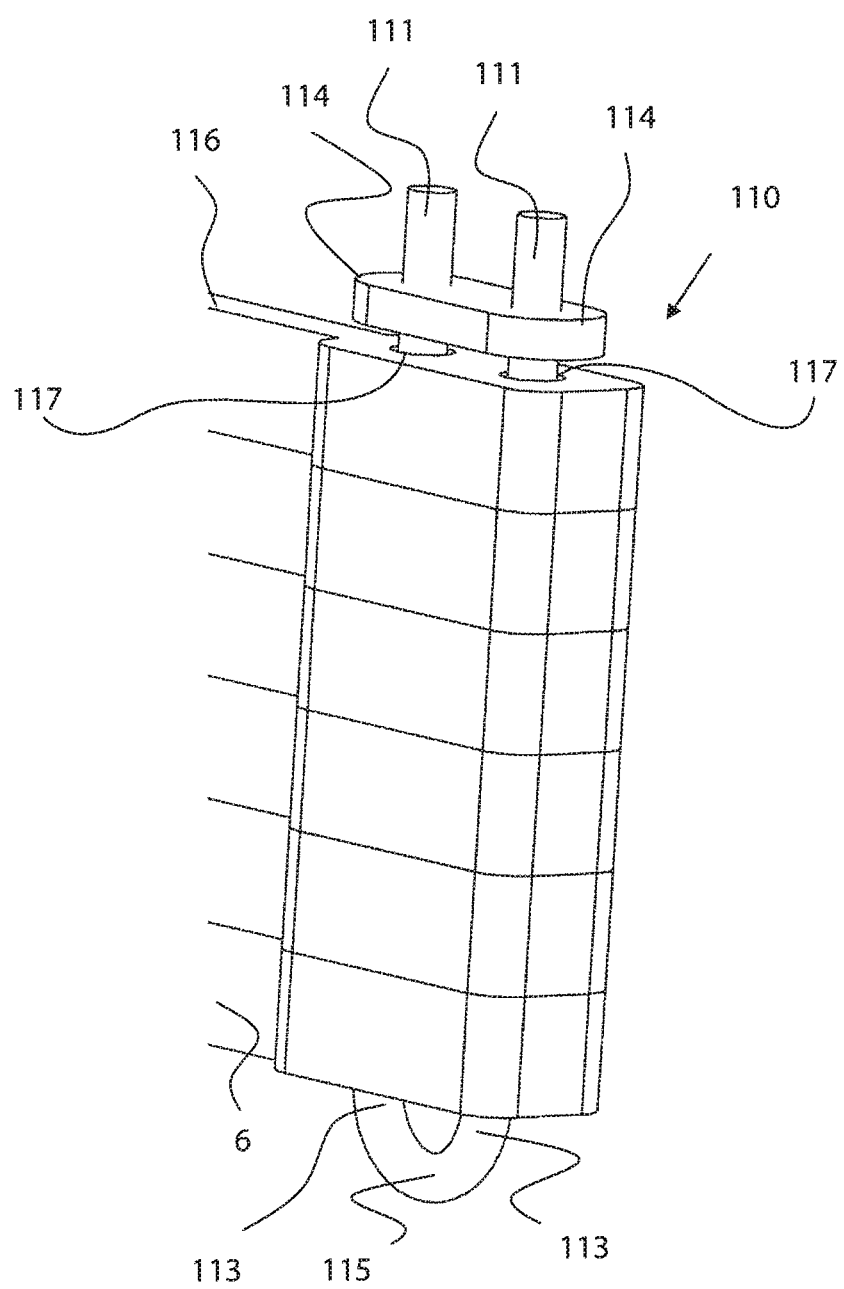
FIG. 38(a) is a perspective view of another vascular filter device of the invention.

In FIG. 38(a) there is illustrated another vascular device 110 according to the invention. In this case a holder member comprises two rigid pin elements 111. The upper end of each pin element 111 is disconnected from the lower end of each pin element 111. Each pin element 111 comprises an elongate central element 113, an upper stop element 114, and a lower stop element. Each upper stop element 114 is formed separately to each central element 113. The first upper stop element 114 is formed integrally with the second upper stop element 114.

The lower end of the first central element 113 is connected to the lower end of the second central element 113 in a loop 115. The first central element 113 is formed integrally with the second central element 113. By connecting together the lower ends of the two central elements 113 in the loop 115, this loop 115 acts as a lower stop element for each pin element 111.

Two openings 117 are provided at the distal end of each of the filter elements 116. Each central element 113 extends in a straight line through an opening 117 in each filter element 116.

In the capturing position each upper stop element 114 engages with the upper filter element 116 externally of the openings 117, and the lower stop loop 115 engages with the lower filter element 116 externally of the openings 117. In this manner the filter elements 116 are held in the capturing position.

The central element 113 is biostable, and the upper stop elements 114 are biodegradable and/or bioabsorbable upon elapse of the predetermined period of time. Upon biodegrading/bioabsorbing of the upper stop elements 114, the filter elements 116 are free to move from the capturing position to the open position.

The biostable/biodegradable wires 113 are threaded through the two slots 117 so that the upper ends of the wires 113 are aligned. The aligned endings are secured by overmoulding the biodegradable securing features 114.

Figure 38B:
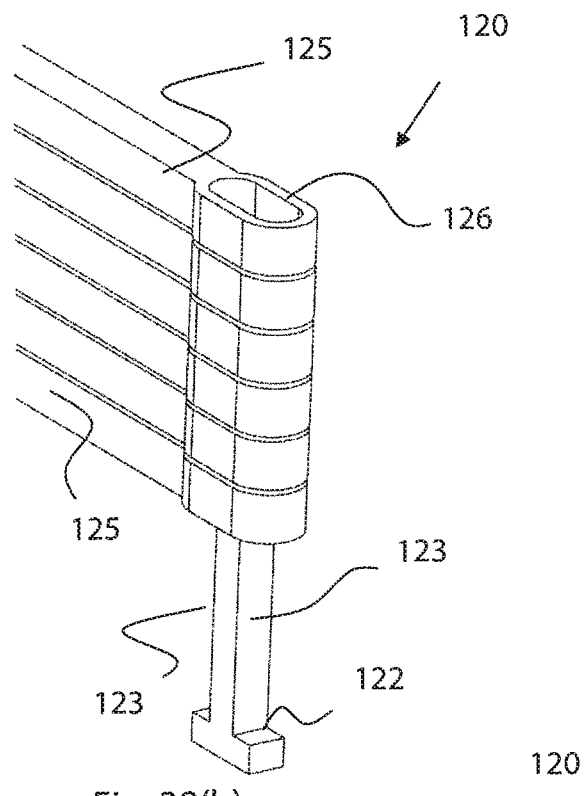
FIGS. 38(b) to 38(e) are isometric views illustrating manufacture of another vascular filter device according to the invention.
Figure 38C:
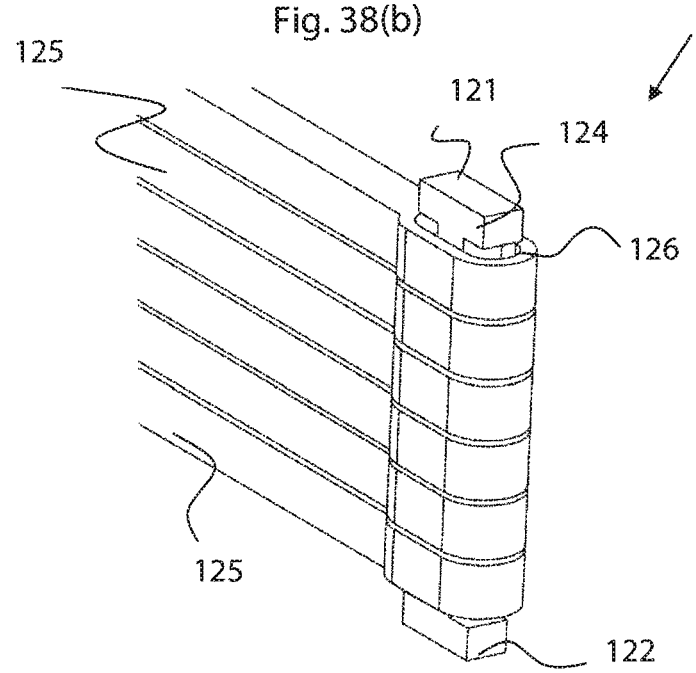

FIGS. 38(b) to 38(c) illustrate a further vascular filter device 120 according to the invention. In this case a lower stop element 122 is formed integrally with a central element 123, and the upper stop element 124 is formed integrally with the central element 123.

The central element 123 and the stop elements 124, 122 are biodegradable and/or bioabsorbable upon elapse of the predetermined period of time. Upon biodegrading/bioabsorbing of the central element 123 and the stop elements 124, 122, the filter elements 125 are free to move from the capturing position to the open position.

Figure 38D:
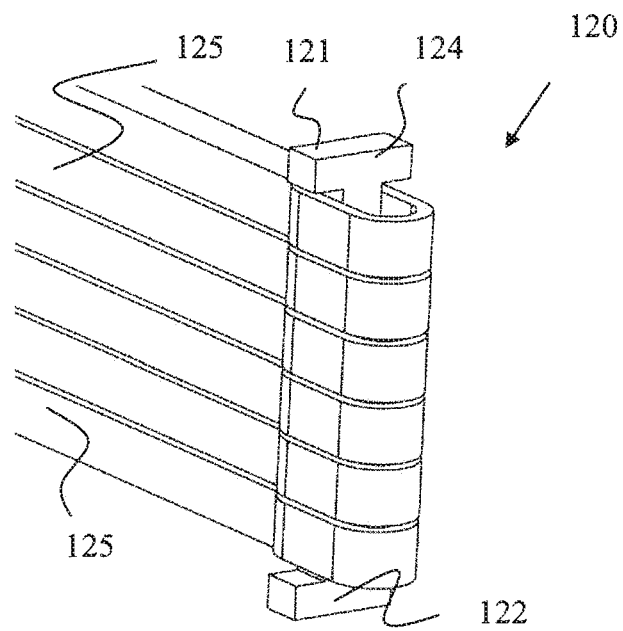
Figure 38E:
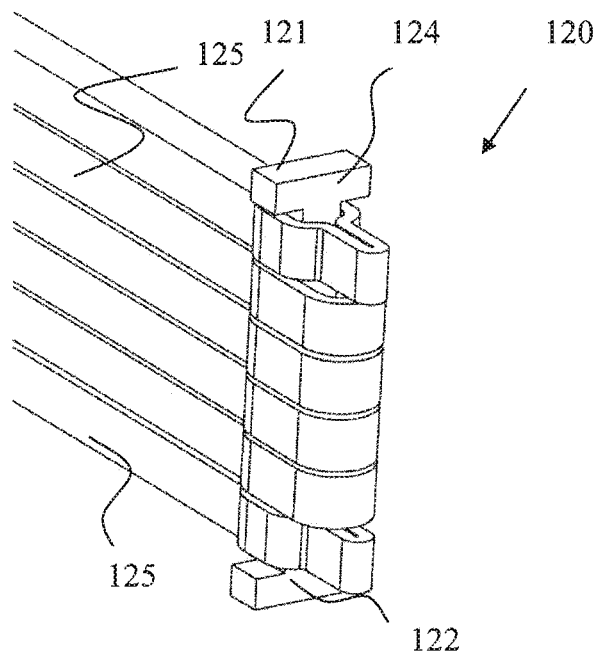
Figure 38F:
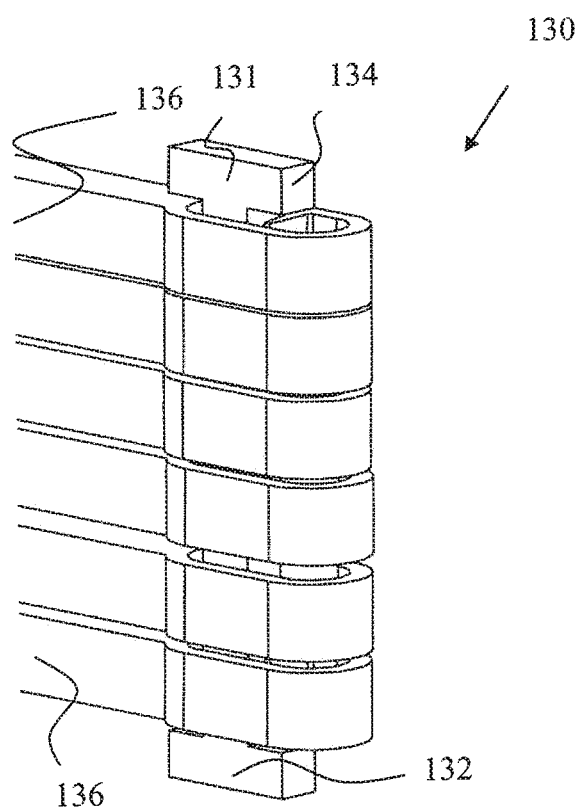
FIG. 38(f) is a perspective view of another vascular filter device of the invention.
Figure 38G:
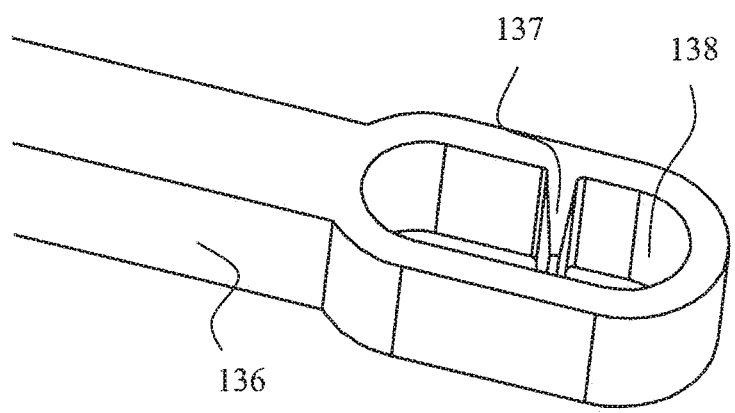
FIGS. 38(g) and 38(h) are isometric views of parts of this device.
Figure 38H:
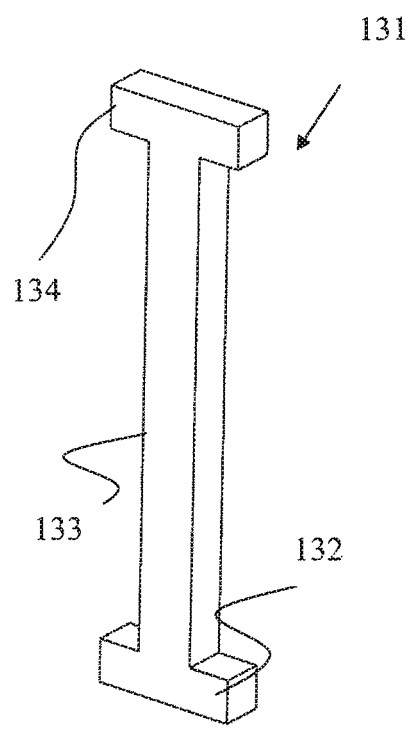

The 'T'-shaped pin 121 is threaded through the set of elongated eyelets 126 (FIGS. 38(b) and 38(c)) and twisted through 90° (FIG. 38(d)). The top and bottom eyelets 126 are formed to lock the pin 121 (FIG. 38(e)).

Referring to FIGS. 38(f) to 38(i) there is illustrated another vascular filter device 130. In this case an opening 138 in the upper filter element 136 comprises a retainer finger 137, and the opening 138 in the lower filter element 136 comprises a retainer finger 137. Each retainer finger 137 protrudes radially inwardly into the opening 138.

In the capturing position the upper stop element 134 engages with the retainer finger 137 of the upper filter element 136, and the lower stop element 132 engages with the retainer finger 137 of the lower filter element 136. In this manner the filter elements 136 are hold in the capturing position.

Figure 38I:
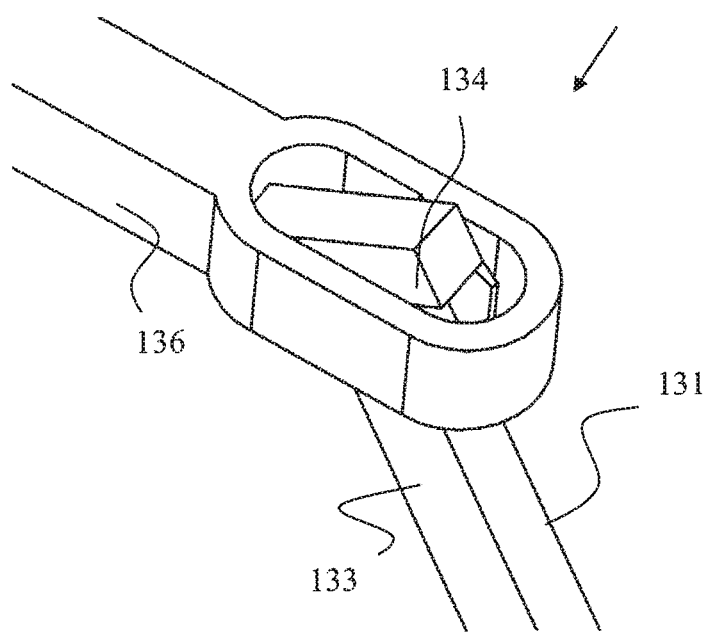
FIG. 38(i) is an isometric view illustrating manufacture of this device.

The upper stop element 134 is extendable through the opening 138 in the filter element 136 in a snap-fit manner to pass the retainer finger 137 (FIG. 38(i)).

The snap fit feature 137 may be provided in the top and bottom filter element 136. The snap fit feature 137 allows the T-head 134 to be edged through at an angle but not when fully assembled.

Figure 39:
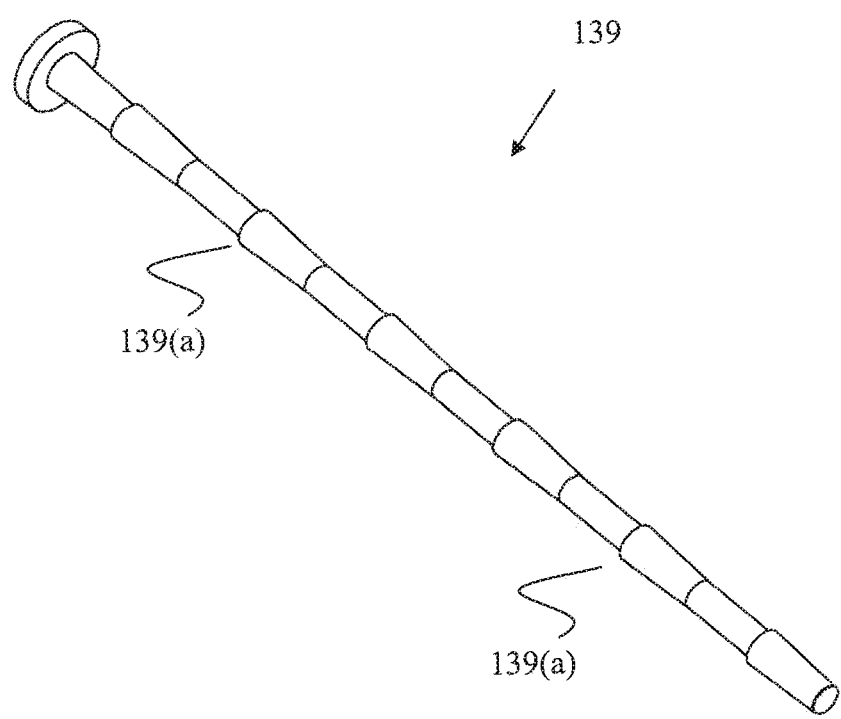
FIG. 39 is an isometric view of part of another vascular filter device of the invention.

Referring to FIG. 39 a central element 139 may comprise one or more protrusions 139(a) which may act as ratchets. Multiple ratchets 139(a) are shown but only one is required for the invention to function. Having only one ratchet 139(a) enables simultaneous opening upon conversion.

Figure 39A:
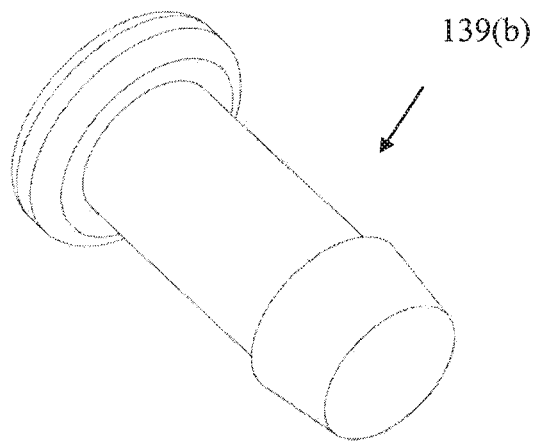
FIGS. 39(a) to 39(c) are views similar to FIG. 39 of parts of other vascular filter devices of the invention.
Figure 39B:
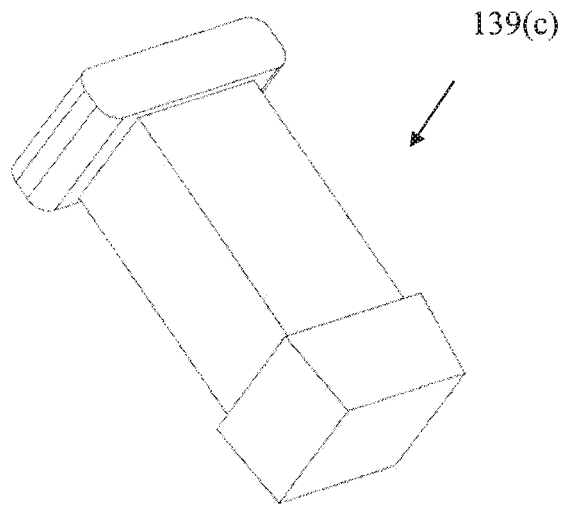
Figure 39C:
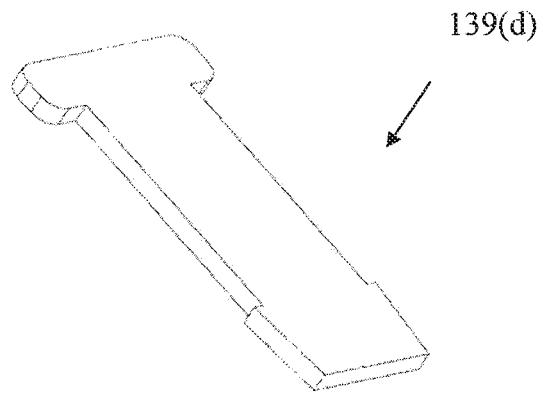

It will be appreciated that the pin element may be provided in a variety of possible forms, as illustrated in FIGS. 39(a) to 39(c), pins 139(b), 139(c), and 139(d) respectively. The snap fit pin may be provided as a square, round, or flat geometry.

The flat geometry may be manufactured by laser cutting the shape from a sheet of material, or machining the shape from a sheet of material, or stamping the shape from a sheet of material, or extruding the profile and cutting it to the desired thickness.

The square geometry may be manufactured in a similar way. A process may be required to remove material from the central section. Alternatively the head and the snap fit features may be formed through heat or plastic deformation on a square rod. Various rod cross sections may be used. The round pin may also be manufactured by heat forming a rod of material. Any of the pin element designs disclosed herein may be injection moulded.

Figure 40:
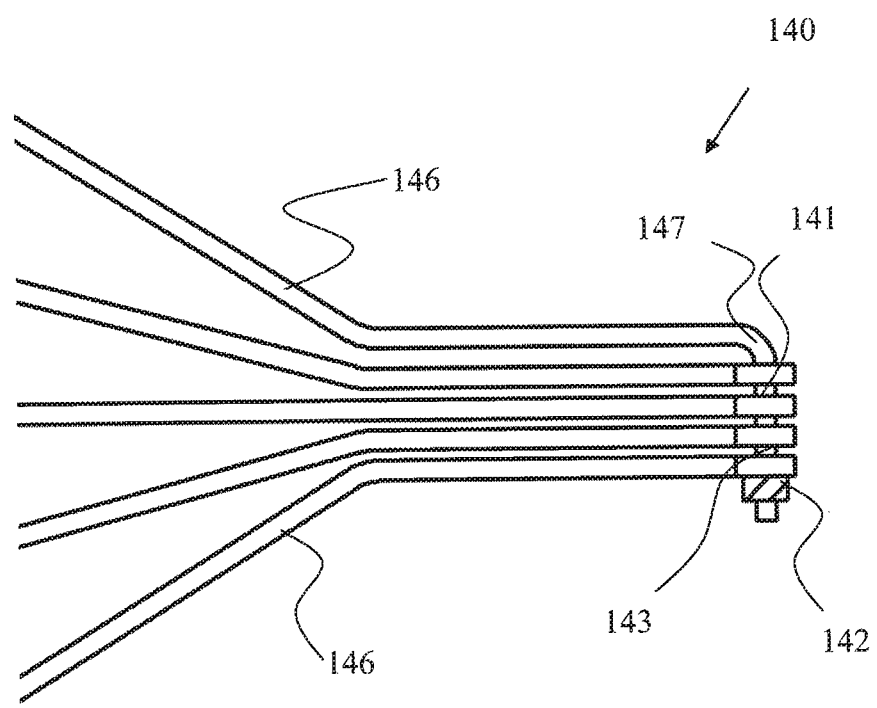
FIG. 40 is a view similar to FIG. 30 of another vascular filter device of the invention.

In FIG. 40 there is illustrated another vascular filter device 140 according to the invention. In this case a pin element 141 comprises an elongate central element 143, an upper stop element, and a lower stop element 142. The central element 143 is formed integrally with the upper filter element 146. The lower stop element 142 is formed separately to the central element 143.

The longitudinal axis of the pin element 141 is straight, and the central element 143 extends in a straight line through the opening in each of the other filter elements 146. By connecting together the central element 143 and the upper filter element 146 in a bend 147, this bend 147 acts as an upper stop element for the pin element 141.

In the capturing position the bend 147 engages with the adjacent filter element 146, and the lower stop element 142 engages with the lower filter element 146. In this manner the filter elements 146 are held in the capturing position.

The central element 143 is biostable, and the lower stop element 142 is biodegradable and/or bioabsorbable upon elapse of the predetermined period of time. Upon biodegrading/bioabsorbing of the lower stop element 142, the filter elements 146 are free to move from the capturing position to the open position.

The distal end of one of the filter elements 146 is used as the pin 143. Upon conversion, the pin portion 143 may be heat set to extend along the vessel wall rather than extending through the flow.

The stop feature 142 may be attached in a number of methods such as crimping, bonding, overmoulding, or welding.

Figure 41:
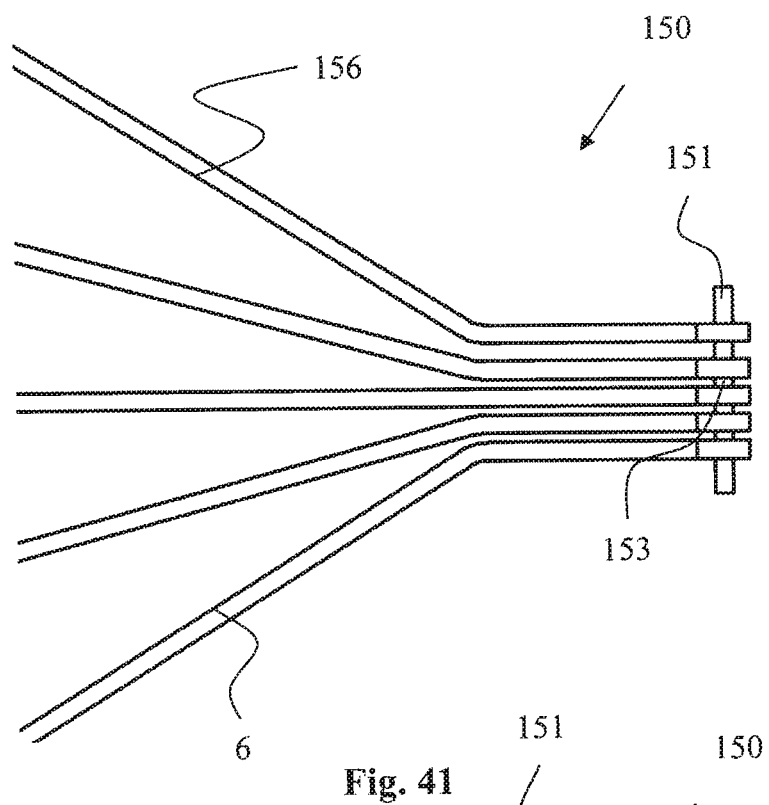
FIG. 41 is a view similar to FIG. 30 of another vascular filter device of the invention.
Figure 42:
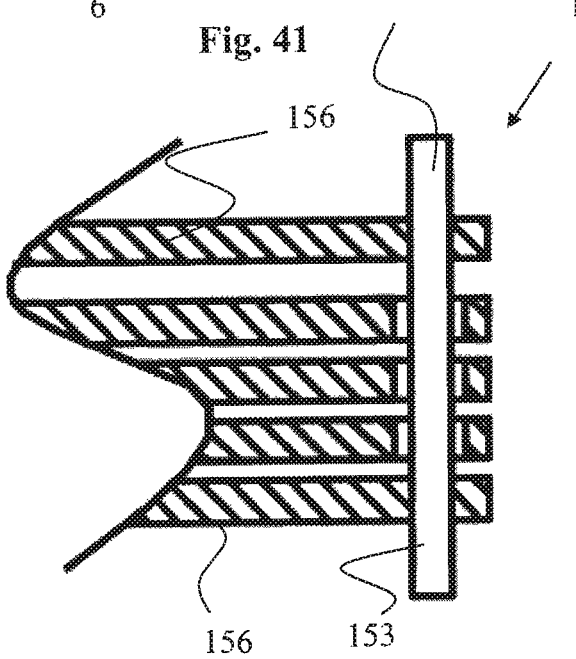
FIG. 42 is an enlarged, cross-sectional side view of part of the vascular filter device of FIG. 41.

FIGS. 41 and 42 illustrate a further vascular filter device 150 according to the invention. In this case a pin element 151 comprises an elongate central element 83 without any external stop elements.

In the capturing position a central element 153 engages with the internal wall of an opening of the upper filter element 156, and engages with the internal wall of the opening of the lower filter element 156. In this manner the filter elements 156 are held in the capturing position.

The central element 153 is biodegradable and/or bioabsorbable upon elapse of the predetermined period of time. Upon biodegrading/bioabsorbing of the central element 153, the filter elements 156 are free to move from the capturing position to the open position.

The top and bottom openings in the distal ends of the filter elements 156 are secured to the biodegradable pin 153. They may be secured by a number of methods such as bonding, crimping, or welding.

Alternatively the pin 153 may be biostable if a biodegradable material is overmoulded between the opening and the pin 153 at either end.

Figure 42A:
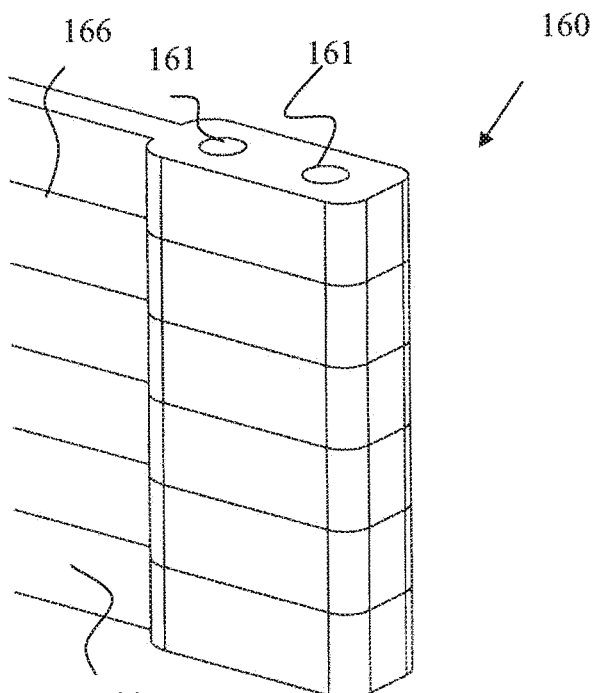
FIG. 42(a) is a perspective view of another vascular filter device of the invention.
Figures 42B, 42C:
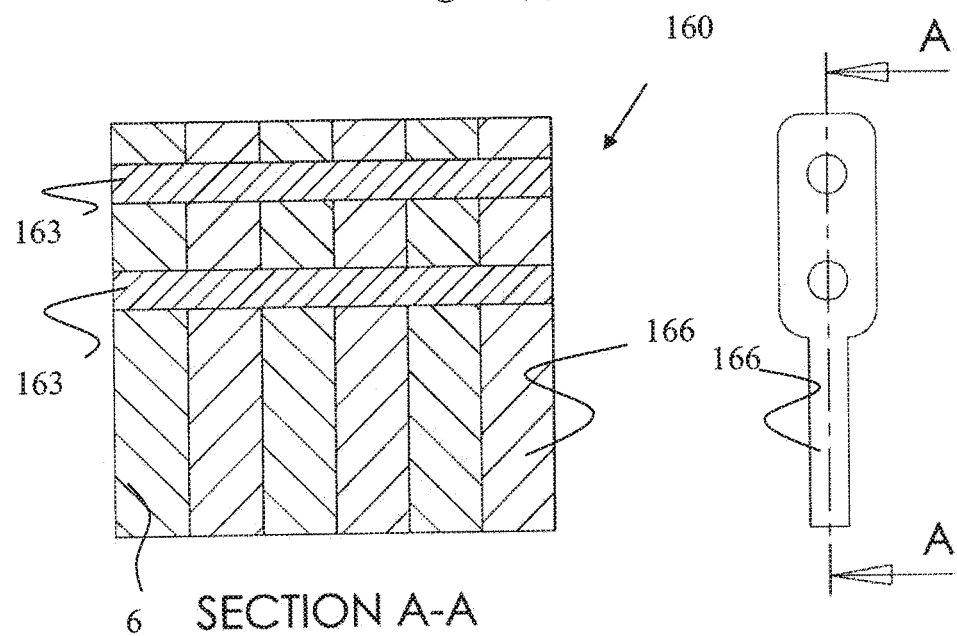
FIG. 42(b) is a plan view of part of this device.
FIG. 42(c) is a view along line A-A in FIG. 42(b)

Referring to FIGS. 42(a) to 42(c) there is illustrated another vascular filter device 160 according to the invention. In this case the holder member comprises two rigid pin elements 163 extending through openings 161. Each pin element 163 comprises an elongate configuration without any external stop elements.

In the capturing position each central element 163 engages with the internal wall of the opening 161 of each filter element 166. In this manner the filter elements 166 are held in the capturing position.

Each central element 163 is biodegradable and/or bioabsorbable upon elapse of the predetermined period of time. Upon biodegrading/bioabsorbing of each central element 163, the filter elements 166 are free to move from the capturing position to the open position.

Each eyelet 161 is provided with an opening profile that lines up when assembled. The bio-degradable material 163 is injected into the openings 161 and cured in-situ in the openings 161 to hold the assembly 160 together.

Figure 42D:
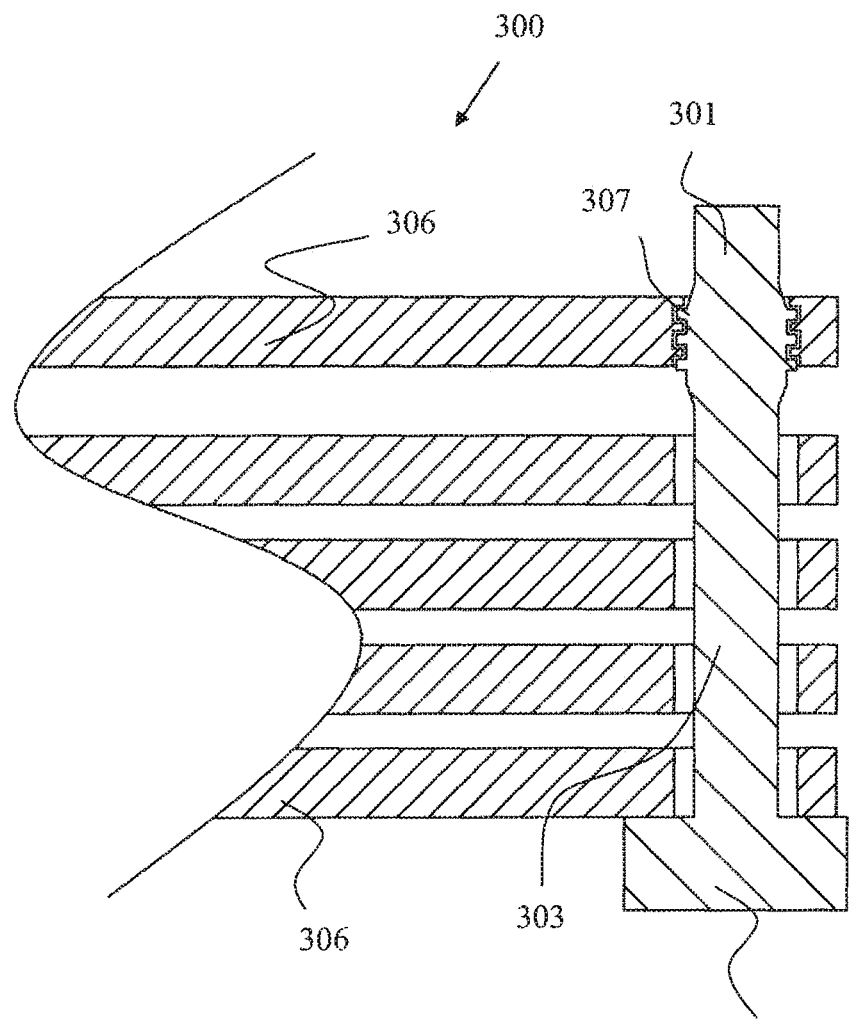
FIG. 42(d) is a cross sectional side view of part of another vascular filter device of the invention.
Figure 43:
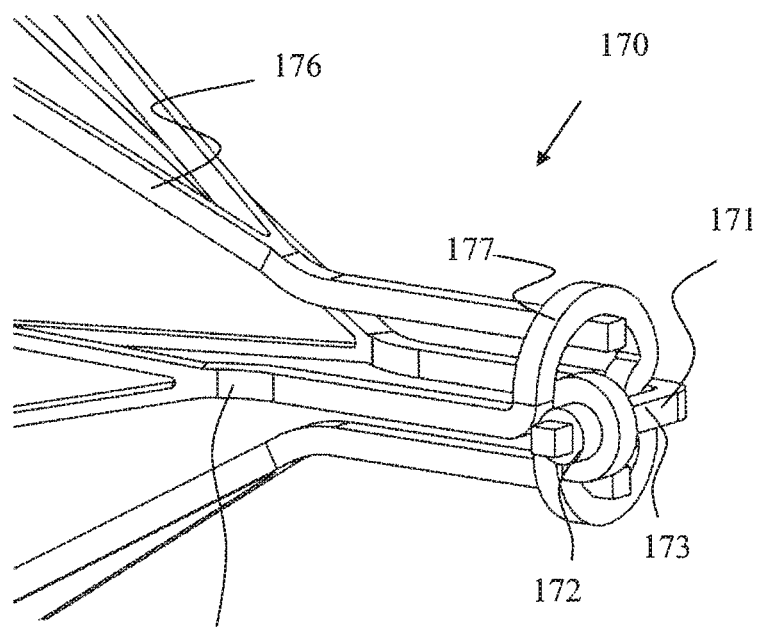
FIG. 43 is an isometric view from the front of part of another vascular filter device of the invention.
Figure 44:
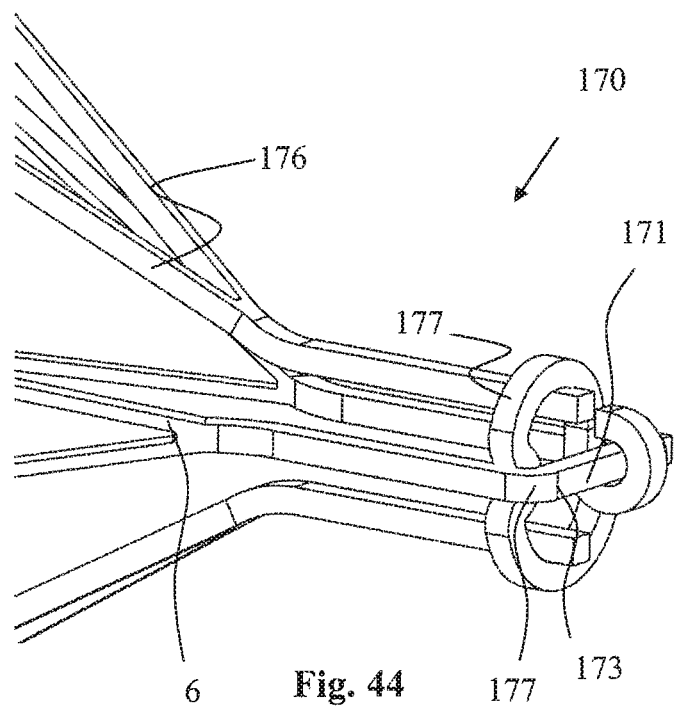
FIG. 44 is an isometric view from the rear of this device.
Figure 45:
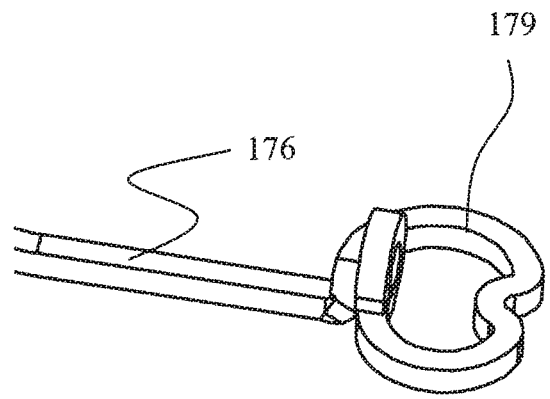
FIGS. 45 to 47 are isometric views of part of this device during manufacture.
Figure 46:
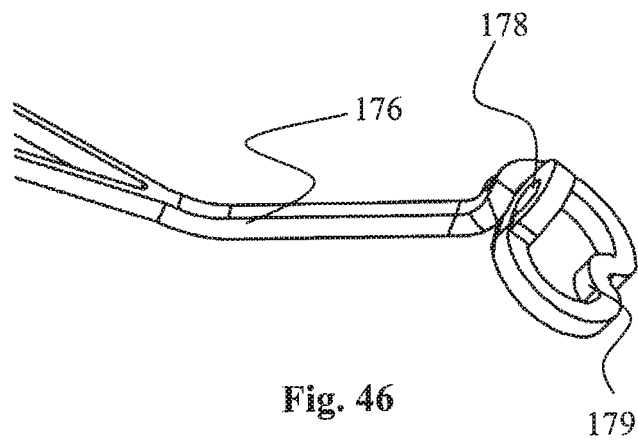

In FIG. 42(d) there is illustrated another vascular filter device 300 according to the invention. In this case a pin element 301 comprises an elongate central element 303 and a lower stop element 302. The lower stop element 302 is formed integrally with the central element 303. The pin element 301 comprises a thread formation 307 at the upper end of the central element 303. The opening 13 of the upper filter element 306 comprises a corresponding thread formation.

The central element 303 and the lower stop element 302 are biodegradable and/or bioabsorbable upon elapse of the predetermined period of time. Upon biodegrading/bioabsorbing of the central element 303 and the lower stop element 302, the filter elements 306 are free to move from the capturing position to the open position.

In the capturing position the thread formation 307 of the central element 303 engages with the internal wall of the opening of the upper filter element 306. In this manner the filter elements 306 are held in the capturing position.

The thread pattern 307 is incorporated to connect the pin 303 and the top eyelet. A separate threaded nut may be used instead of threading the eyelet. This nut would secure the filter elements in the capturing position externally of the adjacent filter element opening.

In FIGS. 43 to 47 there is illustrated another vascular device 170 according to the invention. In this case the holder member comprises a pin element 171 and a ring element 177.

The pin element 171 comprises an elongate central element 173, an upper stop element, and a lower stop element 172. The central element 173 is formed integrally with the upper filter element 176. The lower stop element 172 is formed separately to the central element 173.

The longitudinal axis of the pin element 171 is straight, and the central element 173 extends in a straight line through an opening 178 in the lower filter element 176.

By connecting together the central element 173 and the upper filter element 176 in a bend 177, this bend 177 acts as an upper stop element for the pin element 171.

The central element 173 is biostable, and the lower stop element 172 is biodegradable and/or bioabsorbable upon elapse of the predetermined period of time. The ring element 179 is biostable. Upon biodegrading/bioabsorbing of the lower stop element 172, the filter elements 176 are free to move from the capturing position to the open position.

The ring element 179 extends around two of the filter elements 176 to hold these two filter elements 176 in the capturing position until elapse of the predetermined period of time. In the capturing position the bend 177 engages with the ring element 179, and the lower stop element 172 engages with the lower filter element 176. In this manner the filter elements 176 are held in the capturing position.

Figure 47:
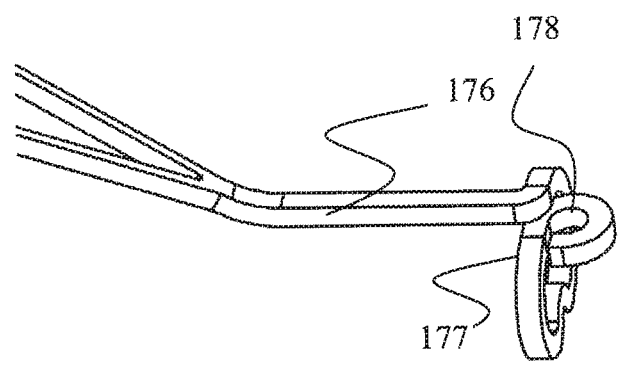

The apex ring device 170 consists of three types of apex ending: the double ring ending, the straight endings, and the long straight ending 173. To assemble the filter 170, the large ring 179 is manipulated through 90° (FIG. 47). The large ring 179 is biased to sit at 180°. The long ending 173 is manipulated to sit in the crevice of the large ring 179 and to extend through the small ring 178. The biodegradable cap 172 is attached to the long ending 173 to hold the assembly 170 together. Any number of straight endings 176 can then be manipulated to sit within the large ring 179. Upon biodegradation, all endings 176 revert to their radially outwardly biased position at the vessel wall. The double ring 179 and the long ending 173 are biased to extend along the vessel wall rather than into the flow.

The device 170 enables simultaneous opening upon conversion and also provides reduced obstruction to flow. Obstruction may be reduced further by increasing the diameter of the large ring 179.

Figures 48, 49:
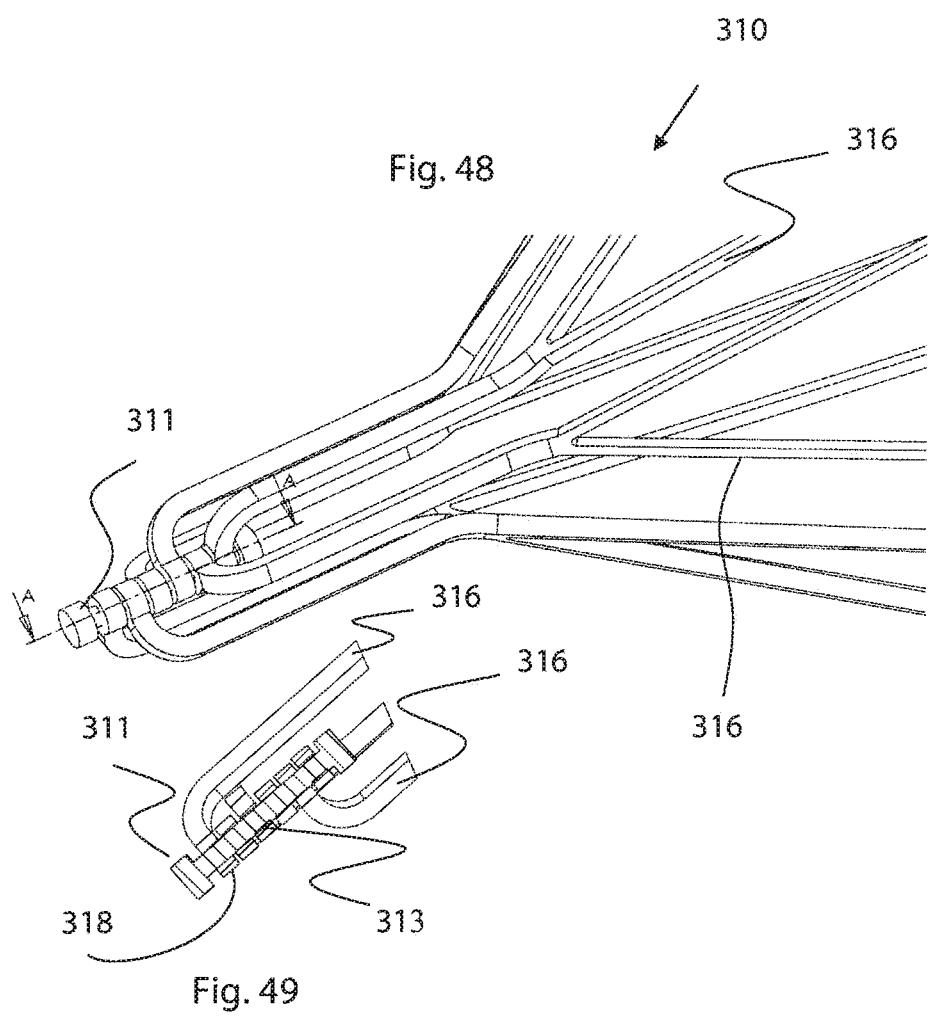
FIG. 48 is a perspective view of another vascular filter of the invention.
FIG. 49 is a view along line A-A in FIG. 48.

FIGS. 48 and 49 illustrate a further vascular filter device 310 according to the invention, in this case in the capturing position the filter elements 316 are arranged with the openings 318 in the filter elements aligned longitudinally in a straight line (FIG. 49). The longitudinal axis of a pin element 311 is straight. The central element 313 extends in a straight line through the opening 318 in each filter element 316.

The pin 311 is orientated to lie along the longitudinal axis of the vessel. This ensures that stresses exerted on the pin 311 are independent of the orientation that the device 310 is deployed in the vessel. This arrangement also aids in the manufacturing process.

Figure 50:
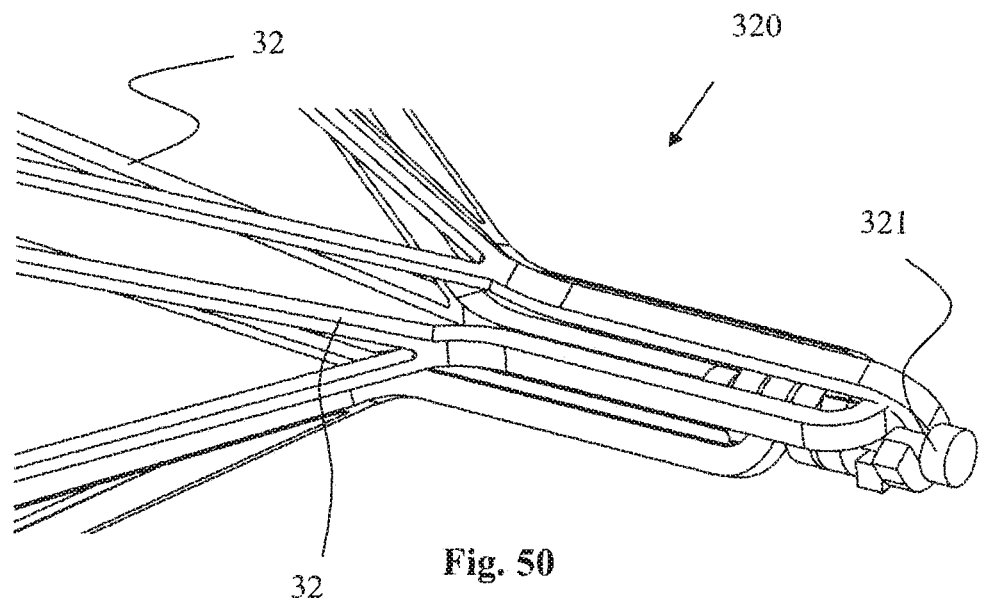
FIG. 50 is a perspective view of another vascular filter device of the invention.
Figure 51:
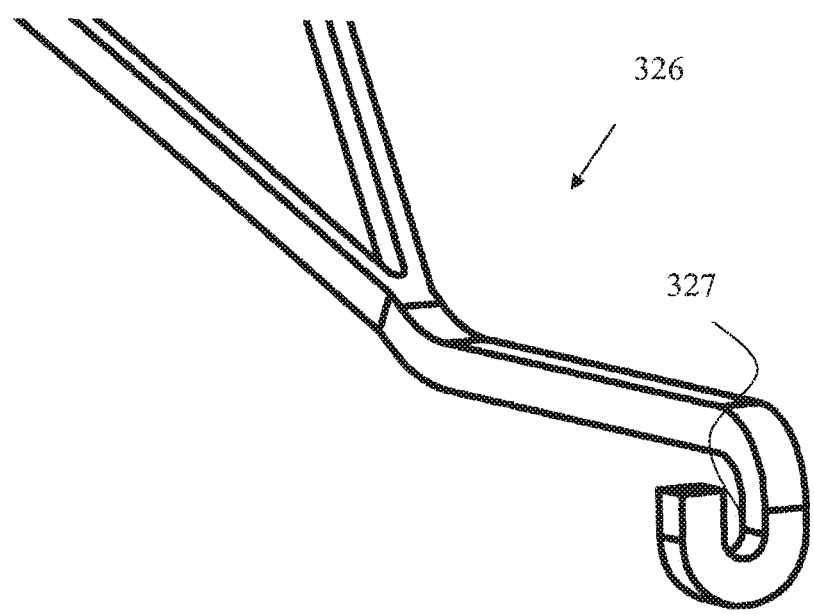
FIG. 51 is an isometric view of part of the vascular filter device of FIG. 50.
Figure 53:
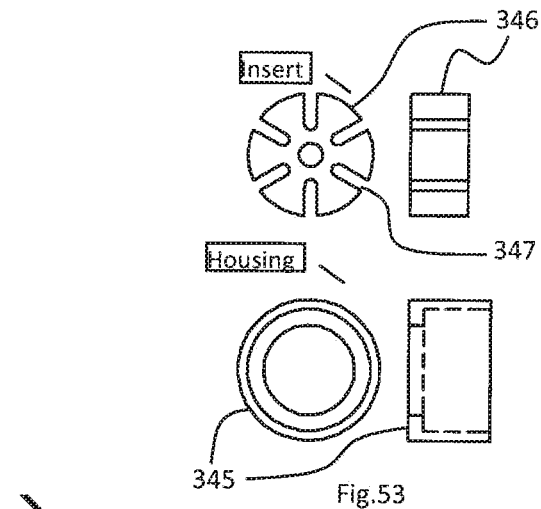
FIG. 53 illustrates a holder insert and housing for use with these filter elements.
Figure 52:
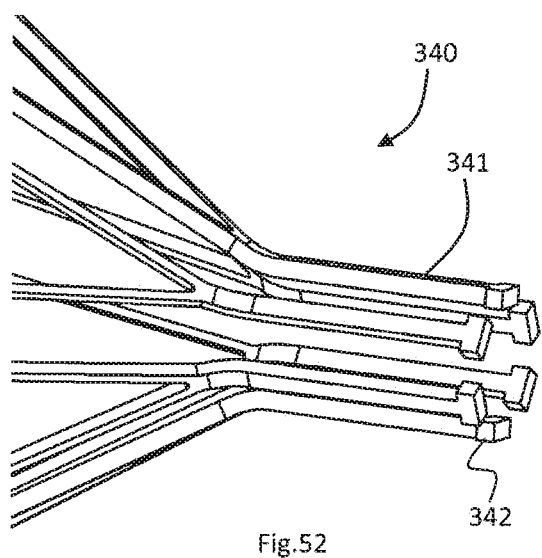
FIG. 52 is a perspective view of the ends of filter elements.
Figure 54:
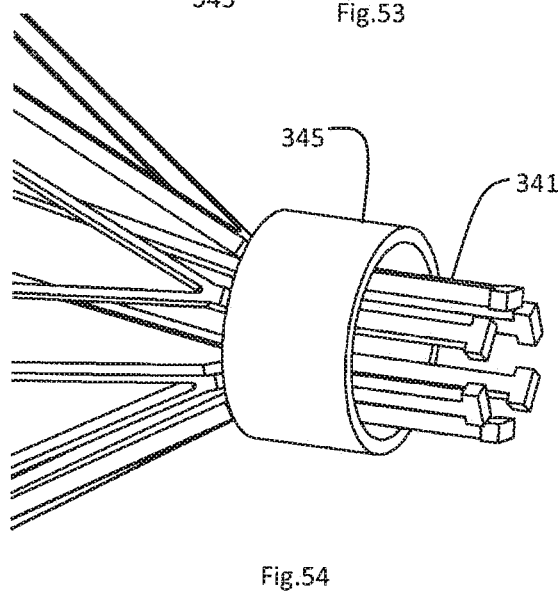
FIGS. 54 to 56 are views showing connection of the holder parts.
Figure 55:
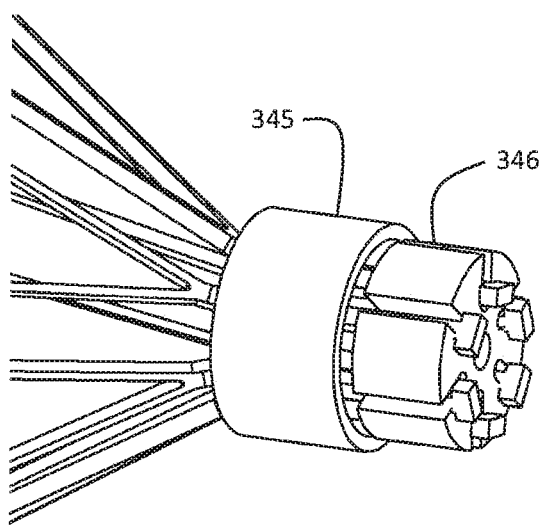
Figure 56:
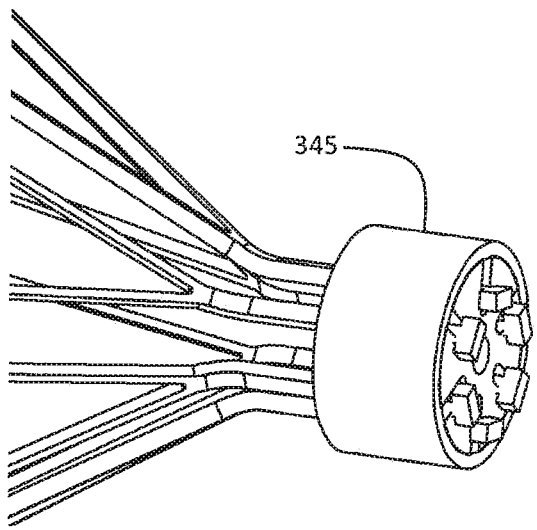

Referring to FIGS. 50 and 51 there is illustrated another vascular filter device 320 according to the invention. In this case a 'U'-shaped slot opening 327 is provided at the distal end of each of the filter elements 326. As illustrated in FIG. 51, a portion of the wall of the filter element 326 extends around only part of the circumference of the opening 327 to define the opening 327.

The eyelets of the device 320 incorporate the open slot 327 to aid insertion of the pin 321 with caps at either end. As the open slot 327 changes orientation for each filter element 326, the pin 321 will be securely held in position.

Referring to FIGS. 52 to 56, a holder assembly of a device 340 comprises distal ends 341 of filter elements and end stops 342. There is a biodegradable holder housing 345 and a biodegradable holder insert 346. The housing fits over the ends 341. The ends 341 are positioned in grooves 347 of the insert 346 and the stops 342 prevent axial sliding. An interference fit is enough to prevent dis-assembly during use. The mating surfaces of the insert and of the housing may be tapered to allow easier assembly and a wider tolerance range for the parts. Snap fit prongs may be added to the housing or insert as a double measure to prevent dis-assembly. As the housing slides distally the prongs would snap over the distal face of the insert. Alternatively, the insert may have an integral locking thread/feature that engages with a locking thread/feature on the housing. After the housing is pushed over the insert, it is rotated relative to the insert to engage the lock. The interlocking holder can be adapted for filter elements that end in a linear array rather than the circular array shown. Only one filter element needs to have a stop feature and to be looked in a groove, the remaining filter element ends need not have the stop feature and could float freely in one or more larger grooves. The holder may have an increased wall thickness surrounding one of the filter elements or alternative securing member so that the holder remains attached to one of the filter elements in the open position.

Figure 57:
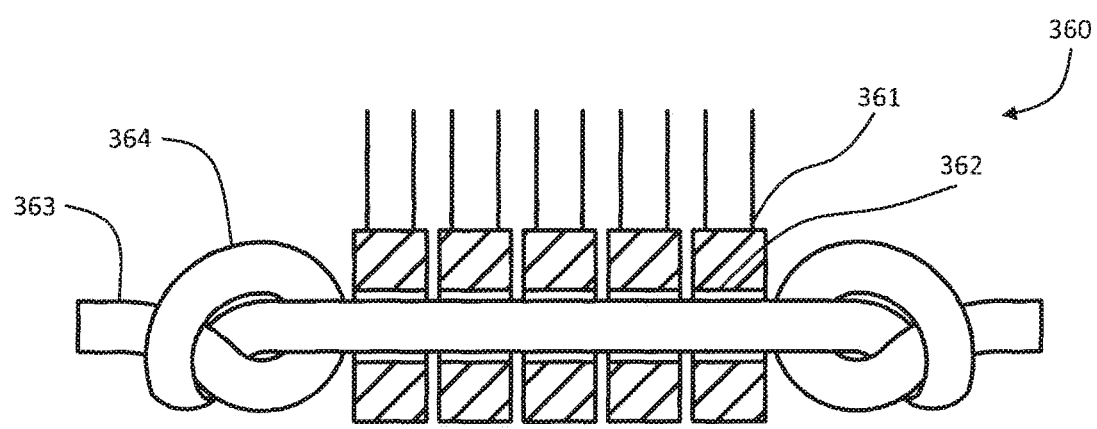
FIG. 57 is a cross-sectional view showing a holder assembly with a flexible pin tied at both ends.

Referring to FIG. 57 a holder assembly 360 has a set of filter element ends 361 with aligned openings 362 through which a flexible biodegradable pin 363 extends. There is a tie at each end of the pin 363.

Figure 58:
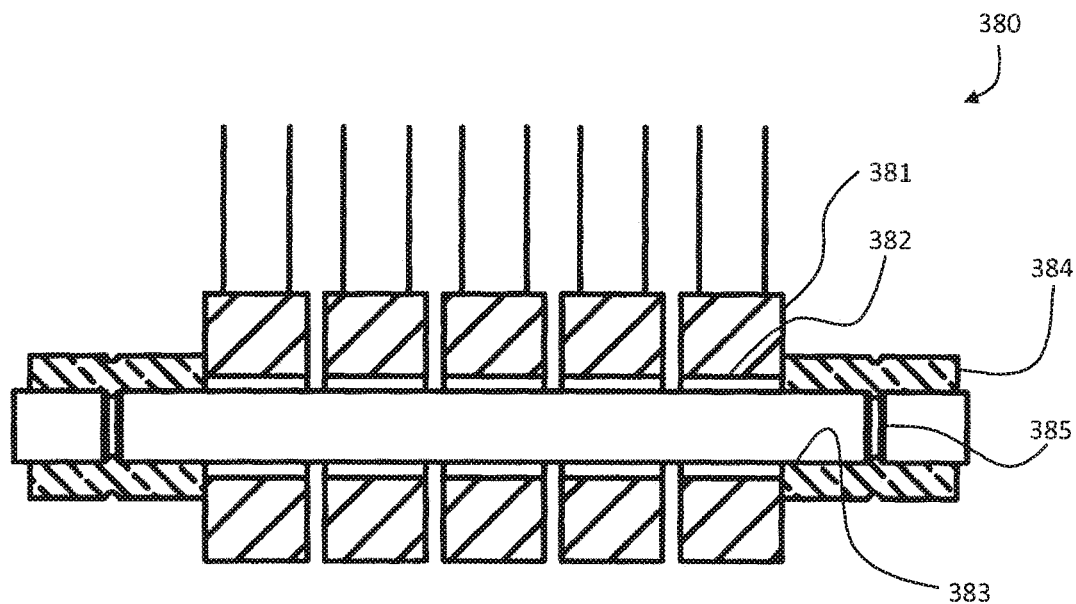
FIGS. 58 and 59 are cross-sectional views showing a holder assembly with a heat shrink tube.
Figure 59:
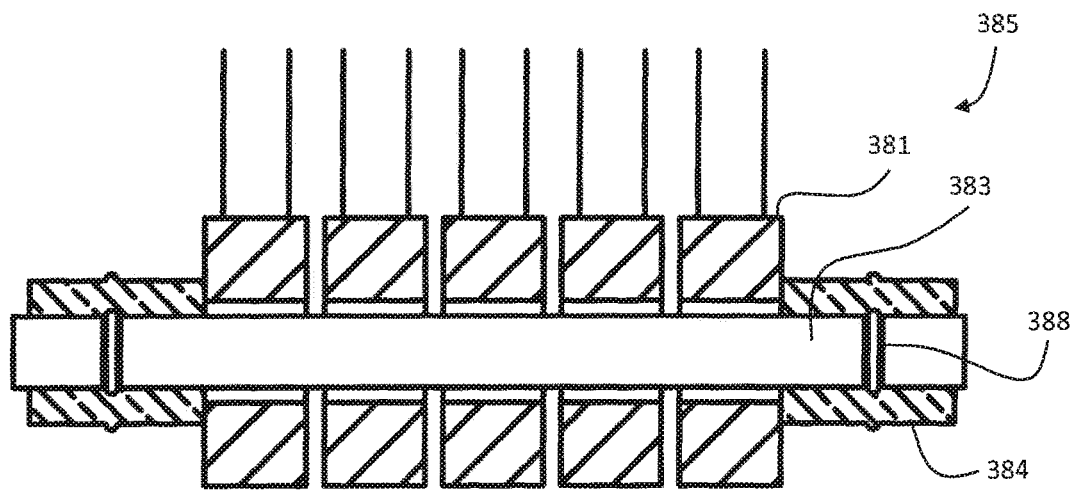

Referring to FIG. 58 a holder assembly 380 comprises filter element ends 381 with openings 382. A biodegradable pin 383 extends through the openings and a heat shrink tube 384 fits over the ends of the pin 383. A circumferential recess 385 helps to retain the tube 384. FIG. 59 shows a variation in which there is a circumferential ridge 388 instead of a recess. Either of the tube and pin may be biodegradable.

Figure 60:
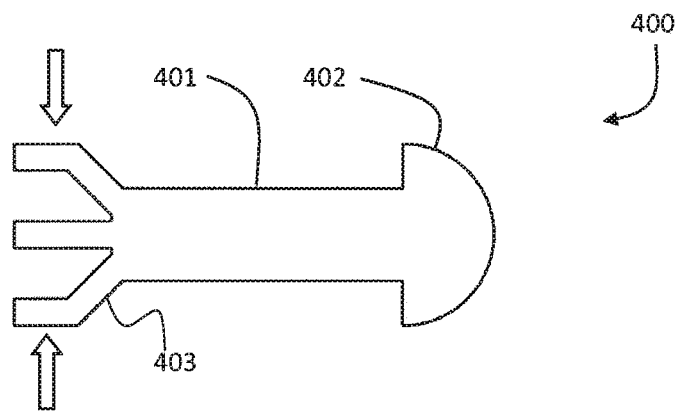
FIGS. 60 to 62 are diagrammatic side views showing insertion of a holder clawed pin into place through the ends of filter elements.
Figure 61:
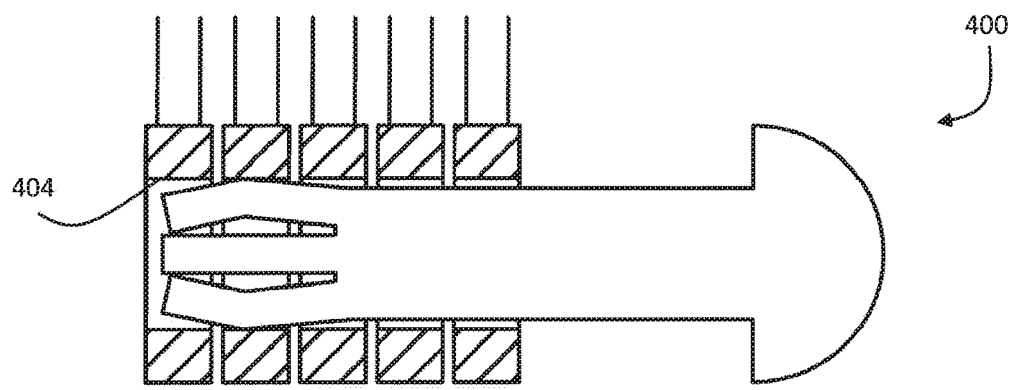
Figure 62:
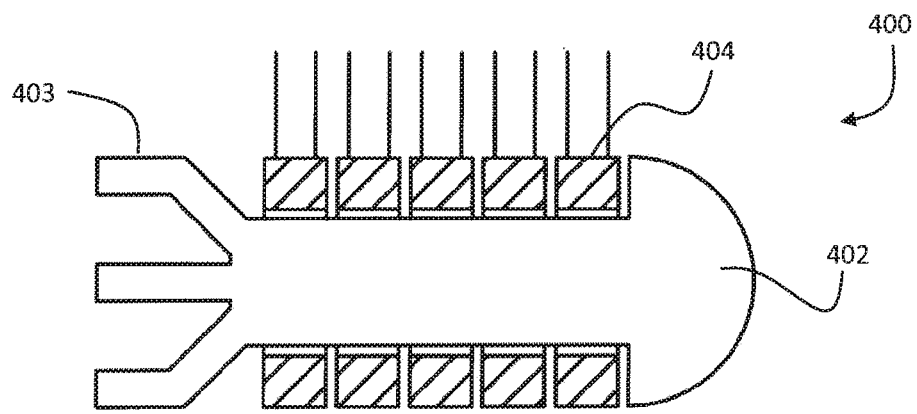

Referring to FIGS. 60 to 62 a holder assembly 400 comprises a biodegradable clawed pin 401 having a head 402 and splayed-out claws 403. The claws are pressed in to pass through aligned filter element openings 404. The pin 401 may be machined, stamped, or moulded.

Figure 63:
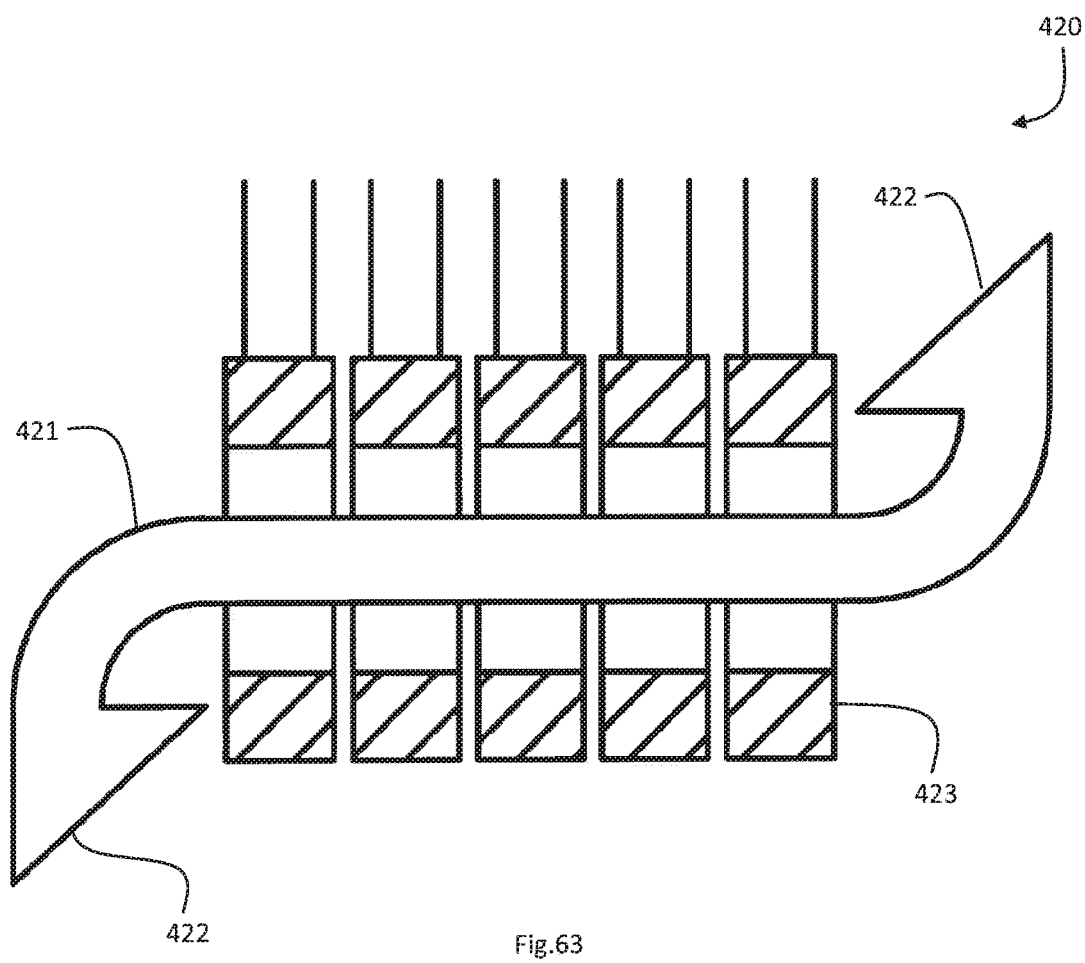
FIG. 63 is a cross-sectional view showing a holder assembly having a pre-tapered pin inserted through the ends of filter elements.
Figure 64:
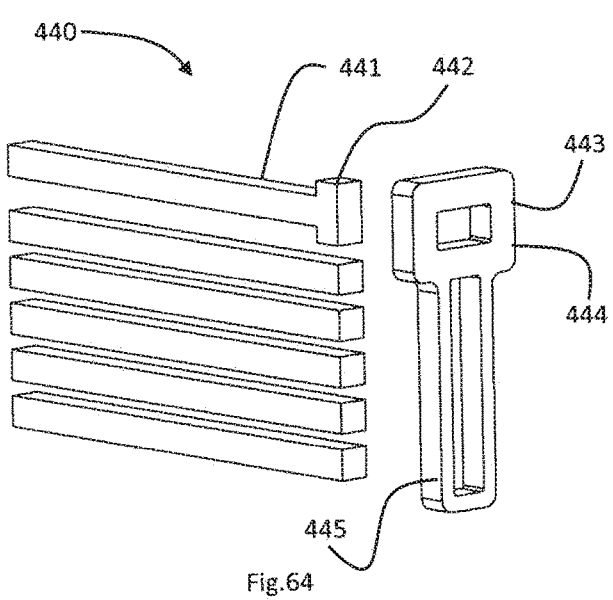
FIGS. 64 to 67 is a set of perspective views showing connection of a holder assembly having a twist lock arrangement.
Figure 65:
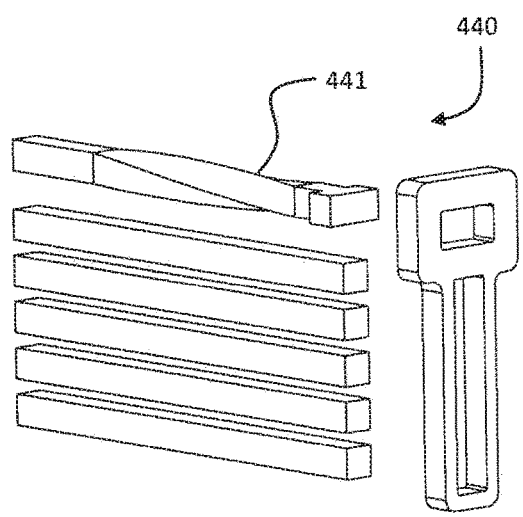
Figure 66:
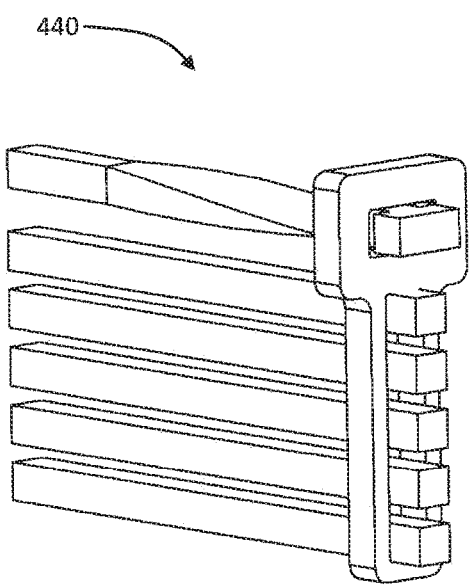
Figure 67:
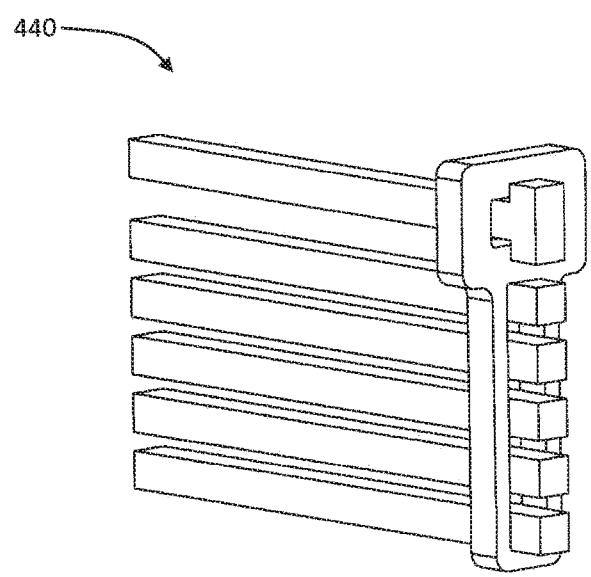

FIG. 63 shows a biodegradable pro-tapered pin 421 in a holder assembly 420. The pin 421 extends through openings in filter element ends 423, and the pin has a barb 422 at each and, and the pin is bent through approximately 90° just before the barb 422.

Referring to FIGS. 64 to 67 a holder assembly 440 comprises a filter element end 441 with a stop feature 442. A T-shaped biodegradable coupler 443 has a head 444 through which the stop feature 442 extends after it has been twisted through about 90°. Then the filter element end 441 relaxes, it is orientated so that the stop 442 engages behind the coupler head 444. The remaining filter element ends are prevented from moving by an elongate slot 445 in the stem of the coupler 443. FIGS. 68 to 70 show variations as follows:

- FIG. 68, a biodegradable coupler 450 has a slot 451 running its full length,
- FIG. 69, a biodegradable coupler 460 is I-shaped, with two heads 462 having openings 463, and a stem 461 with an elongate slot,
- FIG. 70, a biodegradable coupler 470 is also I-shaped, having heads 472 with a neck formed by protrusions 473 and a stem 471 with an elongate slot.

Figure 71:
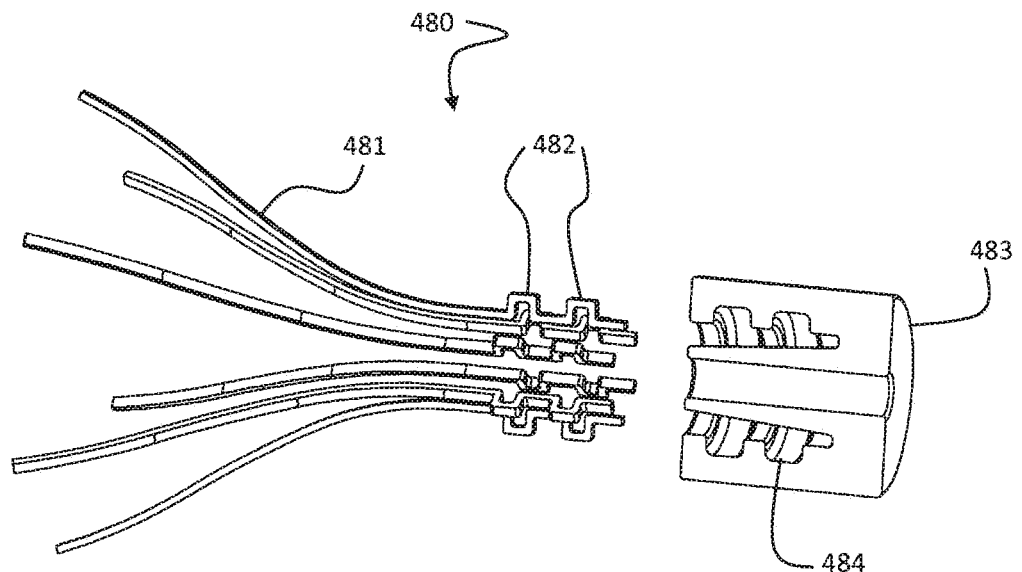
FIGS. 71 and 72 are perspective views of an alternative holder assembly, in which a holder cap fits over ridges in the ends of filter elements.
Figure 72:
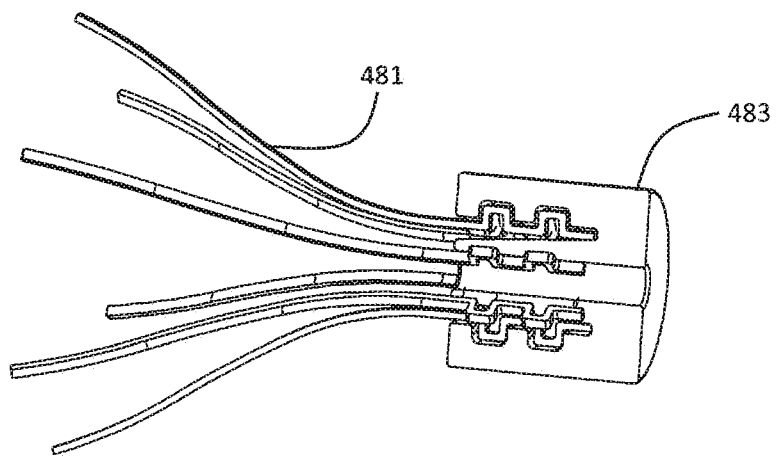

Referring to FIGS. 71 and 72, a holder assembly 480 comprises curved filter element ends 481, each having two ridges 482 at the end. A biodegradable lure cap 483 has an internal thread 484, into which the combined ends of the filter element 481 are engaged. This is shown in FIG. 72. The cap 483 may be fitted with a central lumen to aid flushing away of acids formed through degradation.

Figure 73:
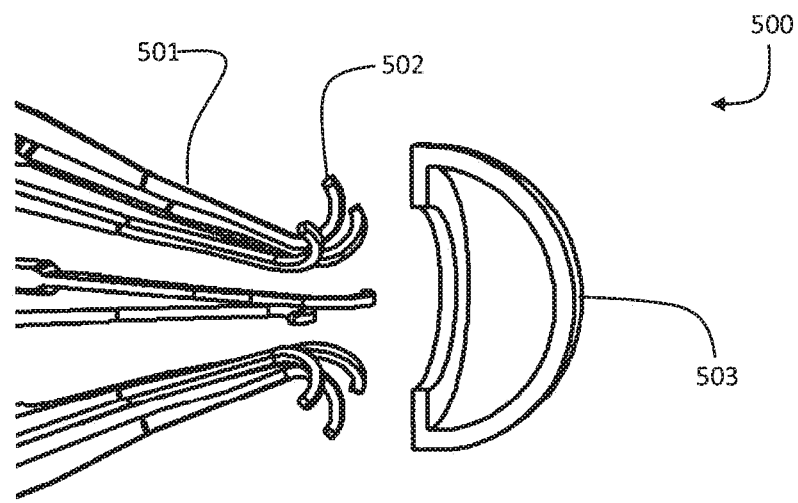
FIGS. 73 and 74 are partly cut-away side views showing a still further holder assembly of the invention, in which filter element ends snap fit into a holder cap.
Figure 74:
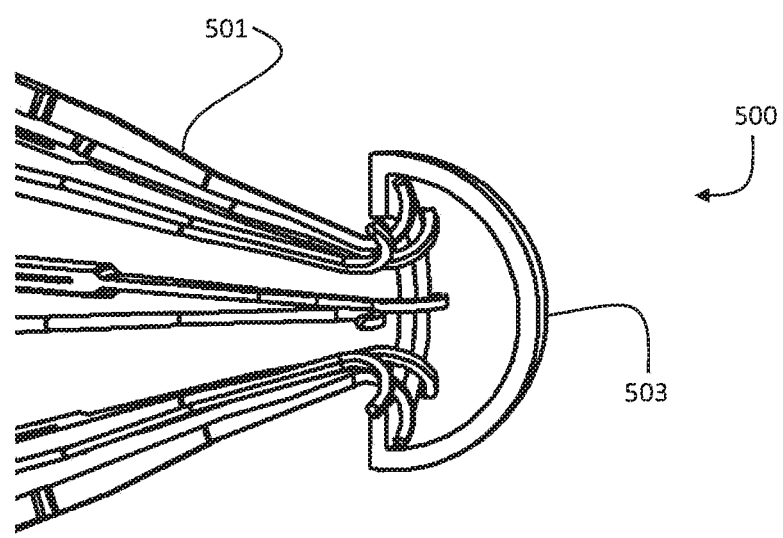

Referring to FIGS. 73 and 74 a holder assembly 500 has filter elements 501 with hooked ends 502 which snap fit into an opening in a dome-shaped biodegradable cap 503. The cap 503 may be rigid or flexible. If a flexible cap is used, the filter element ends may make contact with each other in the capturing position. When pushing together, the flexible cap and filter element ends both deform until the filter element ends are secured together in the capturing position.

Figure 75:
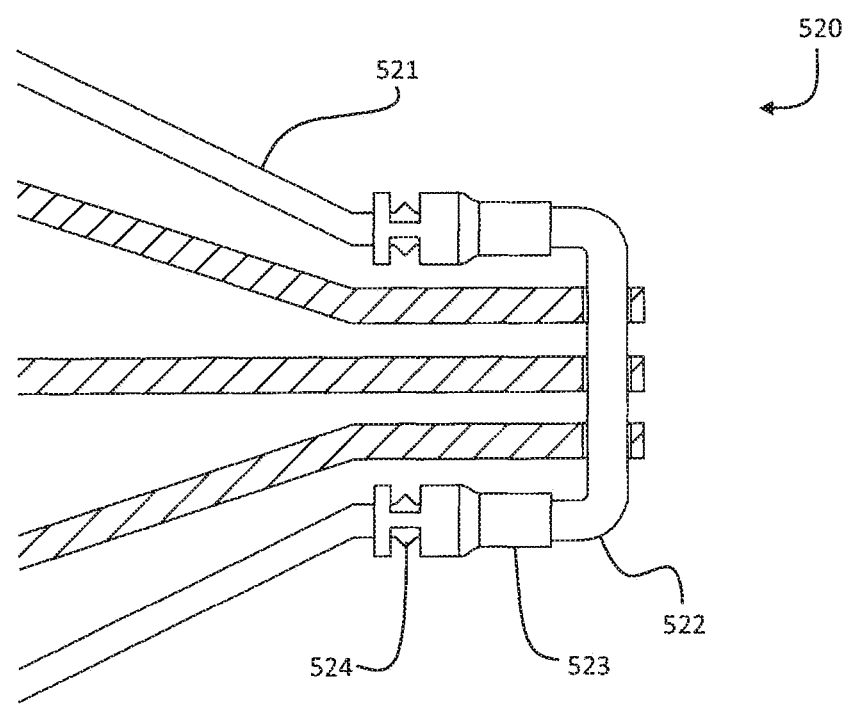
FIG. 75 is a cross-sectional view showing a holder assembly having a biodegradable tube snap-fitted over ridges.

Referring to FIG. 75 a holder assembly 520 comprises filter elements 521 retained by a biodegradable C-shaped coupler 522 having a sleeve 523 at each end push-fitted onto the filter element ends. The sleeve 523 has proximal slots that the filter element snap features 524 fit into. The distal end of the sleeve is crimped or bonded onto a flexible or rigid biodegradable coupler 522 that extends through openings in the filter elements.

Figure 76:
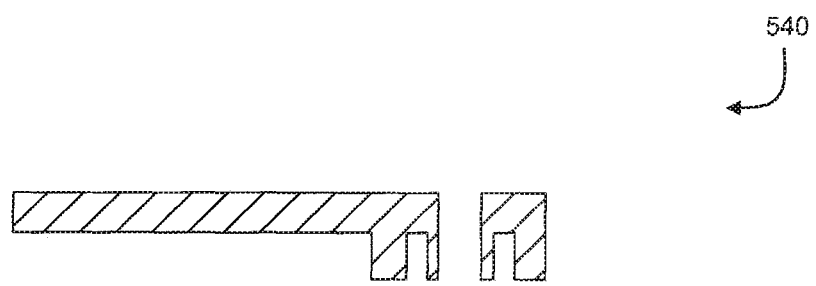
FIGS. 76 and 77 are views of a further holder assembly having a tube to allow washing away of acids produced during degradation.
Figure 77:
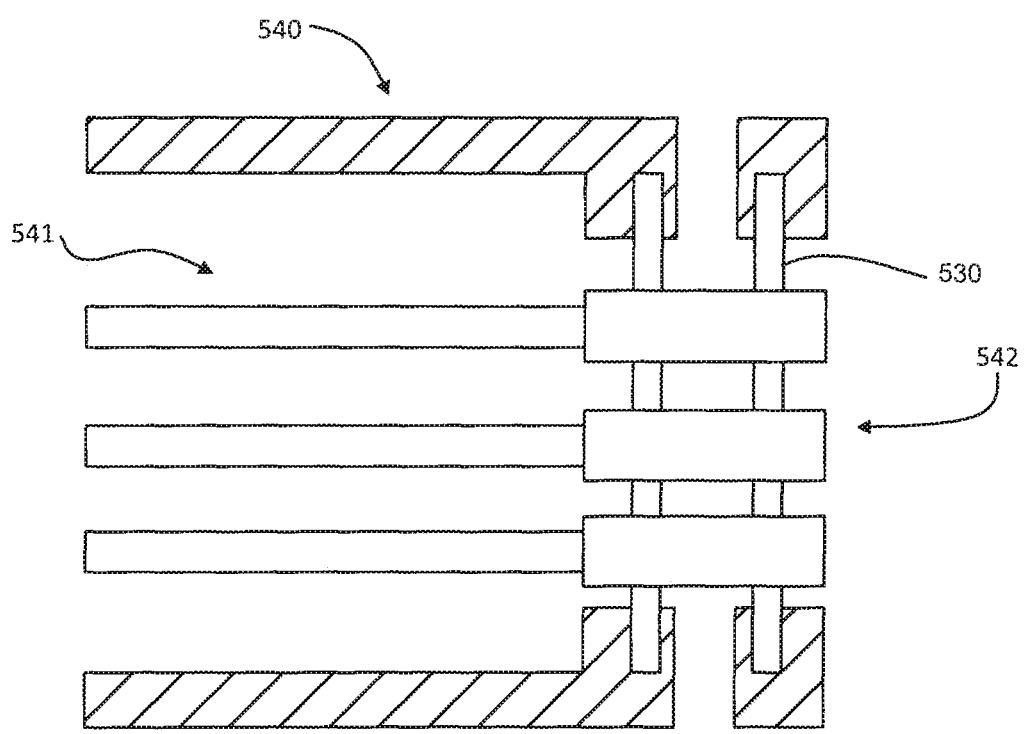

Referring to FIGS. 76 and 77 a biodegradable tube 540 extends through openings in central filter elements 541 and top and bottom coupling filter elements 530 are secured to the ends of the tube 540. The coupling filter elements are secured to the tube through crimping, bonding, or, interference fitting. The lumen allows washing away of acids, produced during degradation, to slow down the degradation process.

Figure 78:
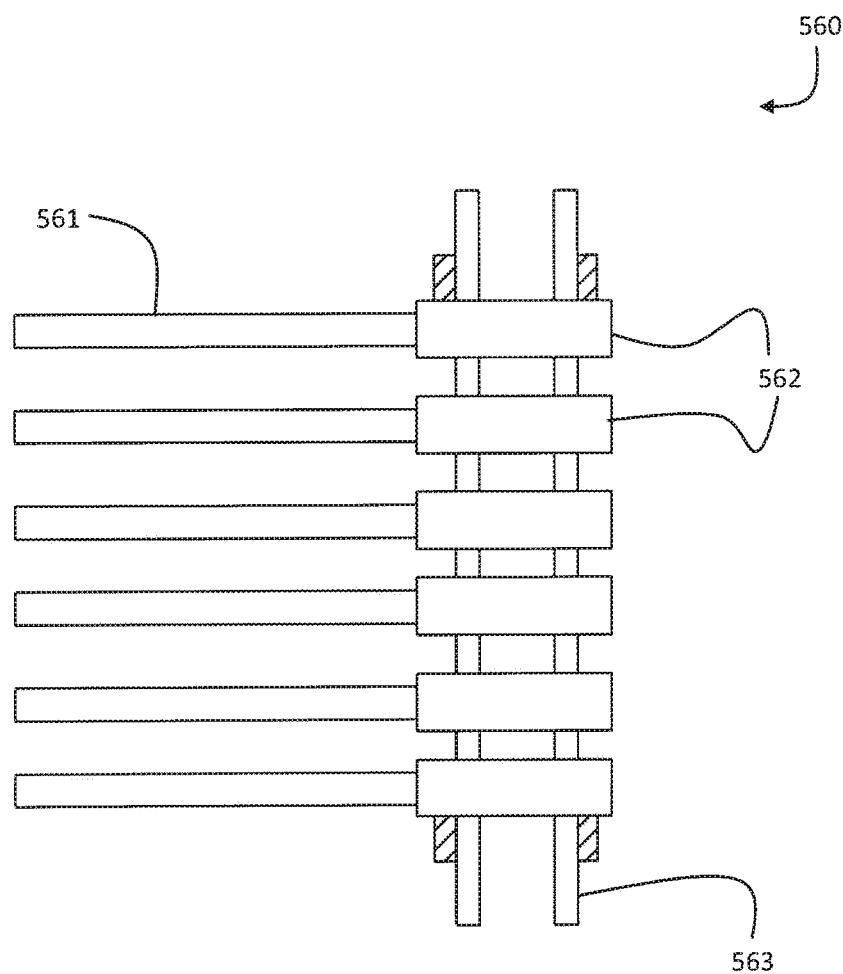
FIG. 78 shows an alternative assembly to achieve this.

Referring to FIG. 78 a holder assembly 560 has filter elements 561 with openings 562 through which a biodegradable tube 563 extends. Stop features secure the filter elements on the tube externally of the openings. Again a lumen through the tube allows washing away of acids produced during degradation, thereby providing control over the degradation period according to the selected tube configuration.

Figure 79:
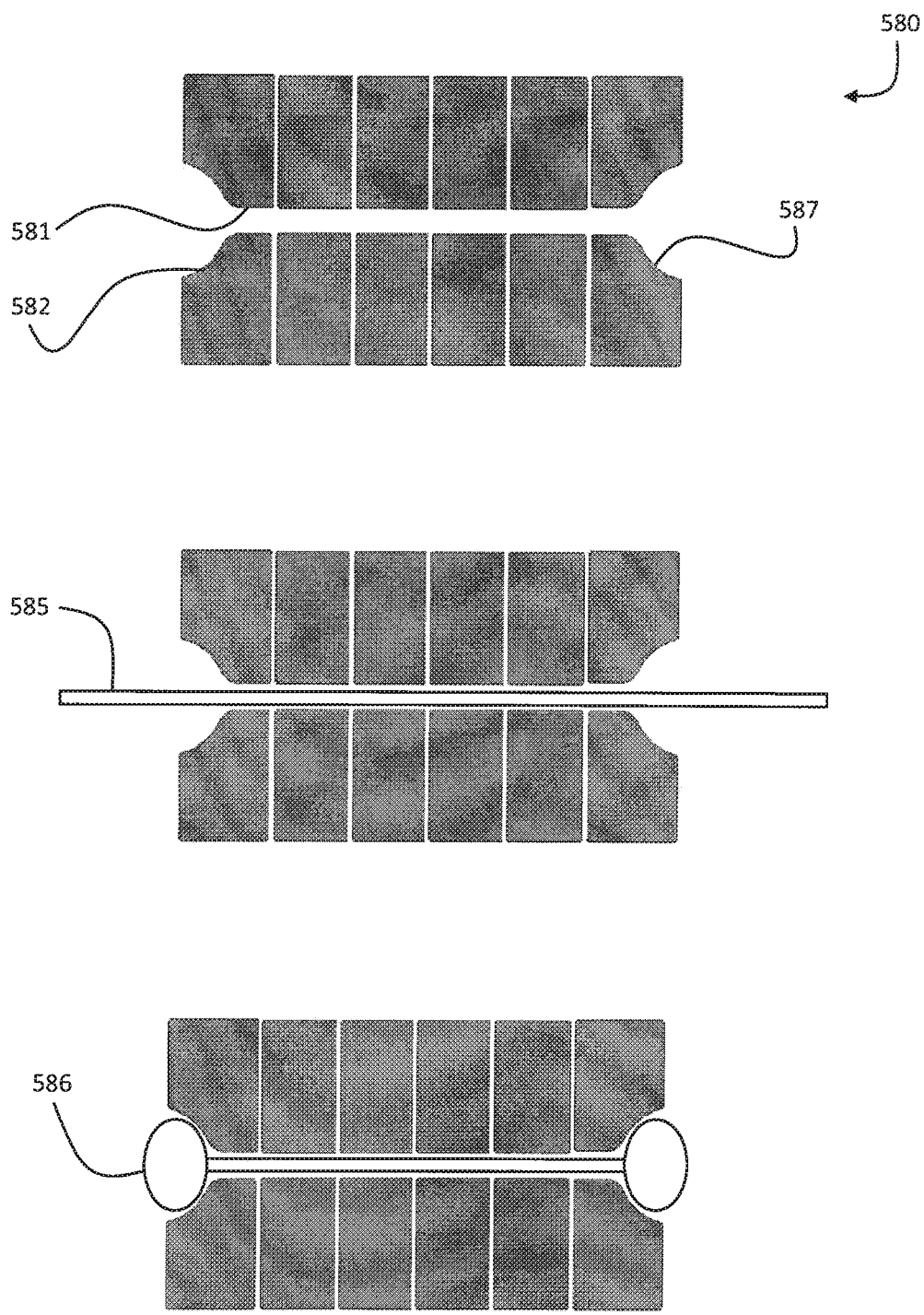
FIG. 79 is a set of diagrams showing in-situ moulding of a holder pin.

Referring to FIG. 79 a pin 585 is formed in situ in a series of openings 581 in filter element ends. Bad filter elements have a recess 587 into which a cap, at the ends of the pin, is formed to retain the filter elements. The cap is formed through application of heat, ultrasonics, or solvent moulding.

Figure 80:
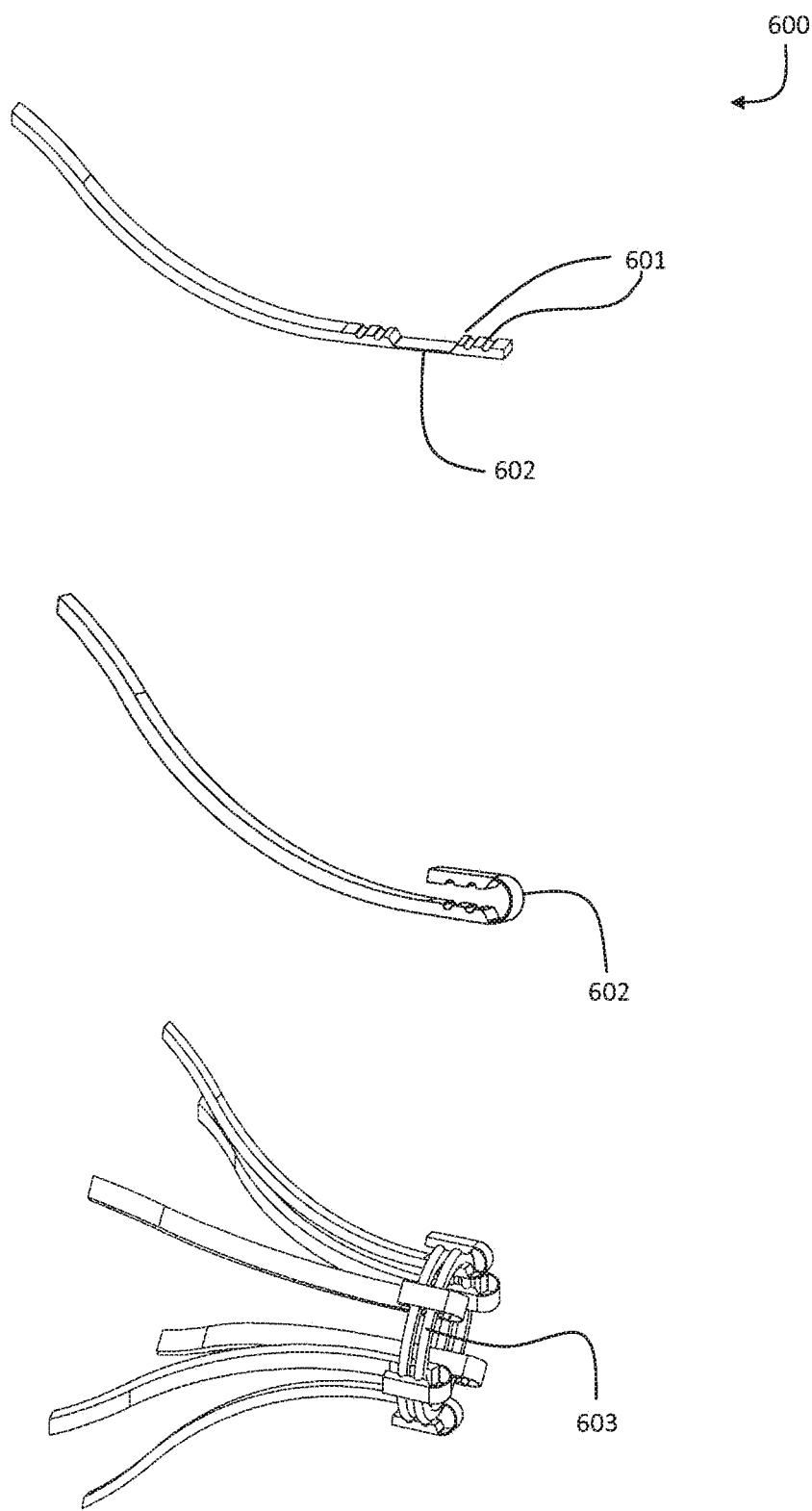
FIG. 80 is a set of views showing engagement of bent-over filter element ends around holder rings.

Referring to FIG. 80 a holder assembly comprises filter elements 600 having two series' of ridges 602 separated by a gap 602. The filter element is folded over at the gap 602 to engage with rings 603. The wall thickness of the gap section 602 is less than that of the filter element to aid bending. Multiple ridges may be provided to facilitate use of multiple rings.

Possible materials for any of the biodegradable/bioabsorbable elements disclosed herein are listed below:

| Polymers and composition percentages to achieve a 4-24 month filtration period | |
|---|---|
| Polymer | Composition (%) |
| Poly(L-lactide)/Polyglycolide (PLL/PG) | 80/20 to 100/0 |
| Poly(L-lactide)/Poly(D,L-lactide) (PLDL/PDL) | 80/20 to 98/2 |
| Polyglycolide/Poly(ε-caprolactone) (PG/PCL) | 10/90 to 40/60 |
| Poly(L-lactide)/Poly(ε-caprolactone) (PLL/PCL) | 2/98 to 40/60 |
| Trimethylene carbonate (TMC) | 100 |
| TMC/PCL | 60/40 to 95/5 |
| Poly(4-hydroxybutyrate) (P4HB) | 100 |
| P4HB/PLL | 90/10 to 70/30 |
| P4HB/PCL | 90/10 to 70/30 |

Using a biodegradable/bioabsorbable polymer, metal or ceramic material may allow for a wide range of filter conversion times.

With the vascular filter device of the invention the holding means may be employed to temporarily hold the filter elements 6 in the capturing position for any desired period of time. The invention is not limited to holding the filter elements in the capturing position for the periods of time described above.

It is appreciated that the holder members may be manufactured of biodegradable material alone, a combination of biodegradable and biostable materials, or, biostable materials alone.

The holder embodiments discussed above may be used to retain more than one filter in the capturing state, for example a double cone filter provided with a proximal fine cone and a distal coarse cone where the distal cone converts at a time period after the proximal cone. This would give extra protection in the initial stages of the treatment where pulmonary reserve may be compromised temporarily.

An intervention may be performed to extend the protection period either temporarily or permanently. For example, a catheter would grasp a hook or feature near the holder and deliver a claw, c-tube, coil, or memory wire to prevent the filter elements from opening. The claw, C-tube, or coil moves from an expanded state on the delivery catheter to a biased collapsed state where it retains the filter elements in the closed state. In the case of the double convertible cone filter, it may be desirable to extend the protection period only for the coarse distal filter.

A double cone filter may be provided with a convertible cone and a permanent cone. Ideally, the proximal cone is convertible and has finer capture efficiency. This provides long term coarse filtration with initial fine filtration.

It is appreciated that the filter embodiments discussed above can be used for general embolic protection in any blood vessel.

The invention is not limited to the embodiments hereinbefore described, with reference to the accompanying drawings, which may be varied in construction and detail.

The invention claimed is:

1. A vascular filter device comprising:
   a filter comprising a plurality of filter elements, the plurality of filter elements being movable from a capturing position to capture thrombus passing through a blood vessel to an open position to facilitate unrestricted blood flow, the plurality of filter elements each having a first end defining a loop, and
   a holder configured to hold the loops of the plurality of filter elements in the capturing position,
   wherein at least some of the loops overlap in the capturing position,
   wherein the plurality of filter elements is biased towards the open position, and the holder is configured to temporarily hold the plurality of filter elements in the capturing position until elapse of a predetermined period of time,
   wherein the loops of the plurality of filter elements are aligned axially by the holder.

2. The vascular filter device of claim 1, wherein at least part of the holder is biodegradable or bioabsorbable.

3. The vascular filter device of claim 1, when the holder includes an elongated element extending axially through the loops.

4. The vascular filter device of claim 3, wherein the holder is a straight pin.

5. The vascular filter device of claim 3, wherein each of the plurality of filter elements includes a distal portion extending radially from the elongated element.

6. The vascular filter device of claim 5, wherein the distal portions of the plurality of filter elements are spaced apart circumferentially around the elongated element.

7. The vascular filter device of claim 5, wherein each of the plurality of filter elements curves and extends axially from the distal portion.

8. The vascular filter device of claim 1, wherein the filter includes a tubular support structure supporting the plurality of filter elements, wherein second ends of the plurality of filter elements are coupled to the tubular support structure.

9. The vascular filter device of claim 8, wherein the first and second ends are located longitudinally within the tubular support structure.

10. A vascular filter device comprising:
    a plurality of filter elements movable from a capturing position to capture thrombus passing through a blood vessel to an open position to facilitate unrestricted blood flow, the plurality of filter elements each having a first end defining a loop, and an opposite second end;
    a holder configured to connect the loops of the plurality of filter elements in the capturing position; and
    a tubular support structure supporting the plurality of filter elements, wherein the second end of each of the plurality of filter elements is coupled to the tubular support structure;
    wherein at least some of the loops overlap in the capturing position;
    wherein the plurality of filter elements is biased towards the open position, and the holder is configured to temporarily hold the plurality of filter elements in the capturing position until elapse of a predetermined period of time,
    wherein the loops of the plurality of filter elements are aligned axially by the holder.

11. The vascular filter device of claim 10, wherein at least part of the holder is biodegradable or bioabsorbable.

12. The vascular filter device of claim 10, when the holder includes an elongated element extending axially through the loops.

13. The vascular filter device of claim 12, wherein the holder is a straight pin.

14. The vascular filter device of claim 12, wherein each of the plurality of filter elements includes a distal portion extending radially from the elongated element.

15. The vascular filter device of claim 14, wherein the distal portions of the plurality of filter elements are spaced apart circumferentially around the elongated element.

16. The vascular filter device of claim 14, wherein each of the plurality of filter elements curves and extends axially from the distal portion.

17. The vascular filter device of claim 10, wherein the first and second ends are located longitudinally within the tubular support structure.

* * * * *